(12) United States Patent
Rasmussen et al.

(10) Patent No.: US 11,130,969 B2
(45) Date of Patent: Sep. 28, 2021

(54) DIRECT TRANSFER OF POLYNUCLEOTIDES BETWEEN GENOMES

(71) Applicant: Novozymes A/S, Bagsvaerd (DK)

(72) Inventors: Michael Dolberg Rasmussen, Bagsvaerd (DK); Gitte Bak Poulsen, Bagsvaerd (DK)

(73) Assignee: Novozymes, A/S, Bagsvaerd (DK)

( * ) Notice: Subject to any disclaimer, the term of this patent is extended or adjusted under 35 U.S.C. 154(b) by 146 days.

(21) Appl. No.: 14/897,060

(22) PCT Filed: Jul. 4, 2014

(86) PCT No.: PCT/EP2014/064289
§ 371 (c)(1),
(2) Date: Dec. 9, 2015

(87) PCT Pub. No.: WO2015/004013
PCT Pub. Date: Jan. 15, 2015

(65) Prior Publication Data
US 2016/0115501 A1 Apr. 28, 2016

(30) Foreign Application Priority Data
Jul. 12, 2013 (EP) ..................................... 13176373

(51) Int. Cl.
*C12N 15/90* (2006.01)
*C12N 15/10* (2006.01)
*C12N 15/75* (2006.01)

(52) U.S. Cl.
CPC ....... *C12N 15/902* (2013.01); *C12N 15/1082* (2013.01); *C12N 15/75* (2013.01)

(58) Field of Classification Search
None
See application file for complete search history.

(56) References Cited

U.S. PATENT DOCUMENTS

| 6,485,949 B1 | 11/2002 | Piazza |
| 2009/0280569 A1 | 11/2009 | Jorgensen |
| 2010/0028944 A1 | 2/2010 | Berka et al. |

FOREIGN PATENT DOCUMENTS

| JP | 57-49862 | 3/1982 |
| WO | 2003083125 A1 | 10/2003 |
| WO | 03/095658 A1 | 11/2003 |
| WO | 2006/042548 A1 | 4/2006 |
| WO | 2008079895 A2 | 7/2008 |
| WO | 2011/120938 A2 | 10/2011 |
| WO | 2014052630 A1 | 4/2014 |
| WO | 2015004013 A1 | 1/2015 |

OTHER PUBLICATIONS

Zhang et al (Microbial Biotechnology, 4(1):97-150, 2011).*
Hoffmann et al (Applied and Environmental Microbiology 76(15):5046-57, 2010).*
Blee et al., Journal of Biological Chemistry, vol. 268, No. 3, pp. 1708-1715 (1993).
Hahn et al., Molecular Microbiology, vol. 18, No. 4, pp. 755-767 (1995).
Hols et al., Gene, vol. 118, No. 1, pp. 31-38 (1992).
Miyazawa et al., Journal of Food Science, vol. 58, No. 1, pp. 66-70 (1993).
Tsuge et al., Antimicrobial Agents and Chemotherapy, vol. 49, No. 11, pp. 4641-4648 (2005).
Hahn et al, 1994, J Bacteriol 176(18), 5753-5761.
Hahn et al, 1996, Mol Microbiol 21(4), 763-775.
Persuh et al, 1999, Mol Microbiol 33(4), 886-894.
Turgay et al, 1998, The EMBO Journal 17(22), 6730-6738.
Priority document of WO 2014-052630.
Priority document of EP 13176373.
Anonymous, Experimental report, pp. 1-18.
Felle, Max F. Curriculum Vitae.
Dubnau, David, American Society For Microbiology, Genetic Exchange and Homologous Recombination, Chapter 39, pp. 555-584.
Olempska-Beer, Chemical and Technical Assessment, 61st JEFCFA, Alpha-Amylase From Bacillus Licheniformis Containing A Genetically Engineered Alpha-Amylase Gene From B-Licheniformis (Thermostable).
Michael. B. et al., The EMBO Journal, vol. 3, No. 12, pp. 2879-2884, 1984, Recombination efficiency is a quadratic function of the length of homology during plasmid transformation of Bacillus subtillis protoplasts and *Escherichia coil* competent cells.

* cited by examiner

*Primary Examiner* — Patricia Duffy
(74) *Attorney, Agent, or Firm* — Eric J. Fechter

(57) ABSTRACT

The present invention provides methods for directly transferring a recombinant polynucleotide of interest from the chromosome of a prokaryotic donor cell to the chromosome of a prokaryotic recipient cell of another species, wherein the polynucleotide of interest comprises at least one coding sequence of interest, preferably one gene of interest and a selectable marker, wherein said polynucleotide of interest in the chromosome of the donor cell is flanked on each side by a polynucleotide region derived from the chromosome of the recipient cell, and wherein the flanking polynucleotide regions are of sufficient size and sequence identity to allow double homologous recombination with the corresponding regions in the chromosome of the recipient cell.

9 Claims, 8 Drawing Sheets

Specification includes a Sequence Listing.

SOE-fragment from Example 1

SOE fragment from Example 3

SOE fragment from Example 5

MOL3034 ara locus 18218 bp – Example 6

Chromosomal ara locus of MOL3041 - 14889 bp – Example 8 ara-aprH cassette in MOL3053 – 17505 bp – Example 10

Figure 8
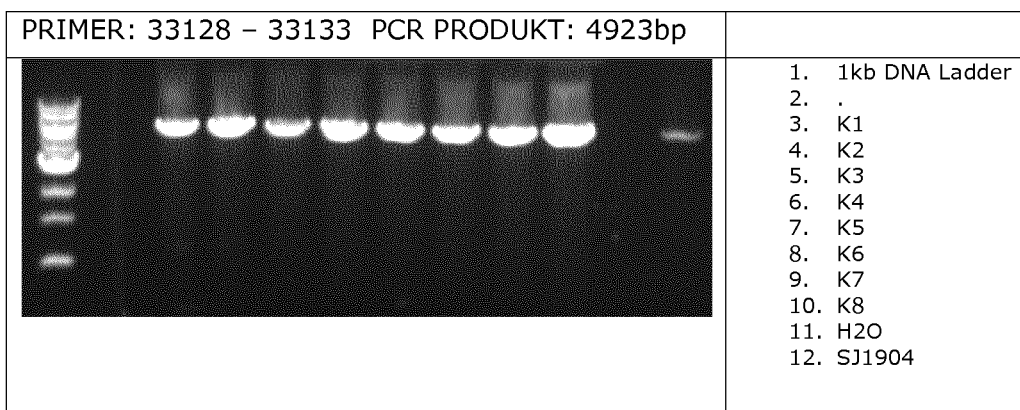
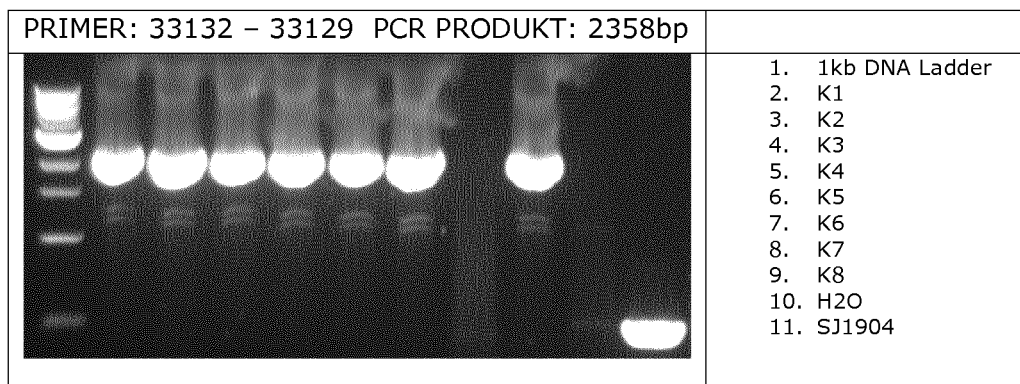

TaHy9 transformant from Example 16

Figure 10
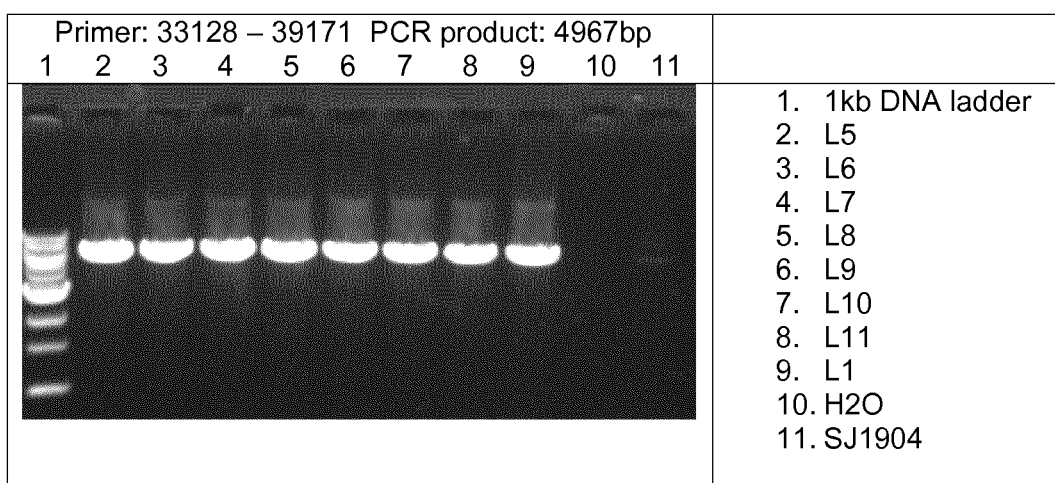
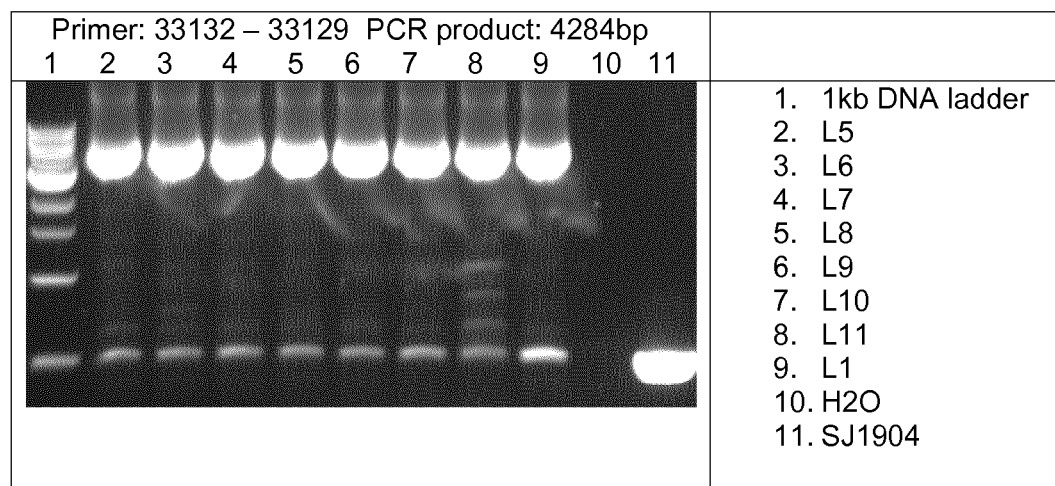

DIRECT TRANSFER OF POLYNUCLEOTIDES BETWEEN GENOMES

CROSS-REFERENCE TO RELATED APPLICATIONS

This application is a 35 U.S.C. 371 national application of PCT/EP2014/064289 filed Jul. 4, 2014, which claims priority or the benefit under 35 U.S.C. 119 of European application No. 13176373.2 filed Jul. 12, 2013. The contents of each application are fully incorporated herein by reference.

REFERENCE TO SEQUENCE LISTING

This application contains a Sequence Listing in computer readable form. The computer readable form is incorporated herein by reference.

FIELD OF THE INVENTION

The present invention provides methods for directly transferring a recombinant polynucleotide of interest from the chromosome of a prokaryotic donor cell to the chromosome of a prokaryotic recipient cell of another species, wherein the polynucleotide of interest comprises at least one coding sequence of interest, preferably one gene of interest and a selectable marker, wherein said polynucleotide of interest in the chromosome of the donor cell is flanked on each side by a polynucleotide region derived from the chromosome of the recipient cell, and wherein the flanking polynucleotide regions are of sufficient size and sequence identity to allow double homologous recombination with the corresponding regions in the chromosome of the recipient cell.

BACKGROUND OF THE INVENTION

In the area of industrial biotechnology, especially in relation to secreted polypeptides, such as, enzymes, *Bacillus subtilis* is by far the preferred host microorganism when new genes are to be cloned and screened. This is because of the high transformation and recombination frequencies in this species, which allow quick and easy transformation of a gene into the *B. subtilis* host and integration into its chromosome for subsequent screening.

It is well known that these high frequencies also allow easy transfer of genes from one *B. subtilis* to another by simple transformation with chromosomal DNA. However, *B. subtilis* is not necessarily the most preferred expression host once a gene of interest has been identified in a screening process and, unfortunately, it is very often difficult and cumbersome to transfer chromosomally-integrated heterologous DNA further on to other species desired for industrial expression, for example, to a *Bacillus licheniformis* host.

SUMMARY OF THE INVENTION

The present invention allows easy transfer of heterologous chromosomally integrated polynucleotides between different species.

In the examples below we succeeded in first cloning sufficiently large up- and downstream flanking DNA regions from a *B. licheniformis* recipient cell to a *B. subtilis* donor, then integrating a gene of interest and a selectable marker between the flanking DNA regions in the *B. subtilis* donor. Subsequently we transferred the gene of interest into the *B. licheniformis* recipient by transforming *B. licheniformis* with chromosomal DNA from the *B. subtilis* donor, whereby the gene of interest was site-specifically integrated into the chromosome of the *B. licheniformis* recipient through homologous recombination between the two flanking DNA regions in the incoming chromosomal DNA from the *B. subtilis* donor and the corresponding identical regions in the *B. licheniformis* chromosome.

This technique may be of particular relevance for transferring larger polynucleotides of interest, such as, operons or functional multi gene clusters between species.

Accordingly, in one aspect the present invention relates to a method for directly transferring a recombinant polynucleotide of interest from the chromosome of a prokaryotic donor cell to the chromosome of a prokaryotic recipient cell of another species, wherein the polynucleotide of interest comprises at least one coding sequence of interest, preferably one gene of interest and a selectable marker, wherein said polynucleotide of interest in the chromosome of the donor cell is flanked on each side by a polynucleotide region derived from the chromosome of the recipient cell, and wherein the flanking polynucleotide regions are of sufficient size and sequence identity to allow double homologous recombination with the corresponding regions in the chromosome of the recipient cell; the method comprising the steps of:
   a) providing chromosomal DNA from the donor cell, said DNA comprising the polynucleotide of interest flanked on each side by a polynucleotide region derived from the chromosome of the recipient prokaryotic cell;
   b) transforming the recipient cell with the DNA from step (a); and
   c) selecting a successfully transformed recipient cell, wherein the polynucleotide of interest comprising the selectable marker has been integrated into its chromosome.

Preferably the selectable marker has been integrated into the chromosome in step (c) via homologous recombination between the flanking regions in the DNA and their corresponding chromosomal regions in the recipient cell.

Accordingly, in one aspect the present invention relates to a method for directly transferring a recombinant polynucleotide of interest from the chromosome of a prokaryotic donor cell to the chromosome of a prokaryotic recipient cell of another species, comprising:
   a) providing chromosomal DNA from the donor cell, said DNA comprising the polynucleotide of interest flanked on each side by a polynucleotide region derived from the chromosome of the recipient prokaryotic cell and of sufficient size and sequence identity to allow double homologous recombination with the corresponding regions in the chromosome of the recipient cell;
   b) transforming the recipient cell with the DNA from step (a); and
   c) selecting a transformed recipient cell, wherein the polynucleotide of interest comprising the selectable marker has been integrated into the chromosome of the recipient cell.

In a second aspect, the invention relates to a method of screening a gene library for an encoded activity of interest, said method comprising the steps of:
   a) providing a prokaryotic donor cell comprising in its chromosome a polynucleotide of interest which in turn comprises the gene library and a selectable marker, wherein said polynucleotide of interest is flanked on each side by a polynucleotide region derived from the chromosome of a recipient prokaryotic cell of another species, and wherein the flanking polynucleotide regions are of sufficient size and sequence identity to allow double homologous recombination with the corresponding regions in the chromosome of the recipient cell;
  b) screening the gene library for an encoded activity while it resides in the chromosome of the prokaryotic donor cell and selecting a prokaryotic donor clone of interest,
  c) providing chromosomal DNA from the clone cell of step (b);
  d) transforming the recipient cell with the DNA from step (c); and
  e) selecting a successfully transformed recipient cell, wherein the polynucleotide of interest comprising the selectable marker has been integrated into its chromosome.

Preferably the selectable marker has been integrated into the chromosome in step (e) via homologous recombination between the flanking regions in the DNA and their corresponding chromosomal regions in the recipient cell.

BRIEF DESCRIPTION OF DRAWINGS

FIG. 8 shows pictures of PCR analysis agarose gel electrophoreses for the PCR verification of the transformant from example 15.

FIG. 10 shows pictures of PCR analysis agarose gel electrophoreses for the PCR verification of the transformant from example 16.

DEFINITIONS

Figure 1:
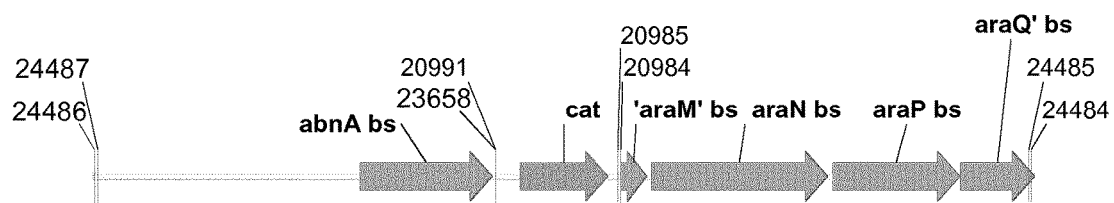
FIG. 1 shows the SOE-fragment from example 1 with positions of genes and primers.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Disruption: The term "disruption" means that a coding region and/or control sequence of a referenced gene is partially or entirely modified (such as by deletion, insertion, and/or substitution of one or more nucleotides) resulting in the absence (inactivation) or decrease in expression, and/or the absence or decrease of enzyme activity of the encoded polypeptide. The effects of disruption can be measured using techniques known in the art such as detecting the absence or decrease of enzyme activity using cell-free extract measurements referenced herein; or by the absence or decrease of corresponding mRNA (e.g., at least 25% decrease, at least 50% decrease, at least 60% decrease, at least 70% decrease, at least 80% decrease, or at least 90% decrease); the absence or decrease in the amount of corresponding polypeptide having enzyme activity (e.g., at least 25% decrease, at least 50% decrease, at least 60% decrease, at least 70% decrease, at least 80% decrease, or at least 90% decrease); or the absence or decrease of the specific activity of the corresponding polypeptide having enzyme activity (e.g., at least 25% decrease, at least 50% decrease, at least 60% decrease, at least 70% decrease, at least 80% decrease, or at least 90% decrease). Disruptions of a particular gene of interest can be generated by methods known in the art, e.g., by directed homologous recombination (see Methods in Yeast Genetics (1997 edition), Adams, Gottschling, Kaiser, and Stems, Cold Spring Harbor Press (1998)). Techniques to disrupt Bacillus genes are described herein and have been demonstrated in the art (see Stahl & Ferrari, 1984, J. Bacteriol. 158: 411-418).

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment–Total Number of Gaps in Alignment)

DETAILED DESCRIPTION OF THE INVENTION

In one aspect the present invention relates to a method for directly transferring a recombinant polynucleotide of interest from the chromosome of a prokaryotic donor cell to the chromosome of a prokaryotic recipient cell of another species, wherein the polynucleotide of interest comprises at least one coding sequence of interest, preferably one gene of interest and a selectable marker, wherein said polynucleotide of interest in the chromosome of the donor cell is flanked on each side by a polynucleotide region derived from the chromosome of the recipient cell, and wherein the flanking polynucleotide regions are of sufficient size and sequence identity to allow double homologous recombination with the corresponding regions in the chromosome of the recipient cell; the method comprising the steps of:

a) providing chromosomal DNA from the donor cell, said DNA comprising the polynucleotide of interest flanked on each side by a polynucleotide region derived from the chromosome of the recipient prokaryotic cell;

b) transforming the recipient cell with the DNA from step (a); and c) selecting a successfully transformed recipient cell, wherein the polynucleotide of interest comprising the selectable marker has been integrated into its chromosome.

Preferably the selectable marker has been integrated into the chromosome in step (c) via homologous recombination between the flanking regions in the DNA and their corresponding chromosomal regions in the recipient cell.

Sources of Polynucleotides

A polynucleotide or gene encoding a polypeptide having an activity of interest of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted.

The polynucleotide may be a bacterial polynucleotide. For example, the polynucleotide may be a Gram-positive bacterial polynucleotide such as a *Bacillus*, *Clostridium*, *Enterococcus*, *Geobacillus*, *Lactobacillus*, *Lactococcus*, *Oceanobacillus*, *Staphylococcus*, *Streptococcus*, or *Streptomyces* polynucleotide, or a Gram-negative bacterial polynucleotide such as a *Campylobacter*, *E. coli*, *Flavobacterium*, *Fusobacterium*, *Helicobacter*, *Ilyobacter*, *Neisseria*, *Pseudomonas*, *Salmonella*, or *Ureaplasma* polynucleotide.

In one aspect, the polynucleotide is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* polynucleotide.

In another aspect, the polynucleotide is a *Streptococcus equisimilis*, *Streptococcus pyogenes*, *Streptococcus uberis*, or *Streptococcus equi* subsp. *Zooepidemicus* polynucleotide.

In another aspect, the polynucleotide is a *Streptomyces achromogenes*, *Streptomyces avermitilis*, *Streptomyces coelicolor*, *Streptomyces griseus*, or *Streptomyces lividans* polynucleotide.

The polynucleotide may be a fungal polynucleotide. For example, the polynucleotide may be a yeast polynucleotide such as a *Candida*, *Kluyveromyces*, *Pichia*, *Saccharomyces*, *Schizosaccharomyces*, or *Yarrowia* polynucleotide; or a filamentous fungal polynucleotide such as an *Acremonium*, *Agaricus*, *Alternaria*, *Aspergillus*, *Aureobasidium*, *Botryosphaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polynucleotide.

In another aspect, the polynucleotide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polynucleotide.

In another aspect, the polynucleotide is an *Acremonium cellulolyticus*, *Aspergillus aculeatus*, *Aspergillus awamori*,

*Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* polynucleotide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polynucleotide may be identified and obtained from other sources including microorganisms isolated from nature (e.g., soil, composts, water, etc.) or DNA samples obtained directly from natural materials (e.g., soil, composts, water, etc.). Techniques for isolating microorganisms and DNA directly from natural habitats are well known in the art. The polynucleotide may then be obtained by similarly screening a genomic DNA or cDNA library of another microorganism or mixed DNA sample. Once a polynucleotide encoding a polypeptide has been detected, the polynucleotide can be isolated or cloned by utilizing techniques that are known to those of ordinary skill in the art (see, e.g., Sambrook et al., 1989, supra).

Polynucleotides

The present invention also relates to isolated polynucleotides or at least one one coding sequence of interest, preferably gene of interest encoding a polypeptide or an activity of interest, as well as to nucleic acid constructs, expression vectors and recombinant host cells comprising such polynucleotides.

The encoded polypeptide may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the polypeptide or activity of interest encoded by the at least one coding sequence of interest, preferably one gene is a hormone, enzyme, receptor or portion thereof, antibody or portion thereof, or reporter. For example, the protein may be a hydrolase, isomerase, ligase, lyase, oxidoreductase, or transferase; more preferably the enzyme is an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.

In another preferred embodiment, the at least one coding sequence of interest comprises one or several genes.

The at least one coding sequence of interest, preferably one gene of the present invention may be obtained from any prokaryotic, eukaryotic, or other source. The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of a polynucleotide, e.g., a subsequence thereof, and/or by introduction of nucleotide substitutions that do not result in a change in the amino acid sequence of the encoded polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. Other examples of regulatory sequences are those that allow for gene amplification.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be one that, when introduced into the host cell, is integrated into the genome and replicated together with the chromosome(s) into which it has been integrated. The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance.

The vector preferably contains an element(s) that permits integration of the vector into the host cell's genome or autonomous replication of the vector in the cell independent of the genome.

For integration into the recipient host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the recipient host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

In a preferred embodiment of the first and second aspects of the invention, the flanking polynucleotide regions derived from the chromosome of the recipient cell comprise at least 100 nucleotides, more preferably at least 150, 200, 250, 300, 350, 400, 450, 500, 550, 600, 650, 700, 750, 800, 850, 900, 950, 1,000 nucleotides, most preferably they comprise between 100-5,000 nucleotides, between 100-4,000 nucleotides, between 100-3,000 nucleotides, between 100-2,000 nucleotides, between 100-1,000 nucleotides or between 1,000-10,000 nucleotides. It is preferred that each flanking polynucleotide region derived from the chromosome of the recipient cell are at least 80% identical to the corresponding region in the chromosome of the recipient cell; preferably at least 85%, 90%, 92%, 94%, 96%, 98% or at least 99% identical to the corresponding region in the chromosome of the recipient cell.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to prokaryotic donor and/or recipient host cells, comprising a polynucleotide of interest of the present invention. Chromosomal DNA of a donor cell comprising a polynucleotide of interest is introduced into a recipient cell as described herein. The term "host cell" encompasses any progeny of a parent cell that is not identical to the parent cell due to mutations that occur during replication. The choice of a host cell will to a large extent depend upon the gene encoding the polypeptide and its source.

The prokaryotic donor and/or recipient host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial donor and/or recipient host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells. In some embodiments, the host cell is mecA-disrupted. Preferably, the recipient cell is a *Bacillus* mecA-disrupted cell and most preferably the recipient cells is a *B. licheniformis* mecA-disrupted cell as employed in the examples below.

The bacterial donor and/or recipient cell host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial donor and/or recipient host cell may also be any *Streptomyces* cell including, but not limited to, *Streptomyces achromogenes, Streptomyces avermitilis, Streptomyces coelicolor, Streptomyces griseus*, and *Streptomyces lividans* cells.

In some preferred embodiments, the donor host cell is *Bacillus subtilis* and the recipient host cell is *Bacillus licheniformis*. In some embodiments, the donor host cell is *E. coli* and the recipient host cell is a *Bacillus* cell, such as *Bacillus subtilis* or *Bacillus licheniformis*.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

Methods of Screening

In the area of industrial biotechnology, especially in relation to secreted polypeptides, such as, enzymes, *Bacillus subtilis* is by far the preferred host microorganism when new genes are to be cloned and screened. This is because of the high transformation and recombination frequencies in this species, which allow quick and easy transformation of a gene into the *B. subtilis* host and integration into its chromosome for subsequent screening.

It is well known that these high frequencies also allow easy transfer of genes from one *B. subtilis* to another by simple transformation with chromosomal DNA. However, *B. subtilis* is not necessarily the most preferred expression host once a gene of interest has been identified in a screening process and, unfortunately, it is very often difficult and cumbersome to transfer chromosomally-integrated heterologous DNA further on to other species desired for industrial expression, for example, to a *Bacillus licheniformis* host.

Accordingly, in a preferred embodiment of the first aspect of the invention, the at least one coding sequence of interest, preferably one gene of interest comprises a gene library, and wherein said method comprises the additional first steps of:
i) screening the gene library for an encoded activity while it resides in the chromosome of the prokaryotic donor cell, and
ii) selecting a prokaryotic donor clone of interest, before chromosomal DNA of the clone of interest is provided and transformed into the recipient cell in accordance with steps a)-c) of the method of the first aspect.

In a second aspect, the invention relates to a method of screening a gene library for an encoded activity of interest, said method comprising the steps of:
a) providing a prokaryotic donor cell comprising in its chromosome a polynucleotide of interest which in turn comprises the gene library and a selectable marker, wherein said polynucleotide of interest is flanked on each side by a polynucleotide region derived from the chromosome of a recipient prokaryotic cell of another species, and wherein the flanking polynucleotide regions are of sufficient size and sequence identity to allow double homologous recombination with the corresponding regions in the chromosome of the recipient cell;
b) screening the gene library for an encoded activity while it resides in the chromosome of the prokaryotic donor cell and selecting a prokaryotic donor clone of interest,
c) providing chromosomal DNA from the clone cell of step (b);
d) transforming the recipient cell with the DNA from step (c); and
e) selecting a successfully transformed recipient cell, wherein the polynucleotide of interest comprising the selectable marker has been integrated into its chromosome.

Preferably the selectable marker has been integrated into the chromosome in step (e) via homologous recombination between the flanking regions in the DNA and their corresponding chromosomal regions in the recipient cell.

Methods of Production

The present invention also relates to methods of producing a polypeptide of the present invention, comprising (a) cultivating a successfully transformed prokaryotic recipient cell under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Fermentation Broth Formulations or Cell Compositions

The present invention also relates to a fermentation broth formulation or a cell composition comprising a successfully transformed prokaryotic recipient cell of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

The following examples are provided by way of illustration and are not intended to be limiting of the invention.

EXAMPLES

The following examples provide a description of a series of DNA constructs that have been carried out. In examples 1 through 6 constructions were made in *B. subtilis*, wherein the two antibiotic resistance markers erm and spc are flanked by 5.5 kb *B. licheniformis* DNA from the arabinose operon and inserted in the arabinose operon on the chromosome of *B. subtilis*. These constructions were made in three sequential steps by first using the cat marker to delete a part of the ara operon in *B. subtilis*; then replacing the cat marker with the erm marker and the first flanking region of the *B. licheniformis* arabinose region and, finally, in the third step introducing the spc marker together with the second flanking region of the *B. licheniformis* arabinose operon to create the final construct for the transformation experiment described in example 15.

In examples 7 and 8 the erm and spc markers from example 6 were replaced with the cat marker to prepare for integration of the expression cassette with the aprH and spc genes.

In examples 9 and 10 the cat marker was replaced with the aprH expression cassette and the spc marker gene to create the final construct for the transformation experiment in example 16.

Materials and Methods

Media

*Bacillus* strains were grown on TBAB (Tryptose Blood Agar Base, Difco Laboratories, Sparks, Md., USA) or LB agar (10 g/l Tryptone, 5 g/l yeast extract, 5 g/l NaCl, 15 g/l agar) plates or in LB liquid medium (10 g/l Tryptone, 5 g/l yeast extract, 5 g/l NaCl).

To select for erythromycin resistance, agar media were supplemented with 1 µg/ml erythromycin+25 µg/ml lincomycin and liquid media were supplemented with 5 µg/ml erythromycin. To select for spectinomycin resistance, agar media were supplemented with 120 µg/ml spectinomycin. To select for chloramphenicol resistance, agar and liquid media were supplemented with 6 µg/ml chloramphenicol.

To screen for protease phenotypes agar plates were supplemented with 1% skim milk to allow halos to form around the colonies that produce protease.

Spizizen I medium consists of 1× Spizizen salts (6 g/l $KH_2PO_4$, 14 g/l $K_2HPO_4$, 2 g/l $(NH_4)_2SO_4$, 1 g/l sodium citrate, 0.2 g/l $MgSO_4$, pH 7.0), 0.5% glucose, 0.1% yeast extract, and 0.02% casein hydrolysate.

Spizizen I-xyl medium consists of 1× Spizizen salts (6 g/l $KH_2PO_4$, 14 g/l $K_2HPO_4$, 2 g/l $(NH_4)_2SO_4$, 1 g/l sodium citrate, 0.2 g/l $MgSO_4$, pH 7.0), 1% xylose, 0.1% yeast extract, and 0.02% casein hydrolysate.

Spizizen II medium consists of Spizizen I medium supplemented with 0.5 mM $CaCl_2$, and 2.5 mM $MgCl_2$.

Spizizen II-xyl medium consists of Spizizen I-xyl medium supplemented with 0.5 mM $CaCl_2$, and 2.5 mM $MgCl_2$.

Strains

PL1801: This strain is the *B. subtilis* DN1885 with disrupted aprE and nprE genes encoding the alkaline protease and neutral protease respectively (Diderichsen, B., Wedsted, U., Hedegaard, L., Jensen, B. R., Sjøholm, C. (1990) Cloning of aldB, which encodes alpha-acetolactate decarboxylase, an exoenzyme from *Bacillus brevis*. J. Bacteriol., 172, 4315-4321).

A164: This strain is a *B. subtilis* wild type isolate (ATCC 6051a) 16844: This strain derived from the *Bacillus subtilis* type strain 168 (BGSC 1A1, *Bacillus* Genetic Stock Center, Columbus, Ohio, USA) and has deletions in the spoIIAC, aprE, nprE, and amyE genes. The deletion of these four genes was performed essentially as described for *Bacillus subtilis* A164Δ5, which is described in detail in U.S. Pat. No. 5,891,701.

JA1343: This strain is the *B. subtilis* PL1801 with a disrupted spoIIAC gene (sigF). The genotype is: aprE, nprE, amyE, spoIIAC.

JA1622: This strain is the *B. subtilis* 168 derivative JA578 described in WO 0200907 A1 with a disrupted spoIIAC gene (sigF). The genotype is: amyE::repF (pE194), spoIIAC.

SJ1904: This strain is a *B. licheniformis* strain described in WO 08066931 A2. The gene encoding the alkaline protease (aprL) is inactivated.

MOL2999: This strain is the *B. subtilis* JA1622 where a chloramphenicol marker gene (cat) from pC194 is inserted into the arabinose operon (see example 1 and 2)

MOL3030: A 4.6 kb fragment of the arabinose operon from *B. licheniformis* SJ1904 is inserted into the arabinose operon of *B. subtilis* MOL2999. The arabinose operon fragment from *B. licheniformis* is inserted with an antibiotic marker gene erm (erythromycin marker). The integration event at the same time deletes the cat gene (see example 3 and 4).

MOL3034: *B. subtilis* MOL3030 into which a 5.5 kb fragment of the arabinose operon from *B. licheniformis* SJ1904 was inserted into the arabinose operon. The arabinose operon fragment from *B. licheniformis* was inserted with an antibiotic marker gene spc (spectinomycin marker). The strain is resistant to erythromycin and spectinomycin (see examples 5 and 6).

MOL3041: The erm and spc markers in *B. subtilis* MOL3034 are replaced with the cat marker. The cat marker is flanked by the two 5.5 kb fragments from *B. licheniformis* SJ1904 (see examples 7 and 8).

MOL3053: *B. subtilis* MOL3041 wherein the cat marker was replaced with a spc marker and an expression cassette holding the aprH protease gene from *B. clausii* (see examples 9 and 10).

MDT101: This strain is the *B. subtilis* 16844 wherein the *Bacillus licheniformis* M.Bli1904II DNA methyltransferase gene was inserted into the chromosome at the amyE locus in order to express the methyltransferase, thereby allowing *B. licheniformis* type of methylation of DNA in this *B. subtilis* host (U.S. Pat. No. 8,389,283 B2). The cat marker is co-inserted at the amyE locus.

AEB708: This strain is the JA1343 *B. subtilis* strain where the M.Bli1904II DNA methyltransferase gene described for MDT101 is inserted at the amyE locus by chromosomal transformation. Chromosomal DNA from MDT101 was transformed to competent JA1343 selecting for the cat marker.

MOL3037: *B. subtilis* AEB708 into which the chromosomal fragment from *B. subtilis* MOL3034 including the spc- and erm markers as well as the *B. licheniformis* DNA fragments were successfully transferred via a transformation with chromosomal DNA from MOL3034. This strain expresses the *Bacillus licheniformis* M.Bli1904II DNA methyltransferase (see example 11).

MOL3055: *B. subtilis* AEB708 into which a chromosomal fragment from *B. subtilis* MOL3053 including the spc marker, aprH expression cassette and *B. licheniformis* DNA fragments were successfully transferred via a transformation with chromosomal DNA from MOL3053. This strain expresses the *Bacillus licheniformis* M.Bli1904II DNA methyltransferase (see example 12).

TaHy9: *B. licheniformis* SJ1904 with a mecA deletion as described in example 13.

MDT232: *B. licheniformis* SJ1904 with a spectinomycin marker at the glpD locus (WO2008/079895)

Plasmids pC194: Plasmid isolated from *Staphylococcus aureus* (Horinouchi and Weisblum, 1982, J. Bacteriol. 150(2):815).

pE194: Plasmid isolated from *Staphylococcus aureus* (Horinouchi and Weisblum, 1982, J. Bacteriol. 1982, 150 (2):804).

pCR2.1-TOPO: Plasmid purchased from Invitrogen pBM293: Plasmid construction from example 7.

pNNB194: Plasmid (U.S. Pat. No. 5,958,728)

pBM294: Plasmid used for mecA deletion in *B. licheniformis* SJ1904 in example 7.

pSJ3358: pUC derived plasmid with spectinomycin marker from Tn554 (WO 96/23073)

pSJ3372: pUC derived plasmid with chloramphenicol marker from pC194 (U.S. Pat. No. 5,552,888)

Primers

TABLE 1

Primer and sequence overview

| Primer No./Seq. | SEQ ID NO | Nucleotide sequence 5'→ |
|---|---|---|
| 20984 | 1 | cactcccgagaggagaagtgctggctg |
| 20985 | 2 | cagccagcacttctcctctcgggagtgggagctgtaatataaaaacttc |
| 20990 | 3 | gtcaatcttttcttttaaaaaaagc |
| 20991 | 4 | gcttttttaaaagaaaagattgacgcaaagacgcatgtgttttggtttg |
| 23658 | 5 | gcttttttaaaagaaaagattgacaacaaacgaaaattggataaagtgg |
| 24484 | 6 | cagccgtccatccttgcagagtc |
| 24485 | 7 | gtccagcagatctcttggaaggc |
| 24486 | 8 | cacgcttcttttaagtacggag |
| 24487 | 9 | ccgcttcttctggtaatagaagc |
| 27094 | 10 | ctgcgcaaaagacataatcgattc |
| 27095 | 11 | ttcaataatcgcatccgattgcag |
| 27096 | 12 | ttcaataatcgcatccgattgcag |
| 30007 | 13 | aatgctgctcggtatgaccctttgcc |

TABLE 1-continued

Primer and sequence overview

| Primer No./Seq. | SEQ ID NO | Nucleotide sequence 5'→ |
|---|---|---|
| 30008 | 14 | caaacgcaggaggatgcggagcc |
| 30009 | 15 | gaatcgattatgtcttttgcgcagtttcctggaatgtgatccgcctg |
| 30011 | 16 | tgctttcgaagcattagacgtggatg |
| 30013 | 17 | ttcaacactcgttgatgccgatc |
| 30017 | 18 | gttttaaaagtaagcacctgttggtgctataaaattagcctaattgag |
| 30018 | 19 | gacggcaggctgacggctcaccttctttcctggaatgtgatccgcctg |
| 30019 | 20 | ccaacaggtgcttacttttaaaactacgtcatgctggttctcgaccattc |
| 30020 | 21 | gaaggtgagccgtcagcctgccgtc |
| 30590 | 22 | gaatcgattatgtcttttgcgcagccaatctagggtaagtaaattgag |
| 33128 | 23 | cataatgatataatgaagttgttcg |
| 33129 | 24 | cgccgatacgcctcatccactctgcc |
| 33132 | 25 | caagcgccgcagaacatggtagccgc |
| 33133 | 26 | ggttgataatgaactgtgctgattac |
| 35876 | 27 | ggaagcgcttgatcaatgtcttgactaaggttaaggtggatacacatc |
| 35878 | 28 | cgcgtggtacccggggatcctctagcatgctggttctcgaccattcaag |
| 35880 | 29 | cgtagacggcaaggcccgtatcc |
| 35881 | 30 | gtgcagttctctcgtcgatgtccgg |
| 35893 | 31 | cagtgaattctgatcaaatggttc |
| 35894 | 32 | gaaccatttgatcagaattcactggtcaagacattgatcaagcgcttcc |
| 35895 | 33 | gatgtgtatccaccttaacttagtcaagacattgatcaagcgcttcc |
| 36001 | 34 | caacgaaatttataagacgggc |
| 36002 | 35 | gcccgtcttataaatttcgttgatgctggttctcgaccattcaag |
| 36817 | 36 | gaaaacaagagcgtcagcacgg |
| 36818 | 37 | caggtgaggaaatcgcgacagctg |
| 39171 | 38 | gttcgggttcttcaaatatttctcc |
| 39950 | 39 | gaacgttgcggtacctgatctagatctcgggttcttcaaatatttctcc |
| 39951 | 40 | gatctagatcaggtaccgcaacgttc |
| 656520 | 41 | ctagaggatccccgggtaccacgcg |
| 0612056 | 42 | gaattccattaatagctgctg |
| 0612057 | 43 | tccatactctttcagcatggtcttcgatatcaccgt |
| 0612058 | 44 | acggtgatatcgaagaccatgctgaaagagtatgga |
| 0612060 | 45 | ctcgagcgcatcctcccaaaatc |

Molecular Biological Methods

DNA manipulations and transformations were performed by standard molecular biology methods as described in:

Sambrook et al. (1989): Molecular cloning: A laboratory manual. Cold Spring Harbor laboratory, Cold Spring Harbor, N.Y.

Ausubel et al. (eds) (1995): Current protocols in Molecular Biology. John Wiley and Sons.

Harwood and Cutting (eds) (1990): Molecular Biological Methods for *Bacillus*. John Wiley and Sons.

Enzymes for DNA manipulation were obtained from New England Biolabs, Inc. and used essentially as recommended by the supplier.

Competent cells and transformation of *B. subtilis* was obtained as described in Yasbin et al. (1975): Transformation and transfection in lysogenic strains of *Bacillus subtilis*:

evidence for selective induction of prophage in competent cells. *J. Bacteriol.* 121, 296-304.

Competent cells and transformation of *B. licheniformis* was performed as described in Example 8.

Genomic DNA was prepared from several erythromycin/lincomycin sensitive isolates above accordingly to the method previously described (Pitcher et. al, supra) or by using the commercial available QIAamp DNA Blood Kit from Qiagen.

Example 1. Obtaining a SOE-PCR Fragment with Flanking Ara Regions for Integration of a Cat Gene and Deletion of araA-araB-araD-araL-araM in *B. subtilis* JA1622

By performing SOE-PCR with the primers and templates listed in Table 2, the cat marker was flanked by an upstream and downstream region of the ara operon from *B. subtilis* A164. The entire SOE-PCR fragment is depicted in FIG. 1. The nucleotide sequence of the fragment can be found in SEQ ID NO:46.

The conditions for the PCR were as follows: The respective DNA fragments were amplified by PCR using the Phusion Hot Start DNA Polymerase system (Thermo Scientific). The PCR amplification reaction mixture contained 1 μl (~0.1 μg) of template DNA, 2 μl of sense primer (20 pmol/μl), 2 μl of anti-sense primer (20 pmol/μl), 10 μl of 5λ PCR buffer with 7.5 mM $MgCl_2$, 8 μl of dNTP mix (1.25 mM each), 37 μl water, and 0.5 μl (2 U/μl) DNA polymerase mix. A thermocycler was used to amplify the fragment. The PCR products were purified from a 1.2% agarose gel with 1×TBE buffer using the Qiagen QIAquick Gel Extraction Kit (Qiagen, Inc., Valencia, Calif.) according to the manufacturer's instructions.

The purified PCR products were used in a subsequent PCR reaction to create a single fragment using splice overlapping PCR (SOE) using the Phusion Hot Start DNA Polymerase system (Thermo Scientific) as follows. The PCR amplification reaction mixture contained 50 ng of each of the three gel purified PCR products. The two nested SOE primers 24485 and 24487 was added at 2 μl (20 pmol/μl) and a thermocycler was used to assemble and amplify the SOE fragment of 6883 bp (FIG. 1). The resulting PCR product was used directly for transformation to *B. subtilis* host JA1622.

TABLE 2

SOE-PCR strategy for inserting the cat gene into the ara operon of JA1622

| | 1. PCRs | | | SOE-PCR | |
|---|---|---|---|---|---|
| Fragments | Template DNA from | Primers | Size (bp) | Primers | Size (bp) |
| ara fragment upstream | A164 chr DNA | 24486 & 20991 | 2982 | 24487 & 24485 | 6883 |
| cat gene | pC194 plasmid | 23658 & 20985 | 949 | | |
| ara fragment downstream | A164 chr DNA | 20984 & 24484 | 3048 | | |

Example 2. Transforming the SOE-PCR Fragment Described in Example 1 into *B. subtilis* JA 1622

The SOE-PCR fragment with the cat gene flanked by ara regions obtained in Example 1 was transformed into host strain *B. subtilis* JA1622, and transformants were selected for resistance against chloramphenicol, since the cat gene on the SOE-PCR fragment renders the strain resistant to this antibiotic. Correct insertion of the fragment was selected as chloramphenicol resistant transformants. Transformants were subsequently tested by PCR amplification of chromosomal DNA and sequencing of the resulting PCR fragment using appropriate primers. One correct strain was named MOL2999.

Example 3. Obtaining a SOE-PCR Fragment with Flanking Ara Regions for Integration of an erm Gene in *B. subtilis* MOL2999 and Insertion of a 4.6 kb Region of the Ara Operon from *B. licheniformis* SJ1904

Figure 2:
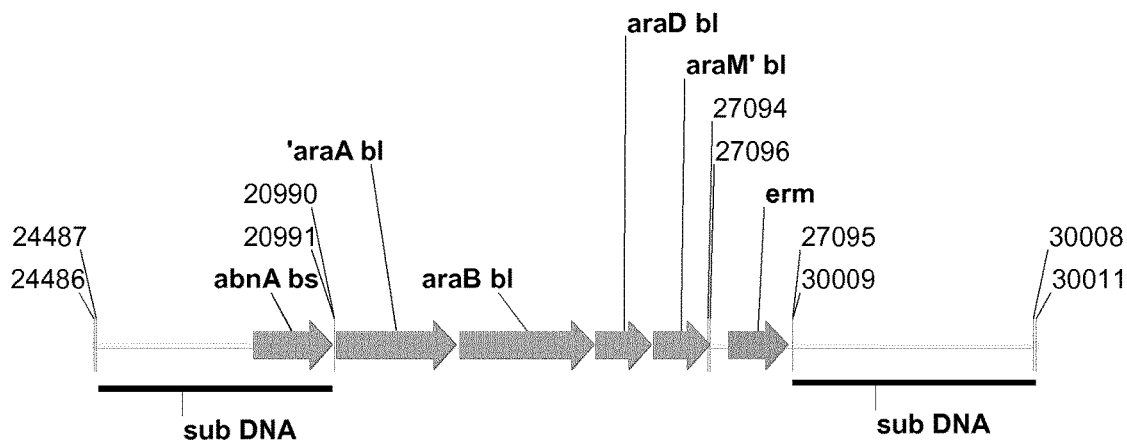
FIG. 2 shows the SOE-fragment from example 3 with positions of genes and primers.

By performing SOE-PCR with the primers and templates listed in Table 3, the erm resistance marker and a 4.6 kb region of the ara operon from *B. licheniformis* SJ1904 was flanked by an upstream and downstream region of the ara operon from *B. subtilis* A164. The entire SOE-PCR fragment is depicted in FIG. 2. The nucleotide sequence of the fragment can be found in SEQ ID NO:47.

The conditions for the PCR were as follows: The respective DNA fragments were amplified by PCR using the Phusion Hot Start DNA Polymerase system (Thermo Scientific). The PCR amplification reaction mixture contained 1 μl (~0.1 μg) of template DNA, 2 μl of sense primer (20 pmol/μl), 2 μl of anti-sense primer (20 pmol/μl), 10 μl of 5×PCR buffer with 7.5 mM $MgCl_2$, 8 μl of dNTP mix (1.25 mM each), 37 μl water, and 0.5 μl (2 U/μl) DNA polymerase mix. A thermocycler was used to amplify the fragment. The PCR products were purified from a 1.2% agarose gel with 1×TBE buffer using the Qiagen QIAquick Gel Extraction Kit (Qiagen, Inc., Valencia, Calif.) according to the manufacturer's instructions.

The purified PCR products were used in a subsequent PCR reaction to create a single fragment using splice overlapping PCR (SOE) and the Phusion Hot Start DNA Polymerase system (Thermo Scientific) as follows: The PCR amplification reaction mixture contained 50 ng of each of the four gel purified PCR products. The two nested SOE primers 24487 and 30008 were added at 2 μl (20 pmol/μl) and a thermocycler was used to assemble and amplify the SOE fragment of 9629 bp according to established PCR procedures (FIG. 2). The resulting PCR product was used directly for transformation to *B. subtilis* host MOL2999.

TABLE 3

SOE-PCR strategy for inserting the erm gene and a 4.6 kb ara region from *B. licheniformis* SJ1904 into the ara operon of *B. subtilis* MOL2999

| | 1. PCRs | | | SOE-PCR | |
|---|---|---|---|---|---|
| Fragments | Template DNA from | Primers | Size (bp) | Primers | Size (bp) |
| ara fragment upstream | A164 chr DNA | 24486 & 20991 | 2982 | 24487 & 30008 | 9629 |
| 4.6 kb fragment from SJ1904 | SJ1904 chr DNA | 20990 & 27094 | 4640 | | |
| erm gene | pE194 | 27096 & 27095 | 1042 | | |
| ara fragment downstream | A164 chr DNA | 30009 & 30011 | 3022 | | |

Example 4. Transforming the SOE-PCR Fragment Described in Example 3 into B. subtilis MOL2999

The SOE-PCR fragment with the erm resistance gene flanked by ara regions obtained in Example 3 was transformed into host strain B. subtilis MOL2999, selecting for resistance against erythromycin, since the erm gene on the SOE-PCR fragment renders the strain resistant to this antibiotic. Correct insertion of the fragment was selected as erythromycin resistant transformants. The clones were further tested by PCR on chromosomal DNA and subsequent sequencing of the resulting PCR fragment using appropriate primers. One correct strain was named MOL3030.

Example 5. Obtaining a SOE-PCR Fragment with Flanking Ara Regions for Integration of a spc Gene in B. subtilis MOL3030 and Insertion of a 5.1 kb Region of the Ara Operon from B. licheniformis SJ1904

Figure 3:
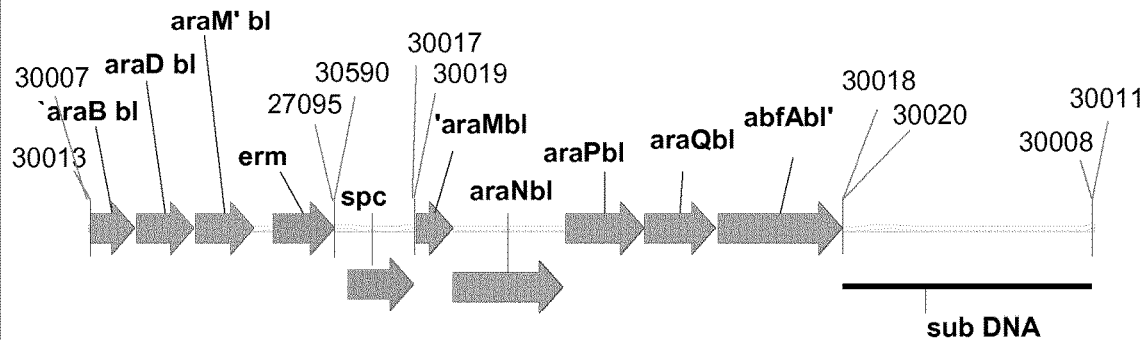
FIG. 3 shows the SOE-fragment from example 5 with positions of genes and primers.

By performing SOE-PCR with the primers and templates listed in Table 4, the spec resistance marker and a 5.1 kb region of the ara operon from B. licheniformis SJ1904 was flanked by an upstream and downstream region of the ara operon from B. subtilis A164 and B. licheniformis SJ1904. The entire SOE-PCR fragment is depicted in FIG. 3. The nucleotide sequence of the fragment can be found in SEQ ID NO:48.

The conditions for the PCR were as follows: The respective DNA fragments were amplified by PCR using the Phusion Hot Start DNA Polymerase system (Thermo Scientific). The PCR amplification reaction mixture contained 1 µl (~0.1 µg) of template genomic DNA, 2 µl of sense primer (20 pmol/µl), 2 µl of anti-sense primer (20 pmol/µl), 10 µl of 5×PCR buffer with 7.5 mM $MgCl_2$, 8 µl of dNTP mix (1.25 mM each), 37 µl water, and 0.5 µl (2 U/µl) DNA polymerase mix. A thermocycler was used to amplify the fragment. The PCR products were purified from a 1.2% agarose gel with 1×TBE buffer using the Qiagen QIAquick Gel Extraction Kit (Qiagen, Inc., Valencia, Calif.) according to the manufacturer's instructions.

The purified PCR products were used in a subsequent PCR reaction to create a single fragment using splice overlapping PCR (SOE) using the Phusion Hot Start DNA Polymerase system (Thermo Scientific) as follows. The PCR amplification reaction mixture contained 50 ng of each of the four gel purified PCR products. The two nested SOE primers 30007 and 30008 was added at 2 µl (20 pmol/µl) and a thermocycler was used to assemble and amplify the SOE fragment of 11869 by (FIG. 3). The resulting PCR product was used directly for transformation to B. subtilis host MOL3030.

TABLE 4

SOE-PCR strategy for inserting the erm gene and a 5.1 kb ara region from B. licheniformis SJ1904 into the ara operon of B. subtilis MOL3030

| | 1. PCRs | | | SOE-PCR | |
|---|---|---|---|---|---|
| Fragments | Template DNA from | Primers | Size (bp) | Primers | Size (bp) |
| ara fragment upstream | MOL3030 chr DNA | 30013 & 27095 | 2986 | 30007 & 30008 | 11869 |
| spc gene | pSJ3358 | 30590 & 30017 | 912 | | |

TABLE 4-continued

SOE-PCR strategy for inserting the erm gene and a 5.1 kb ara region from B. licheniformis SJ1904 into the ara operon of B. subtilis MOL3030

| | 1. PCRs | | | SOE-PCR | |
|---|---|---|---|---|---|
| Fragments | Template DNA from | Primers | Size (bp) | Primers | Size (bp) |
| 5.1 kb fragment from SJ1904 | SJ1904 chr DNA | 27096 & 27095 | 5086 | | |
| ara fragment downstream | A164 chr DNA | 30018 & 30011 | 3023 | | |

Example 6. Transforming the SOE-PCR Fragment Described in Example 5 into B. subtilis MOL3030

Figure 4:
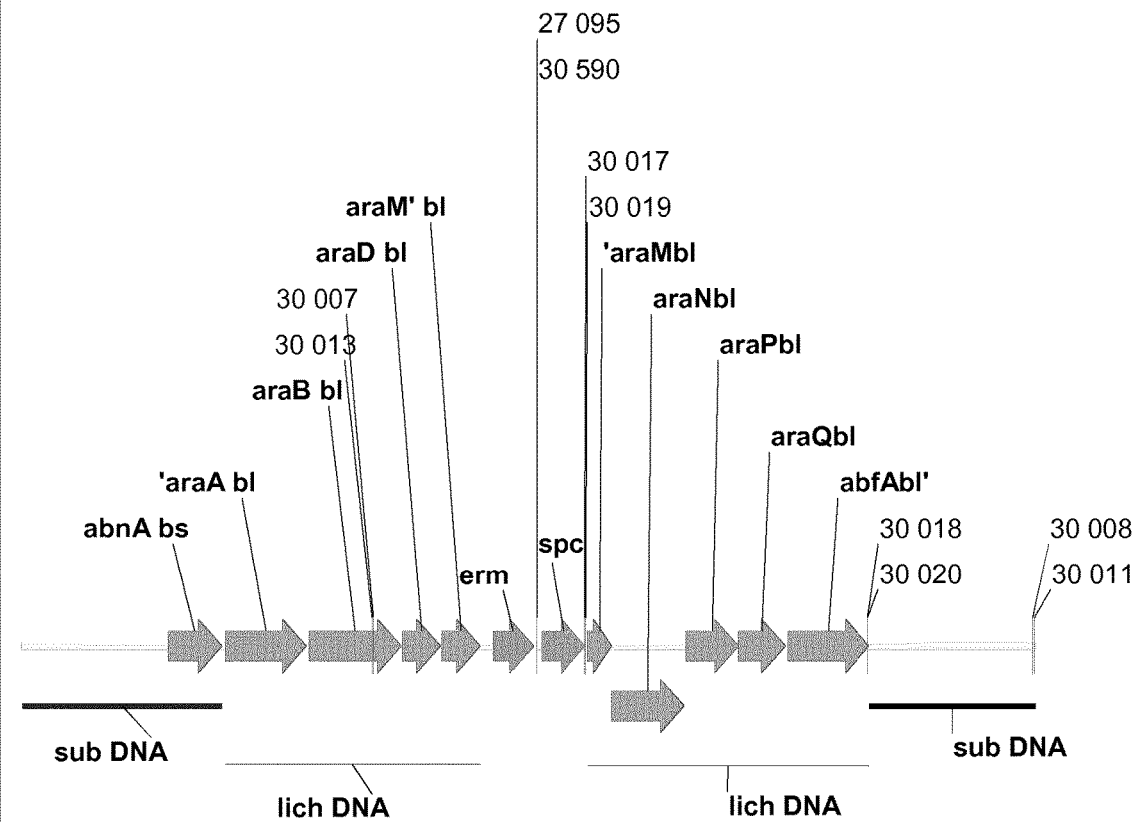
FIG. 4 shows the B. subtilis MOL3034 ara locus with positions of genes and primers for the SOE PCR in example 5; total size: 18218 bp.

The SOE-PCR fragment with the spc gene flanked by ara regions obtained in Example 5 was transformed into host strain B. subtilis MOL3030, selecting for resistance against spectinomycin, since the spc gene on the SOE-PCR fragment renders the strain resistant to this antibiotic. Correct insertion of the fragment was tested as spectinomycin and erythromycin resistant transformants. The clones were further tested by PCR on chromosomal DNA and subsequent sequencing of the resulting PCR fragment using appropriate primers. One correct strain was named MOL3034. The final engineered chromosomal locus in the ara region in MOL3034 is shown in FIG. 4.

Example 7. Obtaining a SOE-PCR Fragment with Flanking Ara Regions for Integration of a Cat Gene in B. subtilis MOL3034

By performing SOE-PCR with the primers and templates listed in Table 5, the cat resistance was flanked by an upstream and downstream 3 kb region of the ara operon from B. licheniformis SJ1904. The nucleotide sequence of the fragment can be found in SEQ ID NO:49.

The conditions for the PCR were as follows: The respective DNA fragments were amplified by PCR using the Phusion Hot Start DNA Polymerase system (Thermo Scientific). The PCR amplification reaction mixture contained 1 µl (~0.1 µg) of template genomic DNA, 2 µl of sense primer (20 pmol/µl), 2 µl of anti-sense primer (20 pmol/µl), 10 µl of 5×PCR buffer with 7.5 mM $MgCl_2$, 8 µl of dNTP mix (1.25 mM each), 37 µl water, and 0.5 µl (2 U/µl) DNA polymerase mix. A thermocycler was used to amplify the fragment. The PCR products were purified from a 1.2% agarose gel with 1×TBE buffer using the Qiagen QIAquick Gel Extraction Kit (Qiagen, Inc., Valencia, Calif.) according to the manufacturer's instructions.

The purified PCR products were used in a subsequent PCR reaction to create a single fragment using splice overlapping PCR (SOE) using the Phusion Hot Start DNA Polymerase system (Thermo Scientific) as follows. The PCR amplification reaction mixture contained 50 ng of each of the four gel purified PCR products. The two nested SOE primers 36817 and 36818 was added at 2 µl (20 pmol/µl) and a thermocycler was used to assemble and amplify the SOE fragment of 7330 bp. The resulting PCR product was used directly for transformation to B. subtilis host MOL3034.

TABLE 5

SOE-PCR strategy for replacing the spc and erm marker with
the cat gene into the ara operon of *B. subtilis* MOL3034

| | 1. PCRs | | | SOE-PCR | |
|---|---|---|---|---|---|
| Fragments | Template DNA from | Primers | Size (bp) | Primers | Size (bp) |
| ara fragment upstream | SJ1904 chr DNA | 35881 & 35895 | 3082 | 36818 & 36817 | 7330 |
| cat gene flanked by res sites | pSJ3372 | 35876 & 656520 | 1271 | | |
| ara fragment downstream | SJ1904 chr DNA | 35878 & 35880 | 3049 | | |

Example 8. Transforming the SOE-PCR Fragment Described in Example 7 into *B. subtilis* MOL3034

Figure 5:
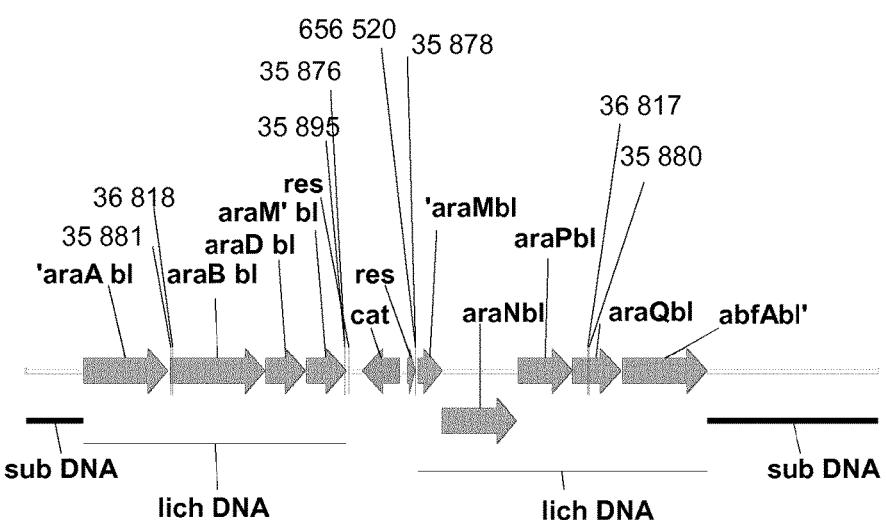
FIG. 5 shows the B. subtilis MOL3041 ara locus with positions of genes and primers for the SOE PCR in example 7; total size: 14889 bp.

The SOE-PCR fragment with the cat gene flanked by ara regions obtained in Example 7 was transformed into host strain *B. subtilis* MOL3034, selecting for resistance against chloramphenicol, since the cat gene on the SOE-PCR fragment renders the strain resistant to this antibiotic. Correct insertion of the fragment was tested as chloramphenicol resistant transformants. The clones were further tested to be sensitive to spectinomycin and erythromycin. The clones were further tested by PCR on chromosomal DNA and subsequent sequencing of the resulting PCR fragment using appropriate primers. One correct strain was named MOL3041. The chromosomal map of the ara region is shown in FIG. 5.

Example 9. Obtaining a SOE-PCR Fragment with Flanking Ara Regions for Integration of a spc Gene and an aprH Expression Cassette in *B. subtilis* MOL3041

By performing SOE-PCR with the primers and templates listed in Table 6, the spc resistance marker and an expression cassette with the aprH gene encoding the a serine-protease from *B. clausii* was flanked by an upstream and downstream 3 kb region of the ara operon from *B. licheniformis* SJ1904. The original signal peptide (SP) of aprH is changed to the SP of aprL from *B. licheniformis*. The expression cassette of aprH including the promoter and the cry3A mRNA stabilizer (cry3Astab) described in WO2008140615-A2 is ordered as synthetic DNA (SEQ ID NO:50). The nucleotide sequence of the entire SOE fragment can be found in SEQ ID NO:51.

The conditions for the PCR were as follows: The respective DNA fragments were amplified by PCR using the Phusion Hot Start DNA Polymerase system (Thermo Scientific). The PCR amplification reaction mixture contained 1 µl (~0.1 µg) of template genomic DNA, 2 µl of sense primer (20 pmol/µl), 2 µl of anti-sense primer (20 pmol/µl), 10 µl of 5×PCR buffer with 7.5 mM MgCl$_2$, 8 µl of dNTP mix (1.25 mM each), 37 µl water, and 0.5 µl (2 U/µl) DNA polymerase mix. A thermocycler was used to amplify the fragment. The PCR products were purified from a 1.2% agarose gel with 1×TBE buffer using the Qiagen QIAquick Gel Extraction Kit (Qiagen, Inc., Valencia, Calif.) according to the manufacturer's instructions.

The purified PCR products were used in a subsequent PCR reaction to create a single fragment using splice overlapping PCR (SOE) using the Phusion Hot Start DNA Polymerase system (Thermo Scientific) as follows. The PCR amplification reaction mixture contained 50 ng of each of the four gel purified PCR products. The two nested SOE primers 36817 and 36818 was added at 2 µl (20 pmol/µl) and a thermocycler was used to assemble and amplify the SOE fragment of 11869 bp. The resulting PCR product was used directly for transformation to *B. subtilis* host MOL3041.

TABLE 6

SOE-PCR strategy for replacing the cat marker with the spc gene and the
aprH expression cassette into the ara operon of *B. subtilis* MOL3041

| | 1. PCRs | | | SOE-PCR | |
|---|---|---|---|---|---|
| Fragments | Template DNA from | Primers | Size (bp) | Primers | Size (bp) |
| ara fragment upstream | SJ1904 chr DNA | 35881 & 35894 | 3084 | 36818 & 36817 | 9898 |
| spc gene flanked by res sites | pSJ3372 | 35893 & 39950 | 1548 | | |
| aprH expression cassette | Synthetic DNA (SEQ ID NO: 50) | 39951 & 36001 | 2341 | | |
| ara fragment downstream | SJ1904 chr DNA | 36002 & 35880 | 3045 | | |

Example 10. Transforming the SOE-PCR Fragment Described in Example 9 into *B. subtilis* MOL3041

Figure 6:
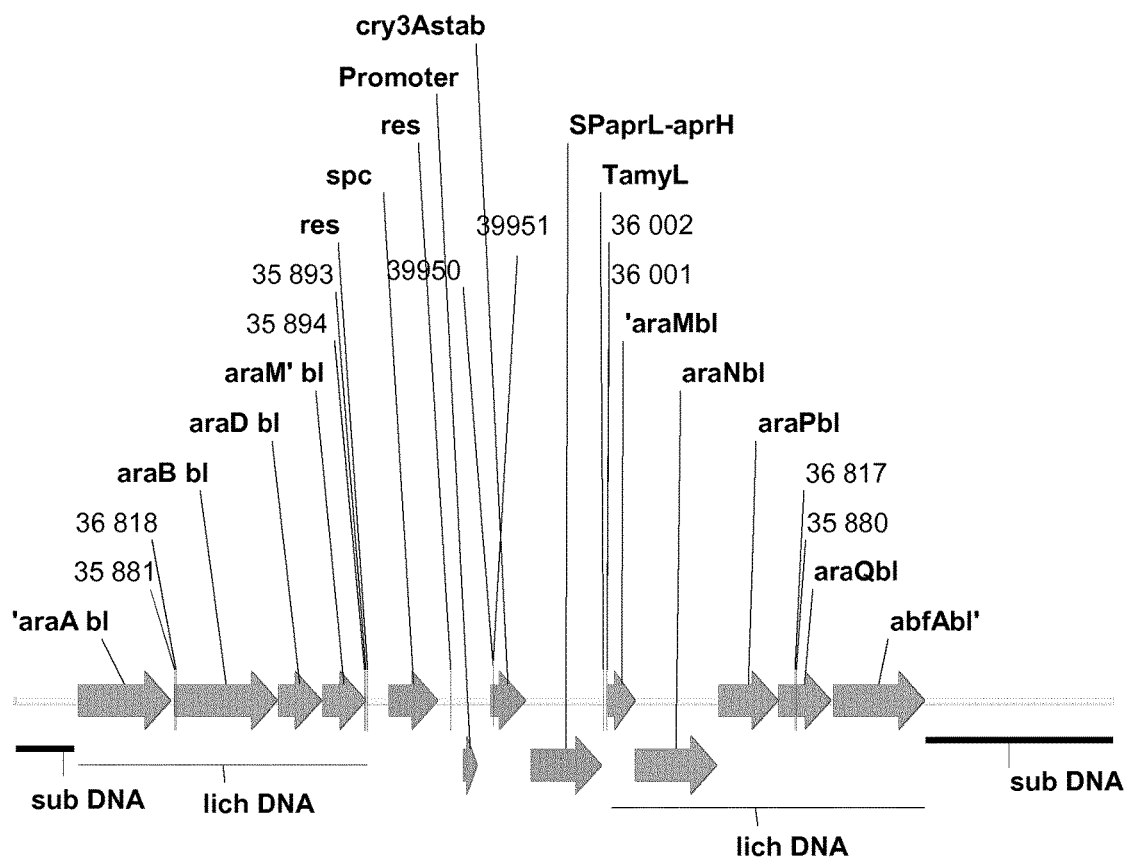
FIG. 6 shows the B. subtilis MOL3053 ara-aprH cassette with positions of genes and primers for the SOE PCR in example 9; total size: 17505 bp.

The SOE-PCR fragment with the spc gene and aprH expression cassette flanked by ara regions obtained in Example 9 was transformed into host strain *B. subtilis* MOL3041, selecting for resistance against spectinomycin, since the spc gene on the SOE-PCR fragment renders the strain resistant to this antibiotic. Correct insertion of the fragment was tested as spectinomycin resistant transformants showing protease activity. The clones were further tested to be sensitive to chloramphenicol. The clones were further tested by PCR on chromosomal DNA and subsequent sequencing of the resulting PCR fragment using appropriate primers. One correct strain was named MOL3053. The chromosomal map of the ara region is shown in FIG. 6.

Example 11. Transfer of the construction described in example 5 to the AEB708 strain holding the methyltransferase gene M.Bli1904II Chromosomal DNA from *B. subtilis* MOL3034 was isolated using QIAamp DNA Blood Kit from Qiagen. Competent *B. licheniformis* AEB708 cells were transformed with MOL3034 chromosomal DNA and plated on LB with 2 ug/ml erythromycin and 120 ug/ml spectinomycin. Colonies were tested with PCR to show the correct transfer of the MOL3034 construct described in example 5 and the presence of the *Bacillus licheniformis* M.Bli1904II DNA methyltransferase gene at the amyE locus. One correct clone was preserved as MOL3037.

Example 12. Transfer of the Construction Described in Example 9 to the AEB708 Strain Holding the Methyltransferase Gene M.Bli1904II Chromosomal DNA from MOL3053 was isolated using QIAamp DNA Blood Kit from Qiagen. Competent AEB708 cells where transformed with MOL3053 chromosomal DNA and plated on LB with 120 ug/ml spectinomycin. Colonies were tested with PCR to show the correct transfer of the MOL3053 construct described in example 9 and the presence of the *Bacillus licheniformis* M.Bli1904II DNA methyltransferase gene at the amyE locus. These clones also show clearing zones on protease indicator plates. One correct clone was preserved as MOL3055.

Example 13. Construction of a *B. licheniformis* mecA-Disrupted Strain (TaHy9)

Plasmid pBM294 was designed to delete 500 bp within the *B. licheniformis* mecA gene. Genomic DNA was isolated from *B. licheniformis* SJ1904 according the method previously described (Pitcher et. al, *Lett. Appl. Microbiol.*, 1989, 8, 151-156). A 323 bp fragment of the *B. licheniformis* SJ1904 chromosome, including the first 67 bp of the mecA coding sequence, was amplified by PCR using primers 0612056 and 0612057.

A cleavage site for restriction enzyme EcoRI was incorporated into primer 0612056. Primer 0612057 incorporates 18 bp corresponding to by 568 to 588 of the mecA coding sequence.

A second 288 bp fragment of the *B. licheniformis* SJ1904 chromosome, including the segment from nucleotides 568 to 639 of the mecA coding sequence, was amplified by PCR using primers 0612058 and 0612060.

A cleavage site for the XhoI restriction enzyme was incorporated into primer 0612060. Primer 0612058 incorporates 18 bp corresponding to by 47 to 67 of the mecA coding sequence. Primers 0612057 and 0612058 are complementary.

The respective DNA fragments were amplified by PCR using the Expand High Fidelity PCR system (Roche Diagnostics, Mannheim, Germany). The PCR amplification reaction mixture contained 4 µl (~1 µg) of *B. licheniformis* SJ1904 genomic DNA, 1 µl of sense primer (50 pmol/µl), 1 µl of anti-sense primer (50 pmol/µl), 10 µl of 5×PCR buffer with 15 mM MgCl$_2$, 1 µl of dNTP mix (10 mM each), 32.25 µl water, and 0.75 µl (3.5 U/µl) DNA polymerase mix. An Eppendorf Mastercycler thermocycler was used to amplify the fragment with the following settings: One cycle at 94° C. for 2 minutes; 10 cycles each at 94° C. for 15 seconds, 58° C. for 30 seconds, 72° C. for 20 seconds; 15 cycles each at 94° C. for 15 seconds, 58° C. for 30 seconds, 72° C. for 20 seconds plus 5 second elongation at each successive cycle, one cycle at 72° C. for 7 minutes; and 4° C. hold. The PCR products were purified from a 1.2% agarose (Amresco, Solon, Ohio) gel with 1×TBE buffer using the Qiagen QIAquick Gel Extraction Kit (Qiagen, Inc., Valencia, Calif.) according to the manufacturer's instructions.

The purified PCR products were used in a subsequent PCR reaction to create a single fragment using splice overlapping PCR (SOE) using the Expand High Fidelity$^{plus}$ PCR system (Roche Diagnostics) as follows. The PCR amplification reaction mixture contained 2 µl (~50 ng) of gel purified PCR product from primer combination 0612056/0612057, 2 µl (~50 ng) of gel purified PCR product from primer combination 0612058/0612060, 1 µl of primer 0612056 (50 pmol/µl), 1 µl of primer 0612060 (50 pmol/µl), 10 µl of 5×PCR buffer with 15 mM MgCl$_2$, 1 µl of dNTP mix (10 mM each), 32.25 µl water, and 0.75 µl (3.5 U/µl) DNA polymerase mix. An Eppendorf Mastercycler thermocycler was used to amplify the fragment with the following settings: One cycle at 94° C. for 2 minutes; 10 cycles each at 94° C. for 15 seconds, 58° C. for 30 seconds, 72° C. for 40 seconds; 15 cycles each at 94° C. for 15 seconds, 58° C. for 30 seconds, 72° C. for 40 seconds plus 5 second elongation at each successive cycle, one cycle at 72° C. for 7 minutes; and 4° C. hold. The resulting 611 bp PCR product was purified from a 1.2% agarose (Amresco) gel with 1×TBE buffer using the Qiagen QIAquick Gel Extraction Kit (Qiagen, Inc.) according to manufacturer's instructions.

The purified PCR product was cloned into plasmid pCR2.1-TOPO (Invitrogen) according to manufacturer's instructions, resulting is a plasmid designated pBM293. Plasmid pBM293 and plasmid pNNB194 (U.S. Pat. No. 5,958,728) were digested with restriction enzymes XhoI and EcoRI to isolate the 606 bp insert fragment and vector fragment, respectively. These fragments were isolated by 1% agarose gel electrophoresis using TBE buffer followed by purification using the Qiagen QIAquick Gel Extraction Kit (Qiagen, Inc.) according to manufacturer's instructions. The fragments were ligated using a Rapid DNA Ligation Kit following the manufacturer's instructions. A 2 µl aliquot of the ligation was used to transform *E. coli* Sure™ cells according to the manufacturer's instructions. Plasmid DNA was prepared from *E. coli* transformants and digested using restriction enzymes EcoRI and XhoI, followed by 0.7% agarose gel electrophoresis using TBE buffer and the plasmid identified as having the correct restriction pattern was designated pBM294.

The temperature-sensitive plasmid pBM294 was incorporated into the genome of *B. licheniformis* SJ1904 by chromosomal integration and excision according to the method previously described (U.S. Pat. No. 5,843,720). *B. licheniformis* SJ1904 transformants containing plasmid pBM294 were grown on TBAB selective medium at 50° C. to force integration of the vector. Desired integrants were chosen based on their ability to grow on TBAB erythromycin/lincomycin selective medium at 50° C. Integrants were then grown without selection in LB medium at 37° C. to allow excision of the integrated plasmid. Cells were plated on LB plates and screened for erythromycin-sensitivity.

Genomic DNA was prepared from several erythromycin/lincomycin sensitive isolates above according to the method previously described (Pitcher et. al, supra). Genomic PCR confirmed disruption of mecA and the resulting strain was designated TaHY9.

Example 14. Transformation Efficiency of a *B. licheniformis* mecA-Disrupted Strain (TaHy9) Using Chromosomal DNA from MDT232

The *B. licheniformis* mecA-disrupted strain TaHy9 from Example 13 was spread onto LB agar plates to obtain confluent growth after incubation at 37° C. overnight. After overnight incubation, approximately 2-3 ml of Spizizen I-xyl medium was added to each plate. Cells were scraped using sterile spreaders and transferred into 15 ml Falcon 2059 tubes. Approximately 500 µl of this culture was used to inoculate 50 ml Spizizen I-xyl medium. Growth was monitored using a Klett densitometer. At each cell density corresponding to Klett unit 140, 160, 180, and 200, 250 µl of the culture plus 250 µl Spizizen II-xyl medium containing 2 mM EGTA was added to a Falcon 2059 tube. One microgram of transforming DNA (*B. licheniformis* MDT232 chromosomal DNA containing a spectinomycin resistance expression cassette integrated at the glpD locus; see WO2008/079895) was added to each tube. Two microliters of 50 µg/ml spectinomycin was also added to the transformation mix. Tubes were incubated at 37° C. on a rotational shaker set at 250 rpm for 1 hour. Transformation reactions were plated to LB agar plates containing 120 µg/ml of spectinomycin. Colonies were counted the following day to determine transformation efficiency; results are shown in table 7 below.

Example 15. Transformation Efficiency of a *B. licheniformis* mecA-Disrupted Strain (TaHy9) Using Chromosomal DNA from *B. subtilis* MOL3037

Figure 7:
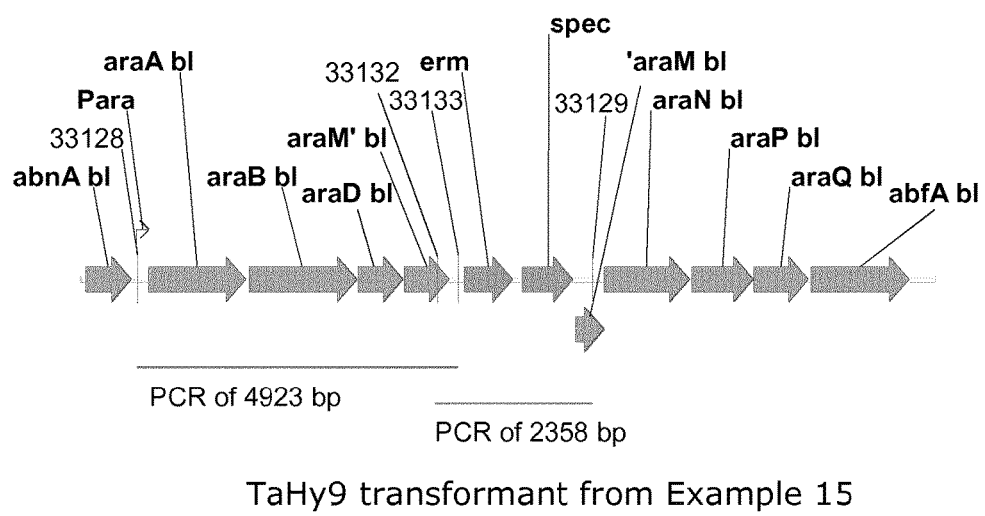
FIG. 7 shows the B. licheniformis TaHy9 transformant from example 15 with positions of genes and primers for PCR verification.

The *B. licheniformis* mecA-disrupted strain TaHy9 from Example 13 was spread onto LB agar plates to obtain confluent growth after incubation at 37° C. overnight. After overnight incubation, approximately 2-3 ml of Spizizen I-xyl medium was added to each plate. Cells were scraped using sterile spreaders and transferred into 15 ml Falcon 2059 tubes. Approximately 500 µl of this culture was used to inoculate 50 ml Spizizen I-xyl medium. Growth was monitored using a Klett densitometer. At each cell density corresponding to Klett unit 140, 160, 180, and 200, 250 µl of the culture plus 250 µl Spizizen II-xyl medium containing 2 mM EGTA was added to a Falcon 2059 tube. One microgram of transforming DNA (*B. subtilis* MOL3037 chromosomal DNA containing an erythromycin and spectinomycin resistance expression cassette integrated at the ara locus; see example 11) was added to each tube. Two microliters of 50 µg/ml spectinomycin and erythromycin was also included in the transformation mix. Tubes were incubated at 37° C. on a rotational shaker set at 250 rpm for 1 hour. Transformation reactions were plated to LB agar plates containing 120 µg/ml of spectinomycin. The colonies were then replica plated onto LB agar plates containing 5 µg/ml of erythromycin. Colonies that were both spectinomycin and erythromycin resistant were counted the following day to determine transformation efficiency. The chromosomal organization in the ara locus of the transformed TaHy9 *B. licheniformis* strain is shown in FIG. 7. A total of 8 clones showing erythromycin and spectinomycin resistance were tested by PCR using two different primer pairs (33128+33133) and (33129+33132) giving a PCR fragment of 4923 bp and 2358 bp respectively (FIG. 8). All clones were confirmed to be true transformants. The localization of the primers used for the PCR analysis is shown in FIG. 7. These PCR fragments can only be amplified on chromosomal DNA isolated from a correct transformant. This experiment show that we can transform and integrate chromosomal DNA from the *B. subtilis* strain MOL3037 holding to markers directly to the chromosome of *B. licheniformis* strain TaHy9. Results are shown in table 7 below.

Example 16. Transformation Efficiency of a *B. licheniformis* mecA-Disrupted Strain (TaHy9) Using Chromosomal DNA from *B. subtilis* MOL3055

Figure 9:
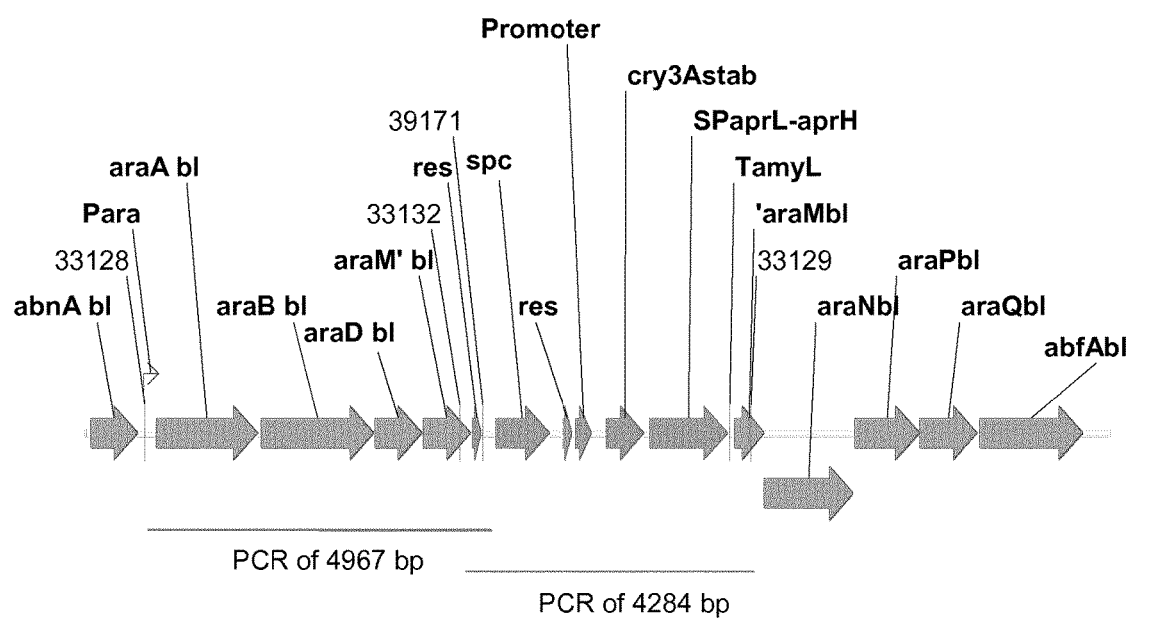
FIG. 9 shows the B. licheniformis TaHy9 transformant from example 16 with positions of genes and primers for PCR verification.

The *B. licheniformis* mecA-disrupted strain TaHy9 from Example 13 was spread onto LB agar plates to obtain confluent growth after incubation at 37° C. overnight. After overnight incubation, approximately 2-3 ml of Spizizen I-xyl medium was added to each plate. Cells were scraped using sterile spreaders and transferred into 15 ml Falcon 2059 tubes. Approximately 500 µl of this culture was used to inoculate 50 ml Spizizen I-xyl medium. Growth was monitored using a Klett densitometer. At each cell density corresponding to Klett unit 140, 160, 180, and 200, 250 µl of the culture plus 250 µl Spizizen II-xyl medium containing 2 mM EGTA was added to a Falcon 2059 tube. One microgram of transforming DNA (*B. subtilis* MOL3055 chromosomal DNA containing a spectinomycin resistance expression cassette and the protease gene aprH integrated at the ara locus; see example 12) was added to each tube. Two microliters of 50 µg/ml spectinomycin was also included in the transformation mix. Tubes were incubated at 37° C. on a rotational shaker set at 250 rpm for 1 hour. Transformation reactions were plated to LB agar plates containing 120 µg/ml of spectinomycin. The colonies were then replica plated onto LB agar plates containing 120 µg/ml of spectinomycin and skim milk. Colonies that were both spectinomycin and protease positive were counted the following day to determine transformation efficiency. The chromosomal organization in the ara locus of the transformed TaHy9 *B. licheniformis* strain is shown in FIG. 9. A total of 8 clones showing spectinomycin resistance and protease phenotype were tested by PCR using two different primer pairs (33128+39171) and (33132 33129) giving a PCR fragment of 4967 bp and 4284 bp respectively (FIG. 10). All clones were confirmed to be true transformants. The localization of the primers used for the PCR analysis is shown in FIG. 9. These PCR fragments can only be amplified on chromosomal DNA isolated from a correct transformant.

This experiment showed that chromosomal DNA from the *B. subtilis* MOL3055 strain, including one marker gene and one protease expression cassette, can be successfully transformed directly into the *B. licheniformis* TaHy9 strain, where the expression cassette and the marker were integrated into the *B. licheniformis* chromosome by double homologous recombination. Results are shown in table 7 below.

TABLE 7

Results from Examples 14-16 showing number of transformants on plates pr 1 µg of chromosomal DNA (Chr DNA) transformed.

| | Competent strain | Chr DNA* MDT232 Example 14 | Chr DNA** MOL3037 Example 15 | Chr DNA*** MOL3055 Example 16 | Water** |
|---|---|---|---|---|---|
| Experiment 1 | TaHy9 | 80 | 12 | — | 0 |
| | SJ1904 | 0 | 0 | — | 0 |
| Experiment 2 | TaHy9 | 300 | 120 | 55 | 0 |
| Experiment 3 | TaHy9 | 150 | 56 | 35 | 0 |

*Selected on plates with spectinomycin;

**Selected on plates with spectinomycin and erythromycin;

***Selected on plates with spectinomycin and screened for protease activity.

The invention claimed is:

1. A method for directly transferring a recombinant polynucleotide of interest from the chromosome of a *Bacillus subtilis* donor cell to the chromosome of a *Bacillus licheniformis* mecA-disrupted recipient cell,
wherein the *Bacillus subtilis* donor cell expresses a *Bacillus licheniformis* DNA methyltransferase, wherein the polynucleotide of interest comprises at least one coding sequence of interest and a selectable marker, wherein said polynucleotide of interest in the chromosome of the *Bacillus subtilis* donor cell is flanked on each side by a polynucleotide region derived from the chromosome of the *Bacillus licheniformis* mecA-disrupted recipient cell, and wherein the flanking polynucleotide regions are of sufficient size and sequence identity to allow double homologous recombination with the corresponding regions in the chromosome of the *Bacillus licheniformis* mecA-disrupted recipient cell; the method comprising the steps of:
a) providing chromosomal DNA from the *Bacillus subtilis* donor cell, said DNA comprising the polynucleotide of interest flanked on each side by a polynucleotide region derived from the chromosome of the *Bacillus licheniformis* mecA-disrupted recipient cell;
b) transforming the *Bacillus licheniformis* mecA-disrupted recipient cell with the DNA from step (a); and
c) selecting a successfully transformed *Bacillus licheniformis* mecA-disrupted recipient cell, wherein the polynucleotide of interest comprising the selectable marker has been integrated into its chromosome.

2. The method of claim 1, wherein the at least one coding sequence of interest encodes a hormone, enzyme, receptor or portion thereof, antibody or portion thereof, or reporter.

3. The method of claim 1, wherein the at least one coding sequence of interest comprises an operon or several genes.

4. The method of claim 1, wherein the flanking polynucleotide regions derived from the chromosome of the *Bacillus licheniformis* mecA-disrupted recipient cell comprise between 100-5,000 nucleotides.

5. The method of claim 4, wherein each flanking polynucleotide region derived from the chromosome of the *Bacillus licheniformis* mecA-disrupted recipient cell is at least 80% identical to the corresponding region in the chromosome of the *Bacillus licheniformis* mecA-disrupted recipient cell.

6. The method of claim 1, wherein the at least one coding sequence of interest comprises a gene library, and wherein said method comprises the additional first steps of:
i) screening the gene library for an encoded activity while it resides in the chromosome of the *Bacillus subtilis* donor cell, and
ii) selecting a *Bacillus subtilis* donor clone of interest, before chromosomal DNA of the clone of interest is provided and transformed into the *Bacillus licheniformis* mecA-disrupted recipient cell in accordance with steps a) c) of claim 1.

7. The method of claim 1, wherein the at least one coding sequence of interest encodes a hydrolase, isomerase, ligase, lyase, oxidoreductase, or transferase.

8. The method of claim 1, wherein the at least one coding sequence of interest encodes an alpha-galactosidase, alpha-glucosidase, aminopeptidase, amylase, asparaginase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, green fluorescent protein, glucano-transferase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or a xylanase.

9. The method of claim 4, wherein each flanking polynucleotide region derived from the chromosome of the *Bacillus licheniformis* mecA-disrupted recipient cell is at least 90% identical to the corresponding region in the chromosome of the *Bacillus licheniformis* mecA-disrupted recipient cell.

* * * * *

SEQUENCE LISTING

<160> NUMBER OF SEQ ID NOS: 51

<210> SEQ ID NO 1
<211> LENGTH: 27
<212> TYPE: DNA
<213> ORGANISM: Artificial sequence
<220> FEATURE:
<223> OTHER INFORMATION: Synthetic construct

<400> SEQUENCE: 1
cactcccgag aggagaagtg ctggctg                                27

<210> SEQ ID NO 2
<211> LENGTH: 50
<212> TYPE: DNA
<213> ORGANISM: Artificial sequence
<220> FEATURE:
<223> OTHER INFORMATION: Synthetic construct

<400> SEQUENCE: 2
cagccagcac ttctcctctc gggagtggga gctgtaatat aaaaaccttc       50

<210> SEQ ID NO 3
<211> LENGTH: 25
<212> TYPE: DNA
<213> ORGANISM: Artificial sequence
<220> FEATURE:
<223> OTHER INFORMATION: Synthetic construct

<400> SEQUENCE: 3
gtcaatcttt tcttttaaaa aaagc                                  25

<210> SEQ ID NO 4
<211> LENGTH: 50
<212> TYPE: DNA
<213> ORGANISM: Artificial sequence
<220> FEATURE:
<223> OTHER INFORMATION: Synthetic construct

<400> SEQUENCE: 4 gctttttta aagaaaaga ttgacgcaaa gacgcatgtg ttttggtttg         50

<210> SEQ ID NO 5
<211> LENGTH: 50
<212> TYPE: DNA
<213> ORGANISM: Artificial sequence
<220> FEATURE:
<223> OTHER INFORMATION: Synthetic construct

<400> SEQUENCE: 5 gctttttta aagaaaaga ttgacaacaa acgaaaattg gataaagtgg         50

<210> SEQ ID NO 6
<211> LENGTH: 23
<212> TYPE: DNA
<213> ORGANISM: Artificial sequence
<220> FEATURE:
<223> OTHER INFORMATION: Synthetic construct

<400> SEQUENCE: 6
cagccgtcca tccttgcaga gtc                                    23

<210> SEQ ID NO 7
<211> LENGTH: 23
<212> TYPE: DNA
<213> ORGANISM: Artificial sequence

```
<220> FEATURE:
<223> OTHER INFORMATION: Synthetic construct

<400> SEQUENCE: 7
gtccagcaga tctcttggaa ggc                                              23

<210> SEQ ID NO 8
<211> LENGTH: 22
<212> TYPE: DNA
<213> ORGANISM: Artificial sequence
<220> FEATURE:
<223> OTHER INFORMATION: Synthetic construct

<400> SEQUENCE: 8
cacgcttctt ttaagtacgg ag                                               22

<210> SEQ ID NO 9
<211> LENGTH: 23
<212> TYPE: DNA
<213> ORGANISM: Artificial sequence
<220> FEATURE:
<223> OTHER INFORMATION: Synthetic construct

<400> SEQUENCE: 9
ccgcttcttc tggtaataga agc                                              23

<210> SEQ ID NO 10
<211> LENGTH: 49
<212> TYPE: DNA
<213> ORGANISM: Artificial sequence
<220> FEATURE:
<223> OTHER INFORMATION: Synthetic construct

<400> SEQUENCE: 10
ctgcaatcgg atgcgattat tgaaggtcaa gacattgatc aagcgcttc                  49

<210> SEQ ID NO 11
<211> LENGTH: 24
<212> TYPE: DNA
<213> ORGANISM: Artificial sequence
<220> FEATURE:
<223> OTHER INFORMATION: Synthetic construct

<400> SEQUENCE: 11
ctgcgcaaaa gacataatcg attc                                             24

<210> SEQ ID NO 12
<211> LENGTH: 24
<212> TYPE: DNA
<213> ORGANISM: Artificial sequence
<220> FEATURE:
<223> OTHER INFORMATION: Synthetic construct

<400> SEQUENCE: 12
ttcaataatc gcatccgatt gcag                                             24

<210> SEQ ID NO 13
<211> LENGTH: 25
<212> TYPE: DNA
<213> ORGANISM: Artificial sequence
<220> FEATURE:
<223> OTHER INFORMATION: Synthetic construct

<400> SEQUENCE: 13
aatgctgctc ggtatgaccc ttgcc                                            25
```

<210> SEQ ID NO 14
<211> LENGTH: 23
<212> TYPE: DNA
<213> ORGANISM: Artificial sequence
<220> FEATURE:
<223> OTHER INFORMATION: Synthetic construct

<400> SEQUENCE: 14
caaacgcagg aggatgcgga gcc                                       23

<210> SEQ ID NO 15
<211> LENGTH: 47
<212> TYPE: DNA
<213> ORGANISM: Artificial sequence
<220> FEATURE:
<223> OTHER INFORMATION: Synthetic construct

<400> SEQUENCE: 15
gaatcgatta tgtcttttgc gcagtttcct ggaatgtgat ccgcctg             47

<210> SEQ ID NO 16
<211> LENGTH: 26
<212> TYPE: DNA
<213> ORGANISM: Artificial sequence
<220> FEATURE:
<223> OTHER INFORMATION: Synthetic construct

<400> SEQUENCE: 16
tgctttcgaa gcattagacg tggatg                                    26

<210> SEQ ID NO 17
<211> LENGTH: 23
<212> TYPE: DNA
<213> ORGANISM: Artificial sequence
<220> FEATURE:
<223> OTHER INFORMATION: Synthetic construct

<400> SEQUENCE: 17
ttcaacactc gttgatgccg atc                                       23

<210> SEQ ID NO 18
<211> LENGTH: 48
<212> TYPE: DNA
<213> ORGANISM: Artificial sequence
<220> FEATURE:
<223> OTHER INFORMATION: Synthetic construct

<400> SEQUENCE: 18
gttttaaaag taagcacctg ttggtgctat aaaattagcc taattgag            48

<210> SEQ ID NO 19
<211> LENGTH: 48
<212> TYPE: DNA
<213> ORGANISM: Artificial sequence
<220> FEATURE:
<223> OTHER INFORMATION: Synthetic construct

<400> SEQUENCE: 19
gacggcaggc tgacggctca ccttctttcc tggaatgtga tccgcctg            48

<210> SEQ ID NO 20
<211> LENGTH: 50
<212> TYPE: DNA
<213> ORGANISM: Artificial sequence
<220> FEATURE:
<223> OTHER INFORMATION: Synthetic construct

<400> SEQUENCE: 20
ccaacaggtg cttactttta aaactacgtc atgctggttc tcgaccattc         50

<210> SEQ ID NO 21
<211> LENGTH: 25
<212> TYPE: DNA
<213> ORGANISM: Artificial sequence
<220> FEATURE:
<223> OTHER INFORMATION: Synthetic construct

<400> SEQUENCE: 21
gaaggtgagc cgtcagcctg ccgtc                                    25

<210> SEQ ID NO 22
<211> LENGTH: 48
<212> TYPE: DNA
<213> ORGANISM: Artificial sequence
<220> FEATURE:
<223> OTHER INFORMATION: Synthetic construct

<400> SEQUENCE: 22
gaatcgatta tgtcttttgc gcagccaatc tagggtaagt aaattgag           48

<210> SEQ ID NO 23
<211> LENGTH: 25
<212> TYPE: DNA
<213> ORGANISM: Artificial sequence
<220> FEATURE:
<223> OTHER INFORMATION: Synthetic construct

<400> SEQUENCE: 23
cataatgata taatgaagtt gttcg                                    25

<210> SEQ ID NO 24
<211> LENGTH: 26
<212> TYPE: DNA
<213> ORGANISM: Artificial sequence
<220> FEATURE:
<223> OTHER INFORMATION: Synthetic construct

<400> SEQUENCE: 24
cgccgatacg cctcatccac tctgcc                                   26

<210> SEQ ID NO 25
<211> LENGTH: 26
<212> TYPE: DNA
<213> ORGANISM: Artificial sequence
<220> FEATURE:
<223> OTHER INFORMATION: Synthetic construct

<400> SEQUENCE: 25
caagcgccgc agaacatggt agccgc                                   26

<210> SEQ ID NO 26
<211> LENGTH: 26
<212> TYPE: DNA
<213> ORGANISM: Artificial sequence
<220> FEATURE:
<223> OTHER INFORMATION: Synthetic construct

<400> SEQUENCE: 26
ggttgataat gaactgtgct gattac                                   26

<210> SEQ ID NO 27

<211> LENGTH: 47
<212> TYPE: DNA
<213> ORGANISM: Artificial sequence
<220> FEATURE:
<223> OTHER INFORMATION: Synthetic construct

<400> SEQUENCE: 27
ggaagcgctt gatcaatgtc ttgactaagt taaggtggat acacatc        47

<210> SEQ ID NO 28
<211> LENGTH: 49
<212> TYPE: DNA
<213> ORGANISM: artificial sequence
<220> FEATURE:
<223> OTHER INFORMATION: Synthetic construct

<400> SEQUENCE: 28
cgcgtggtac ccggggatcc tctagcatgc tggttctcga ccattcaag       49

<210> SEQ ID NO 29
<211> LENGTH: 22
<212> TYPE: DNA
<213> ORGANISM: Artificial sequence
<220> FEATURE:
<223> OTHER INFORMATION: Synthetic construct

<400> SEQUENCE: 29
cgtagacggc aagcccgtat cc                                    22

<210> SEQ ID NO 30
<211> LENGTH: 23
<212> TYPE: DNA
<213> ORGANISM: Artificial sequence
<220> FEATURE:
<223> OTHER INFORMATION: Synthetic construct

<400> SEQUENCE: 30
gtgcagttct cgtcgatgtc cgg                                   23

<210> SEQ ID NO 31
<211> LENGTH: 24
<212> TYPE: DNA
<213> ORGANISM: Artificial sequence
<220> FEATURE:
<223> OTHER INFORMATION: Synthetic construct

<400> SEQUENCE: 31
cagtgaattc tgatcaaatg gttc                                  24

<210> SEQ ID NO 32
<211> LENGTH: 49
<212> TYPE: DNA
<213> ORGANISM: Artificial sequence
<220> FEATURE:
<223> OTHER INFORMATION: Synthetic construct

<400> SEQUENCE: 32
gaaccatttg atcagaattc actggtcaag acattgatca agcgcttcc       49

<210> SEQ ID NO 33
<211> LENGTH: 47
<212> TYPE: DNA
<213> ORGANISM: Artificial sequence
<220> FEATURE:
<223> OTHER INFORMATION: Synthetic construct

<400> SEQUENCE: 33
gatgtgtatc caccttaact tagtcaagac attgatcaag cgcttcc         47

<210> SEQ ID NO 34
<211> LENGTH: 22
<212> TYPE: DNA
<213> ORGANISM: Artificial sequence
<220> FEATURE:
<223> OTHER INFORMATION: Synthetic construct

<400> SEQUENCE: 34
caacgaaatt tataagacgg gc                                    22

<210> SEQ ID NO 35
<211> LENGTH: 45
<212> TYPE: DNA
<213> ORGANISM: Artificial sequence
<220> FEATURE:
<223> OTHER INFORMATION: Synthetic construct

<400> SEQUENCE: 35
gcccgtctta taaatttcgt tgatgctggt tctcgaccat tcaag            45

<210> SEQ ID NO 36
<211> LENGTH: 22
<212> TYPE: DNA
<213> ORGANISM: Artificial sequence
<220> FEATURE:
<223> OTHER INFORMATION: Synthetic construct

<400> SEQUENCE: 36
gaaaacaaga gcgtcagcac gg                                    22

<210> SEQ ID NO 37
<211> LENGTH: 24
<212> TYPE: DNA
<213> ORGANISM: Artificial sequence
<220> FEATURE:
<223> OTHER INFORMATION: Synthetic construct

<400> SEQUENCE: 37
caggtgagga aatcgcgaca gctg                                  24

<210> SEQ ID NO 38
<211> LENGTH: 25
<212> TYPE: DNA
<213> ORGANISM: Artificial sequence
<220> FEATURE:
<223> OTHER INFORMATION: Synthetic construct

<400> SEQUENCE: 38
gttcgggttc ttcaaatatt tctcc                                 25

<210> SEQ ID NO 39
<211> LENGTH: 49
<212> TYPE: DNA
<213> ORGANISM: Artificial sequence
<220> FEATURE:
<223> OTHER INFORMATION: Synthetic construct

<400> SEQUENCE: 39
gaacgttgcg gtacctgatc tagatctcgg gttcttcaaa tatttctcc       49

<210> SEQ ID NO 40
<211> LENGTH: 26
<212> TYPE: DNA

```
<213> ORGANISM: Artificial sequence
<220> FEATURE:
<223> OTHER INFORMATION: Synthetic construct

<400> SEQUENCE: 40
gatctagatc aggtaccgca acgttc                                          26

<210> SEQ ID NO 41
<211> LENGTH: 25
<212> TYPE: DNA
<213> ORGANISM: Artificial sequence
<220> FEATURE:
<223> OTHER INFORMATION: Synthetic construct

<400> SEQUENCE: 41
ctagaggatc cccgggtacc acgcg                                           25

<210> SEQ ID NO 42
<211> LENGTH: 21
<212> TYPE: DNA
<213> ORGANISM: Artificial sequence
<220> FEATURE:
<223> OTHER INFORMATION: Synthetic construct

<400> SEQUENCE: 42
gaattccatt aatagctgct g                                               21

<210> SEQ ID NO 43
<211> LENGTH: 36
<212> TYPE: DNA
<213> ORGANISM: Artificial sequence
<220> FEATURE:
<223> OTHER INFORMATION: Synthetic construct

<400> SEQUENCE: 43
tccatactct ttcagcatgg tcttcgatat caccgt                               36

<210> SEQ ID NO 44
<211> LENGTH: 36
<212> TYPE: DNA
<213> ORGANISM: Artificial sequence
<220> FEATURE:
<223> OTHER INFORMATION: Synthetic construct

<400> SEQUENCE: 44
acggtgatat cgaagaccat gctgaaagag tatgga                               36

<210> SEQ ID NO 45
<211> LENGTH: 23
<212> TYPE: DNA
<213> ORGANISM: Artificial sequence
<220> FEATURE:
<223> OTHER INFORMATION: Synthetic construct

<400> SEQUENCE: 45
ctcgagcgca tcctcccaaa atc                                             23

<210> SEQ ID NO 46
<211> LENGTH: 6927
<212> TYPE: DNA
<213> ORGANISM: Bacillus licheniformis
<220> FEATURE:
<221> NAME/KEY: misc_feature
<222> LOCATION: (1)..(6927)
<223> OTHER INFORMATION: Entire SOE-PCR fragment of Example 1 and shown
      in Figure 1.
<220> FEATURE:
```

```
<221> NAME/KEY: primer_bind
<222> LOCATION: (1)..(22)
<223> OTHER INFORMATION: Primer 24486.
<220> FEATURE:
<221> NAME/KEY: primer_bind
<222> LOCATION: (25)..(47)
<223> OTHER INFORMATION: Primer 24487.
<220> FEATURE:
<221> NAME/KEY: misc_feature
<222> LOCATION: (1961)..(2929)
<223> OTHER INFORMATION: The abnA coding sequence.
<220> FEATURE:
<221> NAME/KEY: primer_bind
<222> LOCATION: (2958)..(2982)
<223> OTHER INFORMATION: Primer 20991 complement.
<220> FEATURE:
<221> NAME/KEY: primer_bind
<222> LOCATION: (2958)..(3007)
<223> OTHER INFORMATION: Primer 23658.
<220> FEATURE:
<221> NAME/KEY: misc_feature
<222> LOCATION: (3136)..(3763)
<223> OTHER INFORMATION: The cat coding sequence.
<220> FEATURE:
<221> NAME/KEY: primer_bind
<222> LOCATION: (3857)..(3906)
<223> OTHER INFORMATION: Primer 20985 complement.
<220> FEATURE:
<221> NAME/KEY: misc_feature
<222> LOCATION: (3880)..(4070)
<223> OTHER INFORMATION: The araM coding sequence.
<220> FEATURE:
<221> NAME/KEY: primer_bind
<222> LOCATION: (3880)..(3906)
<223> OTHER INFORMATION: Primer 20984.
<220> FEATURE:
<221> NAME/KEY: primer_bind
<222> LOCATION: (3905)..(6927)
<223> OTHER INFORMATION: Primer 24484.
<220> FEATURE:
<221> NAME/KEY: misc_feature
<222> LOCATION: (4104)..(5402)
<223> OTHER INFORMATION: The araN coding sequence.
<220> FEATURE:
<221> NAME/KEY: misc_feature
<222> LOCATION: (5441)..(6379)
<223> OTHER INFORMATION: The araP coding sequence.
<220> FEATURE:
<221> NAME/KEY: misc_feature
<222> LOCATION: (6383)..(6927)
<223> OTHER INFORMATION: The araQ coding sequence.
<220> FEATURE:
<221> NAME/KEY: primer_bind
<222> LOCATION: (6885)..(6907)
<223> OTHER INFORMATION: Primer 24485 complement.

<400> SEQUENCE: 46
cacgcttctt ttaagtacgg agtaccgctt cttctggtaa tagaagcgat tctcatcgct      60
atttactaca gcccgtttga tttataaaaa gcagaaaagc gtttaacgct cttctgcttt     120
ttttgcgagt ttaatgggct ggtcccagtc aatcttacaa tttggatatc gttccagcac     180
tttttcttca atgttctcaa aatcttttgc agagaaatgt ttcagcttct caggagattc     240
tgtccagaca aagatcgtgt gaataaacag cggatgatcc ttggaaggaa tatgcttttc     300
tccctcaaaa agcacgcctt tatacgtcag ctgaaaattc ttccgggtat tgttttgttc     360
atcaataata taaaaatgtt cttttgattg ggccagctta agccttctct taggattcgc     420
gacatatttg accacggcat aaatacaata agcaaaaagt gcaagcaaaa taatccttag     480
aaccatgaca acattgtgt gaaggcacct cccttatggt gatgatctga tgtaatacga     540
aaagcataga aaaaggtttc acttttttcta aagaaaagct gtaaaaacat atacccgatt     600
ttcaagtgaa atagtcgtat ggttagcgcc atgttttgta taataagaat gcaggactga     660
```

```
tgaaggaggg tttggaacat ggcaaaatta gatgaaacat tgaccatgct gaaagattta      720
acagatgcaa aaggcatacc gggcaatgaa agagaagtaa ggcaagtgat gaaatcatac      780
atagaaccat ttgctgatga ggtgacaaca gatcgcctgg gcagtttaat tgcaaaaaaa      840
actggtgcag aaaacggccc gaaaattatg atcgccggac atttggatga agtcggcttt      900
atggtgacac aaatcacaga taaaggcttt atccgttttc aaaccgttgg cggctggtgg      960
gctcaggtta tgcttgctca gcgcgtcacc attgtcacaa aaaaggaga atcacaggg      1020 gttatcggat ctaagccgcc tcatattttg tctcctgaag caagaaaaaa atcagtggaa     1080
ataaaagaca tgtttattga tattggagct tcaagccggg aagaagcctt ggagtggggt     1140
gtacttccgg agatatgat cgttccgcat tttgaattta cggtcatgaa caatgaaaaa      1200
ttcctactcg caaaggcctg gacaaccgc atcggctgtg cgattgctat tgatgtgtta      1260
agaaacttac aaaacacaga tcatccaaat atagtgtatg gcgtcggaac cgtgcaggag     1320
gaagtcgggc tgaggggagc gaaaacggct gcacacacca ttcagcctga tattgcgttt     1380
ggtgttgatg tagggatagc aggagacacg cctggcattt ccgagaagga agcgcagagc     1440
aaaatgggca aaggcccgca gattatcgtt tacgatgcat ccatggtctc tcacaaaggt     1500
ttgcgcgatg cagttgtagc cactgcggag gaagccggca ttccgtacca atttgatgcc     1560
attgccggcg gcgaactga ttcgggtgcc atccatttga cggcaaatgg cgttcctgcg      1620
ctgtccatta ccattgcaac ccgctacatt catacgcacg cggccatgct gcatcgtgat     1680
gattatgaaa acgcggtaaa gttaattaca gaagtcatta gaagttaga ccgaaaaacg      1740 gttgacgaaa ttacgtacca ataaagatac ggaagaatcc gcctattgag gtggattcta     1800 ttttttttgtc tgtacaaatt acagcatagt gactacaata aagggatac cgaaaatttc     1860 ctgaacatga cgatatacga tacgcagtcg atttgacagg aagggaggat aaataatcta     1920
atttgtaagc gctttctaaa ataaggagg ttgaacaaaa ttgaaaaga aaaaaacatg      1980 gaaacgcttc ttacacttttt cgagtgcagc tctggctgca ggtttgatat tcacttctgc     2040
tgctcccgca gaggcagcgt tttggggtgc atccaatgag ctgcttcatg acccgactat     2100
gattaaagag gggagctcat ggtatgcgct cggaacaggg cttactgaag aacggggact     2160
gcgggttttg aagtcttcag acgctaaaaa ttggaccgta caaaaatcca ttttcactac     2220
accgctatcg tggtggtcca attatgtgcc gaattatggc caaaccagt gggcgccgga      2280 catccaatac tataacggca agtactggct atattattcc gtttcttctt ttggaagcaa     2340
tacatctgcc attggcctgg catcttcaac aagcatcagt tcgggggct ggaaggacga      2400 gggcttggtg atccgttcga caagctcaaa taattataac gccattgatc cggagctgac     2460
attcgataag gatggcaacc cgtggcttgc attcggctcg ttttggagcg gcattaagct     2520
gactaagctc gataagagta caatgaagcc tacaggctcg ctctattcga ttgcagctag     2580
accgaataat ggaggtgcct tagaagctcc tactcttacg tatcaaaatg gatattacta     2640
tttaatggtt tcatttgata aatgctgtga cggggtaaac agtacgtaca aaattgctta     2700
cggaagatcc aaaagcatta caggcccctta tcttgataaa agcggaaaaa gcatgcttga     2760
aggcggaggc accattttgg attcgggcaa tgaccaatgg aaaggacctg gaggccagga     2820
tattgtgaac ggaaacattc ttgttcgcca tgcctatgat gccaatgaca acggcattcc     2880
aaagcttctc atcaatgatt tgaattggag ctcgggctgg ccgtcctatt gaattaaaaa     2940
gccgggctct gcccccggct tttttttaaaa gaaaagattg acaacaaacg aaaattggat     3000
```

```
aaagtgggat attttttaaaa tatatattta tgttacagta atattgactt ttaaaaaagg    3060
attgattcta atgaagaaag cagacaagta agcctcctaa attcacttta gataaaaatt    3120
taggaggcat atcaaatgaa ctttaataaa attgatttag acaattggaa gagaaaagag    3180
atatttaatc attatttgaa ccaacaaacg acttttagta taaccacaga aattgatatt    3240
agtgttttat accgaaacat aaaacaagaa ggatataaat tttaccctgc atttattttc    3300
ttagtgacaa gggtgataaa ctcaaataca gcttttagaa ctggttacaa tagcgacgga    3360
gagttaggtt attgggataa gttagagcca ctttatacaa ttttttgatgg tgtatctaaa    3420 acattctctg gtatttggac tcctgtaaag aatgacttca aagagtttta tgatttatac    3480 cttctctgatg tagagaaata taatggttcg gggaaattgt ttcccaaaac acctataccct   3540 gaaaatgctt tttctctttc tattattcca tggacttcat ttactgggtt taacttaaat    3600
atcaataata atagtaatta ccttctaccc attattacag caggaaaatt cattaataaa    3660
ggtaattcaa tatatttacc gctatcttta caggtacatc attctgtttg tgatggttat    3720
catgcaggat tgtttatgaa ctctattcag gaattgtcag ataggcctaa tgactggctt    3780
ttataatatg agataatgcc gactgtactt tttacagtcg gttttctaat gtcactaacc    3840
tgccccgtta gttgaagaag gttttttatat tacagctccc actcccgaga ggagaagtgc    3900
tggctgattg gctgagatca gccggaggcc ctgcgtattt tgacgaaatc ggtgtcgggc    3960
aggattccgt caaaaatgcc ttcagacacg cgcacacctt aagagaccga tgcaccggat    4020
taagaatcat caatgaaaac aaaacgctga tcaaccatgg tctatatgaa tagcccgcac    4080
ctcgaatgga aggggtaacg cagatgaaaa aaatgactgt ctgttttctt gtgctcatga    4140
tgttgctgac attagtcatt gccgggtgtt cagcagaaaa atcatccggc aaatcgggtg    4200
aaactgagct gaccttttgg acatttaacg ggcttcatga gcagttctat gtggaaatgg    4260
tgaaggaatg gaacaaaaaa tatcctgacc gcaaaattaa gctgaatacg tcgtttatc     4320 catatggaca aatgcacgat aacttatcta tctcccctaat agcgggagaa ggcgttcctg    4380
atattgcaga tgtcgaattg gcccgttttt caaactttt gaagggctct gacataccgc     4440
ttgccgactt gactccgctg attgaaaagg atcgcgataa attcgttgag gcgcggctga    4500
cattgtacag caaaaacgga aagctttacg gactcgatac acatgtaggg acaacggtca    4560
tgttttataa catggatgtg atgaaaaaag ccggcgtcaa tcctgacgat attaaaacat    4620
gggatgatta ccataaagcc ggacagaaag tgcgcaaagt gaccgggaag ccgatgggaa    4680
cggtggaaac aaatgattcc gcaacgttct tatctctgat ttcacagcaa aactcaggct    4740
attttgataa aaacggcaag ctgatcctca ataatgacac caacgtaaaa acacttcaat    4800
atttaaaaga catgatcaat gataaaacga tgattcctgc gccgggcggc gggcatcaca    4860
gtgaagaata ctacggcttt atgaaccaag gaggagctgc ttcagttctc atgccgattt    4920
ggtatatggg aagatttatc gattatatgc ctgatctgaa agggaagatt gccatcagac    4980
cgctcccggc atggaaagag ggggcgacc gctcggcagg tttgggcggt acggcaactg     5040
ttgtaccgaa gcaatccaag catgttgagt tagcaaaaga gttttttggcc tttgcgaagg    5100 gctctgaaga aggaaataaa aaactctgga gcgtactcgg ctttgacccg cttcgctggg    5160
atgtttggag ctccaaggaa ttgaaagaga aaaacaaata cacggattac ttccaaaacg    5220
gaacaggcat ttttttctgtg ctgctcgata tcaaggatga aatcaatcca atttatttac    5280
atgaggattt tgccaaggct tcagaccttg tcaacgaaag cgtattgttc gacgcgctta    5340
aatctcagca aaaaacgcct aaacaagcct tggacagagc ggcaggtgaa ctgaaacaga    5400
```

-continued

```
aatagaatcc cattcaaaaa gtgaaagcgg ggaggttctc atgaaacctg tgaaaacggg    5460
aacggttcat cccgttcctt cagctgcgaa acaatcaggc tggcgagatc tgttttattc    5520
aaaaaaagcg gcgccctatc tgtttacagc gccattcgtt ttatcctttc tcgtattttt    5580
tctatacccc atcattagtg tcttcatcat gagcttccaa agaattttgc cgggagaggt    5640
gtcctttgtc ggattgtcta attatacagc gctaaacaac ccgacgttct ataccgccct    5700
ttggaatacg ctggaataca cctttttggac gctgatcgtg ctgattcctg ttccattgct    5760
tctggccata ttcctgaatt caaagctggt caaatttaga aatatattta aatcagcatt    5820
atttatcccg gcattgacct caaccattgt cgcggggatc attttcggc tgatcttcgg     5880 agaaatggaa acgtctctgg ccaattccat cctacttaaa ctcggctttt cacctcagaa    5940
ctggatgaac aatgaacata ccggcatgtt tttgatggtg ctgcttgctt catggagatg    6000
gatgggaatc aacatccttt acttttagc aggtttgcaa aatgtgccga aagagctgta    6060
cgaagccgct gatatagacg gcgcgaatac aatgaaaaaa tttctgcaca tcacgctgcc    6120
gtttctcaag cctgtaaccg tatatgtgct gaccatcagc atcatcggcg gcttcaggat    6180
gtttgaggaa agctacgtcc tttggcagaa taattccccg ggtaatattg gtctgacgct    6240
tgtcggatat ttgtatcagc agggacttgc ctacaatgaa atgggatacg gagcggccat    6300
cggcattgtg cttttgattg tgatccttgt tgtcagcctg atttcattaa agctgtcagg    6360
ctcgtttaag ggggagggat aaatgttgcg gcacagtcct cagtttagcg tttatagaat    6420
tgcgctgacc ctgttttta tgatgctgag cctattgtat ctttttccga ttttctgttt     6480
gcttttagga tcattaaagc cgtcatctga gcttttgcgt gtggggctga atcttgatat    6540
tgatccaaaa gtgatgagtt tgataacta cacatttctg tttaatggcg gcagcattta    6600
tttcaaatgg ttttttaaca gtcttgtact cggactttt acgactgtgc tcactctgtt     6660
tttttcttcg atgatcgggt acgggcttgc ggtttatgat tttaagggca gaaatatcat    6720
ctttgttctt gtgctgatta ttatgatggt tccgctggaa gtgatgatgc ttcctctgtt    6780
taaacttact gtcggactgc acttgatcga ttcatatacg ggtgtcatat tgccgtttat    6840
cgtttcacct gttgctgttt tctttttcag gcaatatgct cttggccttc caagagatct    6900
gctggactct gcaaggatgg acggctg                                        6927
```

<210> SEQ ID NO 47
<211> LENGTH: 11613
<212> TYPE: DNA
<213> ORGANISM: Bacillus licheniformis
<220> FEATURE:
<221> NAME/KEY: primer_bind
<222> LOCATION: (1)..(22)
<223> OTHER INFORMATION: Primer 24487
<220> FEATURE:
<221> NAME/KEY: primer_bind
<222> LOCATION: (25)..(47)
<223> OTHER INFORMATION: Primer 24487
<220> FEATURE:
<221> NAME/KEY: misc_feature
<222> LOCATION: (1961)..(2929)
<223> OTHER INFORMATION: The abnA gene.
<220> FEATURE:
<221> NAME/KEY: primer_bind
<222> LOCATION: (2958)..(2982)
<223> OTHER INFORMATION: Primer 20990 complement.
<220> FEATURE:
<221> NAME/KEY: primer_bind
<222> LOCATION: (2958)..(3007)
<223> OTHER INFORMATION: Primer 20991
<220> FEATURE:

```
<221> NAME/KEY: misc_feature
<222> LOCATION: (2983)..(4452)
<223> OTHER INFORMATION: The araA gene.
<220> FEATURE:
<221> NAME/KEY: misc_feature
<222> LOCATION: (4503)..(6158)
<223> OTHER INFORMATION: The araB gene.
<220> FEATURE:
<221> NAME/KEY: misc_feature
<222> LOCATION: (6177)..(6860)
<223> OTHER INFORMATION: The araD gene.
<220> FEATURE:
<221> NAME/KEY: misc_feature
<222> LOCATION: (6880)..(7572)
<223> OTHER INFORMATION: The araM gene.
<220> FEATURE:
<221> NAME/KEY: primer_bind
<222> LOCATION: (7549)..(7597)
<223> OTHER INFORMATION: Primer 27094 complement.
<220> FEATURE:
<221> NAME/KEY: primer_bind
<222> LOCATION: (7574)..(7597)
<223> OTHER INFORMATION: Primer 27096.
<220> FEATURE:
<221> NAME/KEY: misc_feature
<222> LOCATION: (7800)..(8531)
<223> OTHER INFORMATION: The erm gene.
<220> FEATURE:
<221> NAME/KEY: primer_bind
<222> LOCATION: (8592)..(8638)
<223> OTHER INFORMATION: Primer 30009
<220> FEATURE:
<221> NAME/KEY: primer_bind
<222> LOCATION: (8592)..(8615)
<223> OTHER INFORMATION: Primer 27095 complement.
<220> FEATURE:
<221> NAME/KEY: primer_bind
<222> LOCATION: (11556)..(11578)
<223> OTHER INFORMATION: Primer 30008 complement
<220> FEATURE:
<221> NAME/KEY: primer_bind
<222> LOCATION: (11588)..(11613)
<223> OTHER INFORMATION: Primer 30011 complement

<400> SEQUENCE: 47
cacgcttctt ttaagtacgg agtaccgctt cttctggtaa tagaagcgat tctcatcgct      60
atttactaca gcccgtttga tttataaaaa gcagaaaagc gtttaacgct cttctgcttt     120
ttttgcgagt ttaatgggct ggtcccagtc aatcttacaa tttggatatc gttccagcac     180 ttttttcttca atgttctcaa aatcttttgc agagaaatgt ttcagcttct caggagattc     240
tgtccagaca aagatcgtgt gaataaacag cggatgatcc ttggaaggaa tatgcttttc     300
tccctcaaaa agcacgcctt tatacgtcag ctgaaaattc ttccgggtat tgttttgttc     360
atcaataata taaaaatgtt cttttgattg ggccagctta agccttctct taggattcgc     420
gacatatttg accacggcat aaatacaata agcaaaagt gcaagcaaaa taatccttag      480
aaccatgaca acattgtgt gaaggcacct cccttatggt gatgatctga tgtaatacga      540
aaagcataga aaaggtttc acttttcta aagaaagct gtaaaaacat atacccgatt        600
ttcaagtgaa atagtcgtat ggttagcgcc atgttttgta taataagaat gcaggactga    660
tgaaggaggg tttggaacat ggcaaaatta gatgaaacat tgaccatgct gaaagattta    720
acagatgcaa aaggcatacc gggcaatgaa agagaagtaa ggcaagtgat gaaatcatac    780
atagaaccat ttgctgatga ggtgacaaca gatcgcctgg gcagtttaat tgcaaaaaaa    840
actggtgcag aaaacggccc gaaaattatg atcgccggac atttggatga agtcggcttt    900
atggtgcaca aaatcacaga taaggctttt atccgttttc aaaccgttgg cggctggtgg    960
gctcaggtta tgcttgctca gcgcgtcacc attgtcacaa aaaaggaga aatcacaggg    1020
```

```
gttatcggat ctaagccgcc tcatattttg tctcctgaag caagaaaaaa atcagtggaa    1080
ataaaagaca tgtttattga tattggagct tcaagccggg aagaagcctt ggagtggggt    1140
gtacttccgg gagatatgat cgttccgcat tttgaattta cggtcatgaa caatgaaaaa    1200
ttcctactcg caaaggcctg gacaaccgc atcggctgtg cgattgctat tgatgtgtta    1260
agaaacttac aaaacacaga tcatccaaat atagtgtatg cgtcggaac cgtgcaggag    1320 gaagtcgggc tgaggggagc gaaaacggct gcacacacca ttcagcctga tattgcgttt    1380
ggtgttgatg tagggatagc aggagacacg cctggcattt ccgagaagga agcgcagagc    1440
aaaatgggca aaggcccgca gattatcgtt tacgatgcat ccatggtctc tcacaaaggt    1500
ttgcgcgatg cagttgtagc cactgcggag gaagccggca ttccgtacca atttgatgcc    1560
attgccggcg gcggaactga ttcgggtgcc atccatttga cggcaaatgg cgttcctgcg    1620
ctgtccatta ccattgcaac ccgctacatt catacgcacg cggccatgct gcatcgtgat    1680
gattatgaaa acgcggtaaa gttaattaca gaagtcatta agaagttaga ccgaaaaacg    1740
gttgacgaaa ttacgtacca ataaagatac ggaagaatcc gcctattgag gtggattcta    1800 ttttttttgtc tgtacaaatt acagcatagt gactacaata aaggggatac cgaaaatttc    1860
ctgaacatga cgatatacga tacgcagtcg atttgacagg aagggaggat aaataatcta    1920
atttgtaagc gctttctaaa ataaggagg ttgaacaaaa ttgaaaaaga aaaaacatg    1980 gaaacgcttc ttacactttt cgagtgcagc tctggctgca ggtttgatat tcacttctgc    2040
tgctcccgca gaggcagcgt tttggggtgc atccaatgag ctgcttcatg acccgactat    2100
gattaaagag gggagctcat ggtatgcgct cggaacaggg cttactgaag aacggggact    2160
gcgggttttg aagtcttcag acgctaaaaa ttggaccgta caaaaatcca ttttcactac    2220
accgctatcg tggtggtcca attatgtgcc gaattatggc caaaaccagt gggcgccgga    2280
catccaatac tataacggca agtactggct atattattcc gtttcttctt ttggaagcaa    2340
tacatctgcc attggcctgg catcttcaac aagcatcagt tcgggggct ggaaggacga    2400 gggcttggtg atccgttcga caagctcaaa taattataac gccattgatc cggagctgac    2460
attcgataag gatggcaacc cgtggcttgc attcggctcg ttttggagcg gcattaagct    2520
gactaagctc gataagagta caatgaagcc tacaggctcg ctctattcga ttgcagctag    2580
accgaataat ggaggtgcct tagaagctcc tactcttacg tatcaaaatg gatattacta    2640
tttaatggtt tcatttgata aatgctgtga cggggtaaac agtacgtaca aaattgctta    2700
cggaagatcc aaaagcatta caggcccta tcttgataaa agcggaaaaa gcatgcttga    2760
aggcggaggc accatttggg attcgggcaa tgaccaatgg aaaggacctg gaggccagga    2820
tattgtgaac ggaaacattc ttgttcgcca tgcctatgat gccaatgaca acggcattcc    2880
aaagcttctc atcaatgatt tgaattggag ctcgggctgg ccgtcctatt gaattaaaaa    2940
gccgggctct gccccggct ttttaaaa gaaaagattg acgcaaagac gcatgtgttt    3000
tggtttgtga caggcagcca gcatttatat ggcgaagagg cggtacaaga ggtagaagag    3060
cattccaaaa tgatctgcaa cggattaaat gacggagatt taaggtttca agtcgagtac    3120
aaagcggtgg ccacttcgct ggacggcgtc agaaaactgt ttgaagaggc gaaccgggac    3180
gatgagtgcg caggcatcat cacctggatg catacgtttt caccggccaa aatgtggatt    3240
cccgcccttt ccgagctgaa taagccgctg ctccattttc atacccagtt taaccgggac    3300
attccgtggg ataaaatcga catggatttc atgaatatta atcagtctgc ccacggcgac    3360
```

```
cgcgaatacg gttttatcgg agcgagattg ggcattcctc gaaaagtaat cgccggatat    3420
tgggaagaca gagaagtaaa gcgctcgatc gacaaatgga tgagcgcagc ggtcgcatat    3480
attgaaagcc gccatatcaa agtcgcccga tttggggaca acatgcggaa tgtggcggta    3540
acagaaggag ataagattga agcgcagatt cagcttggct ggtctgtcga cggatatgga    3600
atcggcgatc tcgtcacgga gatcaatgct gtatcagaac agagtctaag cgagctcatc    3660
tccgaatatg aggagcttta tgagtggccg gaaggcgaag cggcaaggga atccgtcaag    3720
gagcaggcgc ggattgagct tggattaaag cgctttcttt cgagcggagg ctatacggcc    3780
tttacgacaa cctttgaaga cctccacggc atgaagcagc ttccgggttt ggctgttcag    3840
cggctgatgg ctgaaggcta tggcttcgga ggagaaggag attggaaaac ggctgcgctt    3900
gtcaggatga tgaaaatgat ggccggcgga aaagaaacgt catttatgga ggattacacg    3960
taccattttg aaccgggcaa tgaaatgatc ctcggctccc acatgcttga agtgtgccct    4020
tcgattgccg aacacaaacc gagaattgaa gtccatccgc tgtcaatggg tgcaaaggat    4080
gatccggcgc ggctcgtgtt tgacggaatt gcaggtcctg cggtcaatgt ctcccttatt    4140
gatttgggcg acgtttcag gcttgtcatc aatgaagtgg gagctgtgaa ggttccgcat    4200
gatatgccga atcttccggt ggcgcgcgta ctttggaagc ctcagccgtc tctgagaaca    4260
tcggctgaag cgtggatttt ggctggcggt gctcaccata catgcctttc gtaccagctg    4320
acagccgagc agatgctcga ttgggccgaa atgtcgggca ttgaagcggt gttgatcaat    4380
cgtgatacaa cgattttaaa tcttcgcaat gaactcaaat ggagtgaagc tgcatatcgg    4440
cttcgcaagt tttaaggggg tgaggactta tcccttacac aatcggagtt gactttggaa    4500
cattgtcagg gcgtgcagtt ctcgtcgatg tccggacagg tgaggaaatc gcgacagctg    4560
tcaaagagta cacgcacggg gtgatagacc gggagcttcc ggtctcaaag cgaaagcttc    4620
cgagagactg ggcgctccag catccggccg attacattga agtgctggag gaaacgattc    4680
cgagcctttt gaaacagtca aaagcggatc cgaaagaaat catcggaatc ggaatcgatt    4740
tcacggcttg cacgattttg cccgttgacg agaacgggac tcctctttgt atgagggaag    4800
agtatgcgtc agaaccgcac agctatgtga agctttggaa gcaccatgct gcacaggagc    4860
aggcgaatcg cttaaatcaa atcgcggaag aaagaaatga acctttttctt caaacatacg    4920
gcgggaaaat tcttccgag tggctcgttc caaagtgat gcaaatcgcg aagaagcgc    4980
ctgacattta tgatgccgca gccgagatca tggaagcggc cgactggatc gtctatatgc    5040
tgtgcggaac cagaaagcgc aacaattgca cagcgggtta taaagcgatt tggaacaata    5100
agagcggcta tccttccgac gatttcttcg caagcctgca tccgaagctg aaaaatatcg    5160
ttcgggaaaa actaacggag gatatttatt ctgtaggcga aaaagcgggc ggactgactg    5220
aagaaatggc cgggaagaca gggcttctgg caggtacggc ggtcgctgtc gcaaatgttg    5280
atgctcatgt gtcggttccg gcggtcggca tcacagagcc gggcaagatg ctgatgatca    5340
tgggaacgtc tacctgtcac atgctgctcg gcgaggatgt caggatggtg ccgggaatgt    5400
gcggcgtcgt tgaagacggg attctgccgg gctatgtcgg ctatgaagcg ggccaatcgt    5460
gcgttggcga ccatttttcat tggctgattc aacactttgt tccagaagcg tatttgaaag    5520
aagctgaagc cgaagggatt tccatttacg aactgctgtc tcaaaaggcc ggcagtctcc    5580
aaatcggtga aagcggtttg cttgcattgg attggtggaa cggaaaccgt tcaacactcg    5640
ttgatgccga tctgacggga atgctgctcg gtatgaccct tgccactaag cctgaagaga    5700
tataccgtgc attggttgaa gcgactgcct gcgggacgag gatcattatt gaaacgttca    5760
```

```
gacaaagcgg cgtgccgatc gaggagctgt atgccgcagg aggaatcgcc gaaaaaaatc    5820
cgtttatcat gcaggtttac gcggatgtca ccaacatgga aatcaaaatt tccggatctc    5880
cgcaggcgcc ggctttaggt tcagcgatat tcggagcgct cgcggccgga agcatgaacg    5940
gcggttacga ccatatcgaa gaagcagtcg cacatatggg caagatcaag gataaaacgt    6000
acaaaccaat tcctgaaaac gtttccttat acgatcagct ttatgcggaa tataaggagc    6060
tttacacgta cttcggaaag caaacaatg tgatgaaacg ccttaaaaaa ttgaaaaaca    6120
tccagtccct tagttctgac cccggtaaag cgatggctta gagggaggag aaaactgtgc    6180
tggaatcttt gaaagaacaa gtattaaaag cgaatttgca gcttgaagaa taccggcttg    6240
tcacctttac atggggaaat gtcagcggta ttgaccggga gaataagctg gtcgtcatca    6300
agccgagcgg tgtcaaatac agcgatttga aagccgaaga tttagtggtt ctgaatatgg    6360
acggcgagat tgtggaaggg gatctgaagc catcttccga tacgccgaca cacctctatc    6420
tttaccggca gtttcaatcg atcggcggga tcgtccatac gcattcccg tgggcgacaa    6480 gctgggctca gtcagggaag gacattccgt cgctcggaac gactcatgcc gactactacc    6540
acggcgacat tccgtgtaca cgggaaatgg atcccgatga aatcaggagt caatacgagc    6600
tgaatacagg aaaagtgatt gtagagacgt tccggcatct tgaccccctg gcggtgcccg    6660
ccgttctcgt gaacaatcac gggccgtttt gctggggaaa agacgcctta actgccgtac    6720
acaatgccgt cgtcctggaa gaagtcgcca agatggcgta ccgctccctg atgctgaatc    6780
cgtctcttaa gcggattaag agcgctttgc aggataagca ttattttcga agcacgggg    6840 cagacgccta ttacggccaa tagaggaggg aagctgccaa tgaatgactt gatctcttat    6900
gtgaaaaaaa ctttgggcgc atgcgaatgc ggaaccgtcc accacccgct tacagtcgaa    6960
aaaatcgcga tcggcgacaa tgctgttgag caagagctgc ccgctttcgt gaaatcggct    7020
tcctataaaa aagccgctgt catttatgat gaaacgaccg gacggttagc cggcaagcgg    7080
attgcctctc ttcttgagga aacggctgaa acggttccgg tgctgctgga agctaatgaa    7140
gcgggcgatg tgacggcgga tgagcaaaca ttggtgagtg cattgatcgg tgtaccgatt    7200
gatgcggatg tactaattgc ggccggagcg ggcacgattc acgacatcgt caggttttgc    7260
gcctatcagc gcggcattcc gtttatttca gttcctacgg ctccgtcggt tgacggtttt    7320
acttcagccg gcgcaccgct gattttaaaa ggaaagaaac agacggttca aacgacagcg    7380
ccgatcgcgc tttttgccga tttggagctc ttgtgtcaag cgccgcagaa catggtagcc    7440
gcaggttttg gcgatatgct cggcaaggtg acgtcgcttg cggattggga gatttcccgc    7500
ttgcttgccg gcgagccgta ttgtccggcc gccagccggc tcacgaggga agcgcttgat    7560
caatgtcttg accttcaata atcgcatccg attgcagtat aaatttaacg atcactcatc    7620
atgttcatat ttatcagagc tcgtgctata attatactaa ttttataagg aggaaaaaat    7680
atgggcattt ttagtatttt tgtaatcagc acagttcatt atcaaccaaa caaaaaataa    7740
gtggttataa tgaatcgtta ataagcaaaa ttcatataac caaattaaag agggttataa    7800
tgaacgagaa aaatataaaa cacagtcaaa actttattac ttcaaaacat aatatagata    7860
aaataatgac aaatataaga ttaaatgaac atgataatat ctttgaaatc ggctcaggaa    7920
aaggccattt taccccttgaa ttagtaaaga ggtgtaattt cgtaactgcc attgaaatag    7980
accataaatt atgcaaaact acagaaaata aacttgttga tcacgataat ttccaagttt    8040
taaacaagga tatattgcag tttaaatttc ctaaaaacca atcctataaa atatatggta    8100
```

```
atataccctta taacataagt acggatataa tacgcaaaat tgttttttgat agtatagcta   8160
atgagattta tttaatcgtg gaatacgggt ttgctaaaag attattaaat acaaaacgct   8220
cattggcatt acttttaatg gcagaagttg atatttctat attaagtatg gttccaagag   8280
aatattttca tcctaaacct aaagtgaata gctcacttat cagattaagt agaaaaaaat   8340
caagaatatc acacaaagat aaacaaaagt ataattattt cgttatgaaa tgggttaaca   8400
aagaatacaa gaaaatattt acaaaaaatc aatttaacaa ttccttaaaa catgcaggaa   8460
ttgacgattt aaacaatatt agctttgaac aattcttatc tcttttcaat agctataaat   8520
tatttaataa gtaagttaag ggatgcataa actgcatccc ttaacttgtt tttcgtgtgc   8580
ctatttttg tgaatcgatt atgtcttttg cgcagtttcc tggaatgtga tccgcctgaa   8640
aaaacagtca taagaatagc aaagccggag atttctctcc ggcttgtctt tcaactgcca   8700
cgagccggcc cattccagcc ggcttttgt ataggaaaaa atgaccgctt ttcaccatga   8760
aattatgata tatttatgaa aaacagaaaa ggggatggga gaaatgaat gcggttacaa   8820
ttgtgatagc atcaatgtgt attttggcta ttgcctatcg tttatacgga acatttatga   8880
tggtgaaggt tctcaaagtg aatgatgaca agccaacacc tgctcatgcg cttgaggatg   8940
ggaaagacta tgtgcctaca aataaatggg tttcgttcgg ccaccacttt gccgcgatcg   9000
cagcggccgg gccgctggtc ggaccaattc tggcggcgca gtttggctat ttgccgggat   9060
tattgtggct gttaatcggg gcggtaattg ggggagccgt ccatgatatt gtggtgttgt   9120
ttgcatcgat gcgcaaaaac ggaaaatcgc tgtcggaagt ggcgaaggat gagcttggcc   9180
ctgttgcagg attttgtaca ggactgtcca tgctgtttat catcacgatc acaatggcgg   9240
gcctgtcgat ggttgtcttg catgcgcttg aacgtaatcc atggggaaca tttgcggtgg   9300
ggattacgat tccgattgcg atgggtgtgg gcttatttta aagaaaacg ggaaatttaa   9360
agctcgcttc aacggtcggc tttctctttt taatggcagg agtctttatc ggtccatggg   9420
tacagactac cgcgctcggt gacttttaa cgctagatac gaaaacgctt gcaatcgcgc   9480
ttcctgttta tgcgttttt gcggctgcgc ttcccgtttg gctgcttctg ctccgcgtg   9540
attatttaag cagcttatg aaaatcggtg tttttatcgc tttgattgtt ggtgtgtttg   9600
tcgtcaatcc gtccattccg ttccctgcgt ttacagaatt cgtaaaaggc ggagggccgg   9660
tgctggcagg acctgtctgg ccgttcatct caataaccat cgcctgcggg gcgatctctg   9720
ggttccatgc ctttgtcggc tcaggaacga caccgaaaat gctgaataaa tggagtgata   9780
tgaagccggt tgcgtttggc gcaatgcttg ttgagtgtct tgtcggtatc atggcgctga   9840
ttgcagcgac cgctttacag cctgctgatt actttgcgat taacagcacg cctgaggttt   9900
tccgtacgct tggcatgaat gtcgtacatt tgcctgaatt gagcgggaa atcggtttgg   9960
acttagaagg aagaacaggg ggagccgtca cgcttgcggt agggatgact tatattttta  10020
ccggaatgcc gtttttcagc catttggcct catacttttt ccaatttgtc attatgtttg  10080
aagcggtctt tattttaaca gcgattgacg ccggcacacg tgtcgcccgt tatttgatcc  10140
aggacttctt cggggaggtg tataagccgc tgaagaaaac agactggatt ccgggctctg  10200
tatttgccag cgcgcttgcc tgtttgatgt ggggtactt gctgtattca ggagatatcg  10260
gttccatttg ggcgctcttc ggcgtttcta atcagctgat ggcttcagtg gggctgatta  10320
tcggagcgac gatcgtgctg aaaatcgccg ataaacgccg gtacattctg acttgcctta  10380
tcccgcttgc ctatttatat gtcactgtca attatgcggg ctattggatg gtgcgcaatg  10440
tgtatctcaa tcctgaagca gcaggatata gtgtattgaa tggcgtatta tctatcatca  10500
```

```
tgctggtgtt aggcttcatc attatcgtgg cggctgtgaa aaaatgggcg cagatgtgga    10560
aagatccgag cttaaggatg aagcatcta taccgggcta aaggactat tgaaaatgct    10620 gagaggggtt ggcaatgaat ctatcaatga aatatcttat tctatacgta tcggacagca    10680
agcgggctat tcatttttta ccgggatatt ttaggactgc cgattcgtgc tgaacacggc    10740
acgtatgtcg aatttgatac agggtctacg atattggcgc ttaatacccg ggaaagcgcc    10800
agagacatca cggcgctgga cattccggat acatctgctt caaacacatt tgaaatcggg    10860
tttgttactg aaaatgtaga agcggtcatc aaaaggatga gagaacaagg cgtatcgatt    10920
atcggggagc cgaaagtgaa accatggggg cagacggtcg cctatatcgc tgatccggat    10980
ggacattata tcgaaatttg cagtccgatg gaataacgca caaaagccca aaacaatgtc    11040
tgttttgggc tttctcatga tgttttgtgc ccggctgctt ctaatagcaa atcagccagg    11100
tgaacggctc tgactttacc gcttagtcct tcgcgttcaa tgccgagctt catctgcagc    11160
aggcagccag gatttgctgt tacaatgagg atcgcttcgg ttgctttgac ggcagccatt    11220
ttgctgtcca gtattttcat agacatttca acttcgacga tgttgtaaat tcccgctgac    11280
ccgcagcagc tgtctgcttt ctccatttct ttgaattccg cccctttgat gcttttaaga    11340
agctggcggg gctcgagtga cgtatgcatc acatttctta gatgacatga atcttggtag    11400
gtaacgacct gaggcgtctc gagtgctaga tccatttgat ggaaatcgag ttcaaccaaa    11460
acagaagaaa aatccttcag cttttgaaca aaagcggcag cccgttccga ccactcaggg    11520
tcatccttca gcaaatgatc atattcagtg agaaaggctc cgcatcctcc tgcgtttgta    11580
atgactgcat ccacgtctaa tgcttcgaaa gca                                  11613
```

<210> SEQ ID NO 48
<211> LENGTH: 11934
<212> TYPE: DNA
<213> ORGANISM: Bacillus licheniformis
<220> FEATURE:
<221> NAME/KEY: misc_feature
<222> LOCATION: (1)..(529)
<223> OTHER INFORMATION: The araB gene.
<220> FEATURE:
<221> NAME/KEY: primer_bind
<222> LOCATION: (1)..(23)
<223> OTHER INFORMATION: Primer 30013
<220> FEATURE:
<221> NAME/KEY: primer_bind
<222> LOCATION: (31)..(55)
<223> OTHER INFORMATION: Primer 30007
<220> FEATURE:
<221> NAME/KEY: misc_feature
<222> LOCATION: (548)..(1231)
<223> OTHER INFORMATION: The araD gene.
<220> FEATURE:
<221> NAME/KEY: misc_feature
<222> LOCATION: (1251)..(1943)
<223> OTHER INFORMATION: The araM' sequence.
<220> FEATURE:
<221> NAME/KEY: misc_feature
<222> LOCATION: (2171)..(2902)
<223> OTHER INFORMATION: The erm gene.
<220> FEATURE:
<221> NAME/KEY: primer_bind
<222> LOCATION: (2963)..(3010)
<223> OTHER INFORMATION: Primer 30590
<220> FEATURE:
<221> NAME/KEY: primer_bind
<222> LOCATION: (2963)..(2986)
<223> OTHER INFORMATION: Primer 27095 complement
<220> FEATURE:
<221> NAME/KEY: misc_feature
<222> LOCATION: (3053)..(3832)

```
<223> OTHER INFORMATION: The spec gene.
<220> FEATURE:
<221> NAME/KEY: primer_bind
<222> LOCATION: (3827)..(3874)
<223> OTHER INFORMATION: Primer 30017 complement
<220> FEATURE:
<221> NAME/KEY: primer_bind
<222> LOCATION: (3851)..(3900)
<223> OTHER INFORMATION: Primer 30019
<220> FEATURE:
<221> NAME/KEY: misc_feature
<222> LOCATION: (3880)..(4312)
<223> OTHER INFORMATION: The 'araM gene.
<220> FEATURE:
<221> NAME/KEY: misc_feature
<222> LOCATION: (4312)..(5613)
<223> OTHER INFORMATION: The araN gene.
<220> FEATURE:
<221> NAME/KEY: misc_feature
<222> LOCATION: (5647)..(6588)
<223> OTHER INFORMATION: The araP gene.
<220> FEATURE:
<221> NAME/KEY: misc_feature
<222> LOCATION: (6591)..(7430)
<223> OTHER INFORMATION: The araQ gene.
<220> FEATURE:
<221> NAME/KEY: misc_feature
<222> LOCATION: (7469)..(8936)
<223> OTHER INFORMATION: The abfA gene.
<220> FEATURE:
<221> NAME/KEY: primer_bind
<222> LOCATION: (8912)..(8959)
<223> OTHER INFORMATION: Primer 30018
<220> FEATURE:
<221> NAME/KEY: primer_bind
<222> LOCATION: (8912)..(8936)
<223> OTHER INFORMATION: Primer 30020
<220> FEATURE:
<221> NAME/KEY: primer_bind
<222> LOCATION: (11877)..(11899)
<223> OTHER INFORMATION: Primer 30008 complement
<220> FEATURE:
<221> NAME/KEY: primer_bind
<222> LOCATION: (11909)..(11934)
<223> OTHER INFORMATION: Primer 30011 complement

<400> SEQUENCE: 48
ttcaacactc gttgatgccg atctgacggg aatgctgctc ggtatgaccc ttgccactaa      60
gcctgaagag ataccgtgt cattggttga agcgactgcc tgcgggacga ggatcattat     120
tgaaacgttc agacaaagcg gcgtgccgat cgaggagctg tatgccgcag gaggaatcgc     180
cgaaaaaaat ccgtttatca tgcaggttta cgcggatgtc accaacatgg aaatcaaaat     240
ttccggatct ccgcaggcgc cggctttagg ttcagcgata ttcggagcgc tcgcggccgg     300
aagcatgaac ggcggttacg accatatcga agaagcagtc gcacatatgg caagatcaa     360 ggataaaacg tacaaaccaa ttcctgaaaa cgtttcctta tacgatcagc tttatgcgga     420
atataaggag ctttacacgt acttcggaaa gcaaacaat gtgatgaaac gccttaaaaa     480
attgaaaaac atccagtccc ttagttctga ccccggtaaa gcgatggctt agagggagga     540
gaaaactgtg ctggaatctt tgaaagaaca agtattaaaa gcgaatttgc agcttgaaga     600
ataccggctt gtcaccttta catggggaaa tgtcagcggt attgaccggg agaataagct     660
ggtcgtcatc aagccgagcg gtgtcaaata cagcgatttg aaagccgaag atttagtggt     720
tctgaatatg gacggcgaga ttgtggaagg ggatctgaag ccatcttccg atacgccgac     780
acacctctat ctttaccggc agtttcaatc gatcggcggg atcgtccata cgcattcccc     840
gtgggcgaca agctgggctc agtcagggaa ggacattccg tcgctcggaa cgactcatgc     900
cgactactac cacggcgaca ttccgtgtac acgggaaatg gatcccgatg aaatcaggag     960
```

```
tcaatacgag ctgaatacag gaaaagtgat tgtagagacg ttccggcatc ttgaccccct   1020
ggcggtgccc gccgttctcg tgaacaatca cgggccgttt tgctggggaa aagacgcctt   1080
aactgccgta cacaatgccg tcgtcctgga agaagtcgcc aagatggcgt accgctccct   1140
gatgctgaat ccgtctctta agcggattaa gagcgctttg caggataagc attattttcg   1200
aaagcacggg gcagacgcct attacggcca atagaggagg gaagctgcca atgaatgact   1260
tgatctctta tgtgaaaaaa actttgggcg catgcgaatg cggaaccgtc caccacccgc   1320
ttacagtcga aaaaatcgcg atcggcgaca atgctgttga gcaagagctg cccgcttcg    1380 tgaaatcggc ttcctataaa aaagccgctg tcatttatga tgaaacgacc ggacggttag   1440
ccggcaagcg gattgcctct cttcttgagg aaacggctga acggttccg gtgctgctgg    1500 aagctaatga agcgggcgat gtgacggcgg atgagcaaac attggtgagt gcattgatcg   1560
gtgtaccgat tgatgcggat gtactaattg cggccggagc gggcacgatt cacgacatcg   1620
tcaggttttg cgcctatcag cgcggcattc cgtttatttc agttcctacg gctccgtcgg   1680
ttgacggttt tacttcagcc ggcgcaccgc tgattttaaa aggaaagaaa cagacggttc   1740
aaacgacagc gccgatcgcg cttttttgccg atttggagct cttgtgtcaa cgccgcagaa   1800
acatggtagc cgcaggtttt ggcgatatgc tcggcaaggt gacgtcgctt gcggattggg   1860
agattttccg cttgcttgcc ggcgagccgt attgtccggc cgccagccgg ctcacgaggg   1920
aagcgcttga tcaatgtctt gaccttcaat aatcgcatcc gattgcagta taaatttaac   1980
gatcactcat catgttcata tttatcagag ctcgtgctat aattatacta attttataag   2040
gaggaaaaaa tatgggcatt tttagtattt ttgtaatcag cacagttcat tatcaaccaa   2100
acaaaaaata agtggttata atgaatcgtt aataagcaaa attcatataa ccaaattaaa   2160
gagggttata atgaacgaga aaatataaa acacagtcaa aactttatta cttcaaaaca    2220
taatatagat aaaataatga caaatataag attaaatgaa catgataata tctttgaaat   2280
cggctcagga aaaggccatt ttacccttga attagtaaag aggtgtaatt tcgtaactgc   2340
cattgaaata gaccataaat tatgcaaaac tacagaaaat aaacttgttg atcacgataa   2400
tttccaagtt ttaaacaagg atatattgca gtttaaattt cctaaaaacc aatcctataa   2460
aatatatggt aatataccct ataacataag tacggatata atacgcaaaa ttgttttga   2520 tagtatagct aatgagattt atttaatcgt ggaatacggg tttgctaaaa gattattaaa   2580
tacaaaacgc tcattggcat tactttaat ggcagaagtt gatatttcta tattaagtat   2640
ggttccaaga gaatattttc atcctaaacc taaagtgaat agctcactta tcagattaag   2700
tagaaaaaaa tcaagaatat cacacaaaga taaacaaaag tataattatt tcgttatgaa   2760
atgggttaac aaagaataca agaaaatatt tacaaaaaat caatttaaca attccttaaa   2820
acatgcagga attgacgatt taaacaatat tagctttgaa caattcttat ctcttttcaa   2880
tagctataaa ttatttaata agtaagttaa gggatgcata aactgcatcc cttaacttgt   2940
ttttcgtgtg cctattttt gtgaatcgat tatgtctttt gcgcagccaa tctagggtaa   3000
gtaaattgag atataatata atttgtatga acataatcaa cgaggtgaaa tcatgagcaa   3060
tttgattaac ggaaaaatac caaatcaagc gattcaaaca ttaaaaatcg taaaagattt   3120
atttggaagt tcaatagttg gagtatatct atttggttca gcagtaaatg gtggtttacg   3180
cattaacagc gatgtagatg ttctagtcgt cgtgaatcat agtttacctc aattaactcg   3240
aaaaaaacta acagaaagac taatgactat atcaggaaag attggaaata cggattctgt   3300
```

```
tagaccactt gaagttacgg ttataaatag gagtgaagtt gtcccttggc aatatcctcc      3360
aaaaagagaa tttatatacg gtgagtggct caggggtgaa tttgagaatg gacaaattca      3420
ggaaccaagc tatgatcctg atttggctat tgttttagca caagcaagaa agaatagtat      3480 ttctctatttt ggtcctgatt cttcaagtat acttgtctcc gtacctttga cagatattcg      3540
aagagcaatt aaggattctt tgccagaact aattgagggg ataaaaggtg atgagcgtaa      3600
tgtaatttta accctagctc gaatgtggca acagtgact actggtgaaa ttacctcgaa      3660
agatgtcgct gcagaatggg ctatacctct tttacctaaa gagcatgtaa ctttactgga      3720
tatagctaga aaaggctatc ggggagagtg tgatgataag tgggaaggac tatattcaaa      3780
ggtgaaagca ctcgttaagt atatgaaaaa ttctatagaa acttctctca attaggctaa      3840
ttttatagca ccaacaggtg cttactttta aaactacgtc atgctggttc tcgaccattc      3900
aaggccggct tccggcggcg agcaccatct ttcccactac cttgaaatga aagcgctgga      3960
gaacaataag cggcaagtgc tccacggtgc taaagtcggc tgcagcgcga ttatgctgac      4020
tgacatttac cgatctctta tcggtgcaag cctgggtgat caacacgctg agcaagcgat      4080
tcgctccgtt tatgaaaagc tccctgacgg taagaaaatg gcagagtgga tgaggcgtat      4140
cggcgggcct gtatcattca aagaactcga tgttgaagaa gagctggtga gagaagcgct      4200
cgcatacgcc catcagctca gagaccggta tacgggactg aaaatcatca atcaatacgg      4260 cctttttgccg gggcttttag gcaaaggacc aggcgtgaaa ggggttaaaa tgtgaaaagg      4320
ttcctttcat ctatctttat ggtcacggtc gctgtatgtt tgcttttatc ggggtgcaag      4380
gcgagtcctg cctccgatca agcggacggc accgaactga cattttggac attcaacggc      4440
cttcatgaac agttttatgc tgagatggtg aaagaatgga acaaaaagta tcccgagcga      4500
aaaatcaaat taaatacagt ggtgtatccg tatggacaga tgcatgacaa tttatctatc      4560
tcgcttttag ccgggaaagg ggttccagat attgccgatg ttgagctggg gcgctattcg      4620 aacttttga agggctctga cattcctctt accgatttaa cgccgcttgt ggaggacgaa      4680
cgcgacaagt ttgttgaagc gaggctgacg ctctacagca agaacggcaa gctttacgga      4740
cttgacacac atgtcggaac taccgtgatg tattacaaca tggaaatgat gaataaagca      4800
ggcgttgatc cggacgacat caaaacatgg gaagattaca gggaagcggg caaaaaggtc      4860
gtcaaagctc tcgaaaagcc gatgacgacg attgaaacga ccgacccgaa ttcatttctg      4920
ccgctggttt cccagcaggg atccggttac tttgatgagc aggggcggtt gacattaaac      4980
aatgagacaa acgtgaaaac gctcgaattt ttaaagactt taattgagaa agacaaaatt      5040
gccgtcacaa cgcccggagg caatcatcac agtgaagagt attacggatt tatgaaccaa      5100
ggcggcgcgg cgtctgtctt aatgccgatc tggtatatgg gccgtttttt ggattatatg      5160
cctgacttga aagggaaaat cgcgatcaga ccgctgccgg catgggaaga aggggagac      5220 cgctcagcgg gaatgggcgg aacggccacc gtgattccaa acaggcgaa acaggtcgat      5280 ctggccaagg atttcttgaa atttgccaaa gcgtcaaaag aaggcaacac caagctgtgg      5340
accgtgctcg ggttcgatcc gctcagatgg gatgtgtggg actcggacga attgaaaaaa      5400
acaaatcaat atacagaata ctttcaaaac ggacaacaca tcttttccgt gcttcttgac      5460
ataaaggatg agatcaatcc gctttacctt actgaggatt atgcgaagac ttccgatctc      5520
gtcaacagaa acatactgta cgaagcgctc aaaacgaaga gcaaacaccc gaaagaagca      5580
ttggacaaag cagcagctga agtgaaaggg caatagtctt tcattactgt aaagcgaggc      5640
gataacttga agactgttaa aacagataca gtgcattcgt ttccgccggt gagcagaaaa      5700
```

```
agaaagatca gacgtttatt atattcagca aaagccgcac cctacatttt tacagcacct   5760
tttgtactct cctttttgcat attttttctt tatccgctta tcagcgtcgt catcatgagt   5820
tttcaaagca ttctccccgg ggaagtccgc ttcatcggga cggagaacta taaagcatta   5880
aacaatccta cattttatac cgcactattc aacaccgtaa aatacacctt ttggacattg   5940
ctgattttaa tacctgttcc tcttattctg gcagtctttt tagattctaa actcgtaaag   6000
tttaaaaacg tgttcaaatc ggctttattc atcccggctc tgacttcaac cattgtggcg   6060
gggattattt tcaggctgat ttttggagaa atggatacat ccctggcgaa ttcgatattg   6120
gctaagctcg gaggttcgcc gtacaactgg ctgaacaatg aacataccgg catgttttta   6180
atggtgatgc tcgcatcttg gagatggatg gggatcaatg tcctgtactt tttggcgggc   6240
ttgcagaacg ttccgaaaga attgtatgaa gctgccgaaa tcgacggggc aggcacgttc   6300
aagaagtttt accatattac gcttccgttt ttaaagcccg tcagcgtcta cgtgctgacg   6360
atcagcatca tcggcggctt ccggatgttt gaagaaagct acgtgctgtg gcagaacaac   6420
tctccgggca acatcggcct gacgatggtc ggatacattt atcagcaggg gcttgcctac   6480
aacaacatgg gctacggatc ggcgctcggc atcgtgctct tgatcatcat tttcatctgc   6540
agcctcattt cattaaagct gtctggatct tttaaaaagg agggctatta atgcgtcctg   6600
ccggaggcct caacattgcg aaagtagctc tgtttctgct gtttgcgata ttaagctttt   6660
tgtttgtgtt tccgctcttc tgccttgtac tcggctcgct caagccatct tcggaattgc   6720
tgcgcttcgg cctgaattta agctgagcc ctgaaatcct gagccttgac aattacactt   6780
acttgtttaa cggaggcagc atttatttc aatggttttc gaacagcttg attctcgtgg   6840
tgatatccac cgtgctgacg ctcttgtttt cttcaatggt cggatacggg cttgccgtct   6900
acgactttaa aggaaaaaat ctcttgttcg tagccgtgct cctgatcatg atggtgccga   6960
tcgaaattct catgctgcct ttatttaaaa tgacggtttc tcttcatatt gtcgacacat   7020
acgccggtgt gatcctgccg tttatcgtct cgcctgtagc cgtgttttc ttcagacagt   7080 atgcgctcgg cctgccgaga gatttgcttg attccgcgag aatggacggc tgcacagagt   7140
tcggcattta cttcaggatc atggcgccct tgatgaagcc ggcatttgga gcgatgatca   7200
ttcttcaatc cttaaacagc tggaacaact tcttatggcc gctgatcgtt ttgcgatcga   7260
aagaaatgtt tacgctccca atcggactgt ccgctttgct cagtccgtac gggaacaatt   7320 atgcacatgtt gatttcgggt tctgtgctgg cgattctgcc cgtgattctc atcttcctgt   7380
tcttccagaa gtactttata tcaggtttga cggcgggcgg aatcaaaggc tgatccacta   7440
tatatcatct tgaaaggaat gatttaacat gactgtacac aaagcgaaga tgacgattga   7500
caaggaatat aaggtggcag agattgataa gcgaatttac ggctcctta tcgagcatct   7560 cggcagagcc gttatgaag gcatttatga gcctgatcat cctgaagctg acgaatcagg   7620 cttttcggaaa gatgtcatta aactagtcag agaactaaag gtgccgttta tcaggtatcc   7680
cggcggaaac tttgtatctg gatataactg ggaggatgga gtcggacctg tcgaacagcg   7740
gccgacaaga cttgatttgg cgtgggcgac aaccgagccg aacttaatcg gtacgaacga   7800
atttatggat tgggcaaagc ttgtcggggc agaggtgaat atggccgtca acctcggaac   7860
gagaggaatt gatgccgcac gcaacctagt agaatattgc aaccatccgt caggatcgta   7920
ctacagcgac ttgagaaaat cccacggata taaggaaccg cataaaatta aaacatggtg   7980
cctcggcaat gaaatggacg gtccatggca aatcggccat aaaacagcgg ccgaatacgg   8040
```

-continued

```
aagacttgct gctgaagccg cgaaggtgat gaaatggacg gacccgtcga tcgagcttgt    8100
cgcctgcgga agttcgggaa gcggaatgcc gacattcatc gactgggaaa cgaccgtgct    8160
tgaccatacg tacgaacacg tcgagtacat ctcgcttcac tcgtattacg gcaaccgcga    8220
caatgatctt ccaaactatt tggcgagatc gctagacatg gatcacttta tcaaaacggt    8280
catctcagtc tgcgactata tgaaagcgaa aagaaaagc aagaaaacga ttcacctttc     8340
atatgatgag tggaatgtct ggtatcactc gaatgaaaaa gacaaagaag ctgaacgctg    8400
ggcgaaagcg ccgcaccttc ttgaagacat ctacaacttt gaggatgcgc ttctcgtcgg    8460
ctgtatgctg attacgatgc tcaagcatgc cgaccgcgtg aaaatcgcct gtctggctca    8520
gcttgtcaat gtcatcgcgc cgattatgac agacaaaggg ggagaagcat ggcgtcagac    8580
cattttctat ccgtttatgc acgcttccgt ctacggcaga ggaacggtac tgcagacggc    8640
ggtatcgtct ccaaagtatg atgcgaaaga ctttacggat gtgccgtact ggagtccgt     8700
gtctgttttc aatgaagaag ccgaggaatt aaccgttttt gccgtcaacc gcgcaacaga    8760
cgccggcctt gaaatggaag ccgatatgag aagcttgaa gggtacagtg tctctgagca     8820
catcgttctg gaacacgaag atcataaagc gacgaatgaa aaagaccgca acaacgtcgt    8880
tccgcacagc ggcggagacg ccaaagtatg tgacggcagg ctgacggctc accttctttc    8940
ctggaatgtg atccgcctga aaaaacagtc ataagaatag caaagccgga gatttctctc    9000
cggcttgtct ttcaactgcc acgagccggc ccattccagc cggcttttg tataggaaaa     9060
aatgaccgct tttccaccatg aaattatgat atatttatga aaaacagaaa aggggatggg    9120
agaaaatgaa tgcggttaca attgtgatag catcaatgtg tattttggct attgcctatc    9180
gtttatacgg aacatttatg atggtgaagg ttctcaaagt gaatgatgac aagccaacac    9240
ctgctcatgc gcttgaggat gggaaagact atgtgcctac aaataaatgg gtttcgttcg    9300
gccaccactt tgccgcgatc gcagcggccg ggccgctggt cggaccaatt ctggcggcgc    9360
agtttggcta tttgccggga ttattgtggc tgttaatcgg ggcggtaatt gggggagccg    9420
tccatgatat tgtggtgttg tttgcatcga tgcgcaaaaa cggaaaatcg ctgtcggaag    9480
tggcgaagga tgagcttggc cctgttcag gattttgtac aggactgtcc atgctgttta     9540
tcatcacgat cacaatggcg ggcctgtcga tggttgtctt gcatgcgctt gaacgtaatc    9600
catgggaac atttgcggtg gggattacga ttccgattgc gatgggtgtg ggcttatttt     9660
ataagaaaac gggaaattta agctcgcttt caacggtcgg ctttctcttt ttaatggcag    9720
gagtctttat cggtccatgg gtacagacta ccgcgctcgg tgacttttta acgctagata    9780
cgaaaacgct tgcaatcgcg cttcctgttt atgcgttttt tgcggctgcg cttcccgttt    9840
ggctgcttct ggctccgcgt gattatttaa gcagctttat gaaaatcggt gttttatcg     9900
ctttgattgt tggtgtgttt gtcgtcaatc cgtccattcc gttccctgcg tttacagaat    9960
tcgtaaaagg cggagggccg gtgctggcag gacctgtctg gccgttcatc tcaataacca    10020
tcgcctgcgg ggcgatctct gggttccatg cctttgtcgg ctcaggaacg acaccgaaaa    10080
tgctgaataa atggagtgat atgaagccgg ttgcgtttgg cgcaatgctt gttgagtgtc    10140
ttgtcggtat catggcgctg attgcagcga ccgctttaca gcctgctgat tactttcga     10200
ttaacagcac gcctgaggtt ttccgtacgc ttggcatgaa tgtcgtacat ttgcctgaat    10260
tgagcgggga aatcggttg gactagaag gaagaacagg gggagccgtc acgcttgcgg      10320
tagggatgac ttatattttt accggaatgc cgttttcag ccatttggcc tcatactttt     10380
tccaatttgt cattatgttt gaagcggtct ttattttaac agcgattgac gccggcacac    10440
```

```
gtgtcgcccg ttatttgatc caggacttct tcggggaggt gtataagccg ctgaagaaaa    10500
cagactggat tccgggctct gtatttgcca gcgcgcttgc ctgtttgatg tgggggtact    10560
tgctgtattc aggagatatc ggttccattt gggcgctctt cggcgtttct aatcagctga    10620
tggcttcagt ggggctgatt atcggagcga cgatcgtgct gaaaatcgcc gataaacgcc    10680
ggtacattct gacttgcctt atcccgcttg cctatttata tgtcactgtc aattatgcgg    10740
gctattggat ggtgcgcaat gtgtatctca atcctgaagc agcaggatat agtgtattga    10800
atggcgtatt atctatcatc atgctggtgt taggcttcat cattatcgtg cggctgtga     10860 aaaaatgggc gcagatgtgg aaagatccga gcttaaggat ggaagcatct ataccgggct    10920
agaaggacta ttgaaaatgc tgagaggggt tggcaatgaa tctatcaatg aaatatctta    10980
ttctatacgt atcggacagc aagcgggcta ttcatttttt accgggatat tttaggactg    11040
ccgattcgtg ctgaacacgg cacgtatgtc gaatttgata cagggtctac gatattggcg    11100
cttaataccc gggaaagcgc cagagacatc acggcgctgg acattccgga tacatctgct    11160
tcaaacacat ttgaaatcgg gtttgttact gaaaatgtag aagcggtcat caaaaggatg    11220
agagaacaag gcgtatcgat tatcggggag ccgaaagtga aaccatgggg gcagacggtc    11280
gcctatatcg ctgatccgga tggacattat atcgaaattt gcagtccgat ggaataacgc    11340
acaaaagccc aaaacaatgt ctgtttttggg ctttctcatg atgttttgtg cccggctgct    11400
tctaatagca aatcagccag gtgaacggct ctgactttac cgcttagtcc ttcgcgttca    11460
atgccgagct tcatctgcag caggcagcca ggatttgctg ttacaatgag gatcgcttcg    11520
gttgctttga cggcagccat tttgctgtcc agtatttca tagacatttc aacttcgacg    11580
atgttgtaaa ttcccgctga cccgcagcag ctgtctgctt tctccatttc tttgaattcc    11640 gccccttttga tgcttttaag aagctggcgg ggctcgagtg acgtatgcat cacatttctt    11700
agatgacatg aatcttggta ggtaacgacc tgaggcgtct cgagtgctag atccatttga    11760
tggaaatcga gttcaaccaa aacagaagaa aaatccttca gcttttgaac aaaagcggca    11820
gcccgttccg accactcagg gtcatccttc agcaaatgat catattcagt gagaaaggct    11880
ccgcatcctc ctgcgtttgt aatgactgca tccacgtcta atgcttcgaa agca           11934
```

```
<210> SEQ ID NO 49
<211> LENGTH: 7330
<212> TYPE: DNA
<213> ORGANISM: Bacillus licheniformis
<220> FEATURE:
<221> NAME/KEY: misc_feature
<222> LOCATION: (1)..(1646)
<223> OTHER INFORMATION: The araB gene
<220> FEATURE:
<221> NAME/KEY: primer_bind
<222> LOCATION: (1)..(23)
<223> OTHER INFORMATION: Primer 35881
<220> FEATURE:
<221> NAME/KEY: primer_bind
<222> LOCATION: (1)..(3060)
<223> OTHER INFORMATION: B. licheniformis DNA
<220> FEATURE:
<221> NAME/KEY: primer_bind
<222> LOCATION: (25)..(48)
<223> OTHER INFORMATION: Primer 36818
<220> FEATURE:
<221> NAME/KEY: misc_feature
<222> LOCATION: (1665)..(2348)
<223> OTHER INFORMATION: The araD gene
<220> FEATURE:
<221> NAME/KEY: misc_feature
<222> LOCATION: (2368)..(3060)
```

```
<223> OTHER INFORMATION: The araM' sequence.
<220> FEATURE:
<221> NAME/KEY: primer_bind
<222> LOCATION: (3036)..(3082)
<223> OTHER INFORMATION: Primer 35895 complement
<220> FEATURE:
<221> NAME/KEY: primer_bind
<222> LOCATION: (3037)..(3082)
<223> OTHER INFORMATION: Primer 35876
<220> FEATURE:
<221> NAME/KEY: misc_feature
<222> LOCATION: (3110)..(3222)
<223> OTHER INFORMATION: The res sequence.
<220> FEATURE:
<221> NAME/KEY: misc_feature
<222> LOCATION: (3352)..(3999)
<223> OTHER INFORMATION: The cat sequence complementary
<220> FEATURE:
<221> NAME/KEY: misc_feature
<222> LOCATION: (4131)..(4265)
<223> OTHER INFORMATION: The res sequence.
<220> FEATURE:
<221> NAME/KEY: primer_bind
<222> LOCATION: (4282)..(4330)
<223> OTHER INFORMATION: Primer 35878
<220> FEATURE:
<221> NAME/KEY: primer_bind
<222> LOCATION: (4282)..(4306)
<223> OTHER INFORMATION: Primer 656520 complement
<220> FEATURE:
<221> NAME/KEY: misc_feature
<222> LOCATION: (4307)..(4739)
<223> OTHER INFORMATION: The 'araM sequence.
<220> FEATURE:
<221> NAME/KEY: primer_bind
<222> LOCATION: (4307)..(7330)
<223> OTHER INFORMATION: B. licheniformis DNA
<220> FEATURE:
<221> NAME/KEY: misc_feature
<222> LOCATION: (4739)..(6040)
<223> OTHER INFORMATION: The araN sequence.
<220> FEATURE:
<221> NAME/KEY: misc_feature
<222> LOCATION: (6074)..(7015)
<223> OTHER INFORMATION: The araP sequence.
<220> FEATURE:
<221> NAME/KEY: misc_feature
<222> LOCATION: (7018)..(7330)
<223> OTHER INFORMATION: The araQ sequence.
<220> FEATURE:
<221> NAME/KEY: primer_bind
<222> LOCATION: (7284)..(7306)
<223> OTHER INFORMATION: Primer 36817 complement
<220> FEATURE:
<221> NAME/KEY: primer_bind
<222> LOCATION: (7309)..(7330)
<223> OTHER INFORMATION: Primer 35880 complement

<400> SEQUENCE: 49
gtgcagttct cgtcgatgtc cggacaggtg aggaaatcgc gacagctgtc aaagagtaca      60
cgcacggggt gatagaccgg gagcttccgg tctcaaagcg aaagcttccg agagactggg     120
cgctccagca tccggccgat tacattgaag tgctggagga acgattccg agccttttga      180 aacagtcaaa agcggatccg aaagaaatca tcggaatcgg aatcgatttc acggcttgca    240
cgattttgcc cgttgacgag aacgggactc ctctttgtat gagggaagag tatgcgtcag    300
aaccgcacag ctatgtgaag ctttggaagc accatgctgc acaggagcag gcgaatcgct   360
taaatcaaat cgcggaagaa agaaatgaac cttttcttca aacatacggc gggaaaattt    420
cttccgagtg gctcgttcca aaagtgatgc aaatcgcgga agaagcgcct gacatttatg    480
atgccgcagc cgagatcatg gaagcggccg actggatcgt ctatatgctg tgcggaacca   540
gaaagcgcaa caattgcaca gcgggttata aagcgatttg gaacaataag agcggctatc   600
```

```
cttccgacga tttcttcgca agcctgcatc cgaagctgaa aaatatcgtt cgggaaaaac    660
taacggagga tatttattct gtaggcgaaa agcgggcgg actgactgaa gaaatggccg     720
ggaagacagg gcttctggca ggtacggcgg tcgctgtcgc aaatgttgat gctcatgtgt   780
cggttccggc ggtcggcatc acagagccgg gcaagatgct gatgatcatg ggaacgtcta   840
cctgtcacat gctgctcggc gaggatgtca ggatggtgcc gggaatgtgc ggcgtcgttg   900
aagacgggat tctgccgggc tatgtcggct atgaagcggg ccaatcgtgc gttggcgacc   960 atttcattg gctgattcaa cactttgttc cagaagcgta tttgaaagaa gctgaagccg    1020
aagggatttc catttacgaa ctgctgtctc aaaaggccgg cagtctccaa atcggtgaaa   1080
gcggtttgct tgcattggat tggtggaacg gaaaccgttc aacactcgtt gatgccgatc   1140
tgacgggaat gctgctcggt atgacccttg ccactaagcc tgaagagata taccgtgcat   1200
tggttgaagc gactgcctgc gggacgagga tcattattga aacgttcaga caaagcggcg   1260
tgccgatcga ggagctgtat gccgcaggag gaatcgccga aaaaaatccg tttatcatgc   1320
aggtttacgc ggatgtcacc aacatggaaa tcaaaatttc cggatctccg caggcgccgg   1380
ctttaggttc agcgatattc ggagcgctcg cggccggaag catgaacggc ggttacgacc   1440
atatcgaaga agcagtcgca catatgggca agatcaagga taaaacgtac aaaccaattc   1500
ctgaaaacgt ttccttatac gatcagcttt atgcggaata taaggagctt tacacgtact   1560
tcggaaagca aaacaatgtg atgaaacgcc ttaaaaaatt gaaaaacatc cagtcccttta  1620 gttctgaccc cggtaaagcg atggcttaga gggaggagaa aactgtgctg gaatctttga   1680
aagaacaagt attaaaagcg aatttgcagc ttgaagaata ccggcttgtc acctttacat   1740
ggggaaatgt cagcggtatt gaccgggaga taagctggt cgtcatcaag ccgagcggtg    1800
tcaaatacag cgatttgaaa gccgaagatt tagtggttct gaatatggac ggcgagattg   1860 tggaaggggga tctgaagcca tcttccgata cgccgacaca cctctatctt taccggcagt  1920
ttcaatcgat cggcgggatc gtccatacgc attccccgtg ggcgacaagc tgggctcagt   1980
cagggaagga cattccgtcg ctcggaacga ctcatgccga ctactaccac ggcgacattc   2040
cgtgtacacg ggaaatggat cccgatgaaa tcaggagtca atacgagctg aatacaggaa   2100
aagtgattgt agagacgttc cggcatcttg accccctggc ggtgcccgcc gttctcgtga   2160
acaatcacgg gccgttttgc tggggaaaag acgccttaac tgccgtacac aatgccgtcg   2220
tcctggaaga agtcgccaag atggcgtacc gctccctgat gctgaatccg tctcttaagc   2280
ggattaagag cgctttgcag gataagcatt attttcgaaa gcacggggca gacgcctatt   2340
acggccaata gaggagggaa gctgccaatg aatgacttga tctcttatgt gaaaaaaact   2400
ttgggcgcat gcgaatgcgg aaccgtccac cacccgctta cagtcgaaaa aatcgcgatc   2460
ggcgacaatg ctgttgagca agagctgccc gctttcgtga atcggcttc ctataaaaaa    2520 gccgctgtca tttatgatga aacgaccgga cggttagccg gcaagcggat tgcctctctt   2580
cttgaggaaa cggctgaaac ggttccggtg ctgctggaag ctaatgaagc gggcgatgtg   2640
acggcggatg agcaaacatt ggtgagtgca ttgatcggtg taccgattga tgcggatgta   2700
ctaattgcgg ccggagcggg cacgattcac gacatcgtca ggttttgcgc ctatcagcgc   2760
ggcattccgt ttatttcagt tcctacggct ccgtcggttg acggttttac ttcagccggc   2820
gcaccgctga ttttaaaagg aaagaaacag acggttcaaa cgacagcgcc gatcgcgctt   2880
tttgccgatt tggagctctt gtgtcaagcg ccgcagaaca tggtagccgc aggttttggc   2940
```

-continued

```
gatatgctcg gcaaggtgac gtcgcttgcg gattgggaga tttcccgctt gcttgccggc    3000
gagccgtatt gtccggccgc cagccggctc acgagggaag cgcttgatca atgtcttgac    3060
taagttaagg tggatacaca tcttgtcata tgatcaatgg ttcggatctg attttcctcc    3120
tctaatatgc tcaacttaaa tgacctattc aataaatcta ttatgctgct aaatagttta    3180
taggacaaat aagtatactc taatgaccta taaagatag aaaattaaaa aatcaagtgt     3240
tcgcttctct ctcacggagc tgtaatataa aaaccttctt cagctaacgg ggcaggttag    3300
tgacattaga aaaccgactg tagaaagtac agtcggcatt atctcatatt ataaaagcca    3360
gtcattaggc ctatctgaca attcctgaat agagttcata acaatcctg catgataacc     3420 atcacaaaca gaatgatgta cctgtaaaga tagcggtaaa tatattgaat tacctttatt    3480
aatgaatttt cctgctgtaa taatgggtag aaggtaatta ctattattat tgatatttaa    3540
gttaaaccca gtaaatgaag tccatggaat aatagaaaga gaaaaagcat tttcaggtat    3600
aggtgttttg ggaacaatt tccccgaacc attatatttc tctacatcag aaaggtataa     3660
atcataaaac tctttgaagt cattctttac aggagtccaa ataccagaga atgttttaga    3720
tacaccatca aaaattgtat aaagtggctc taacttatcc caataaccta actctccgtc    3780
gctattgtaa ccagttctaa aagctgtatt tgagtttatc acccttgtca ctaagaaaat    3840
aaatgcaggg taaatttat atccttcttg ttttatgttt cggtataaaa cactaatttc     3900
aatttctgtg gttatactaa aagtcgtttg ttggttcaaa taatgattaa atatctcttt    3960
tctcttccaa ttgtctaaat caattttatt aaagttcatt tgatatgcct cctaaatttt    4020
tatctaaagt gaatttagga ggcttacttg tctgctttct tcattagaat caatcctttt    4080
ttaaaagtca atattactgt aacataagta tatattttaa aaatatccac ggttcttcaa    4140
atatttcccc aagattttcc tcctctaata cgctcaactt aatgacctat tcaataaatc    4200
tattatgctg ctaaatagtt tataggacaa ataagtatac tctaatgacc ctataaaaga    4260
tagaagggat ccatagatta acgcgtggta cccggggatc ctctagcatg ctggttctcg    4320
accattcaag gccggcttcc ggcggcgagc accatctttc ccactacctt gaaatgaaag    4380
cgctggagaa caataagcgg caagtgctcc acggtgctaa agtcggctgc agcgcgatta    4440
tgctgactga catttaccga tctcttatcg gtgcaagcct gggtgatcaa cacgctgagc    4500
aagcgattcg ctccgtttat gaaaagctcc ctgacggtaa gaaaatggca gagtggatga    4560
ggcgtatcgg cgggcctgta tcattcaaag aactcgatgt tgaagaagag ctggtgagag    4620
aagcgctcgc atacgcccat cagctcagag accggtatac gggactgaaa atcatcaatc    4680
aatacggcct tttgccgggg cttttaggca aaggaccagg cgtgaagggg gttaaaatgt    4740
gaaaaggttc ctttcatcta tctttatggt cacggtcgct gtatgtttgc ttttatcggg    4800
gtgcaaggcg agtcctgcct ccgatcaagc ggacggcacc gaactgacat tttggacatt    4860
caacggcctt catgaacagt tttatgctga tggtgaaa gaatgaaaca aaaagtatcc      4920
cgagcgaaaa atcaaattaa atacagtggt gtatccgtat ggacagatgc atgacaattt    4980
atctatctcg cttttagccg ggaaaggggt tccagatatt gccgatgttg agctggggcg    5040
ctattcgaac tttttgaagg gctctgacat tcctcttacc gatttaacgc cgcttgtgga    5100
ggacgaacgc gacaagtttg ttgaagcgag gctgacgctc tacagcaaga acggcaagct    5160
ttacggactt gacacacatg tcggaactac cgtgatgtat tacaacatgg aaatgatgaa    5220
taaagcaggc gttgatccgg acgacatcaa aacatgggaa gattacaggg aagcgggcaa    5280
aaaggtcgtc aaagctctcg gaaagccgat gacgacgatt gaaacgaccg acccgaattc    5340
```

```
atttctgccg ctggtttccc agcagggatc cggttacttt gatgagcagg ggcggttgac    5400
attaaacaat gagacaaacg tgaaaacgct cgaattttta aagactttaa ttgagaaaga    5460
caaaattgcc gtcacaacgc ccggaggcaa tcatcacagt gaagagtatt acggatttat    5520
gaaccaaggc ggcgcggcgt ctgtcttaat gccgatctgg tatatgggcc gttttttgga    5580
ttatatgcct gacttgaaag ggaaaatcgc gatcagaccg ctgccggcat gggaagaagg    5640
gggagaccgc tcagcgggaa tgggcggaac ggccaccgtg attccaaaac aggcgaaaca    5700
ggtcgatctg gccaaggatt tcttgaaatt tgccaaagcg tcaaaagaag gcaacaccaa    5760
gctgtggacc gtgctcgggt tcgatccgct cagatgggat gtgtgggact cggacgaatt    5820
gaaaaaaaca aatcaatata cagaatactt tcaaaacgga caacacatct tttccgtgct    5880
tcttgacata aaggatgaga tcaatccgct ttaccttact gaggattatg cgaagacttc    5940
cgatctcgtc aacagaaaca tactgtacga agcgctcaaa acgaagagca aaacaccgaa    6000
agaagcattg gacaaagcag cagctgaagt gaaagggcaa tagtctttca ttactgtaaa    6060
gcgaggcgat aacttgaaga ctgttaaaac agatacagtg cattcgtttc gccggtgag     6120 cagaaaaaga aagatcagac gtttattata ttcagcaaaa gccgcaccct acatttttac    6180
agcacctttt gtactctcct tttgcatatt ttttctttat ccgcttatca gcgtcgtcat    6240
catgagtttt caaagcattc tccccgggga agtccgcttc atcgggacgg agaactataa    6300
agcattaaac aatcctacat tttataccgc actattcaac accgtaaaat acaccttttg    6360
gacattgctg atttttaatac ctgttcctct tattctggca gtcttttag attctaaact    6420 cgtaaagttt aaaaacgtgt tcaaatcggc tttattcatc ccggctctga cttcaaccat    6480
tgtggcgggg attattttca ggctgatttt tggagaaatg gatacatccc tggcgaattc    6540
gatattggct aagctcggag gttcgccgta caactggctg aacaatgaac ataccggcat    6600 gttttaatg gtgatgctcg catcttggag atggatgggg atcaatgtcc tgtacttttt     6660
ggcgggcttg cagaacgttc cgaaagaatt gtatgaagct gccgaaatcg acggggcagg    6720
cacgttcaag aagttttacc atattacgct tccgttttta aagcccgtca gcgtctacgt    6780
gctgacgatc agcatcatcg gcggcttccg gatgtttgaa gaaagctacg tgctgtggca    6840
gaacaactct ccgggcaaca tcggcctgac gatggtcgga tacatttatc agcaggggct    6900
tgcctacaac aacatgggct acggatcggc gctcggcatc gtgctcttga tcatcatttt    6960
catctgcagc ctcatttcat taaagctgtc tggatctttt aaaaaggagg ctattaatg     7020 cgtcctgccg gaggcctcaa cattgcgaaa gtagctctgt ttctgctgtt tgcgatatta    7080
agctttttgt ttgtgtttcc gctcttctgc cttgtactcg gctcgctcaa gccatcttcg    7140
gaattgctgc gcttcggcct gaatttaaag ctgagccctg aaatcctgag ccttgacaat    7200
tacacttact tgtttaacgg aggcagcatt tattttcaat ggttttcgaa cagcttgatt    7260
ctcgtggtga tatccaccgt gctgacgctc ttgttttctt caatggtcgg atacgggctt    7320
gccgtctacg                                                           7330
```

<210> SEQ ID NO 50
<211> LENGTH: 2347
<212> TYPE: DNA
<213> ORGANISM: Artificial sequence
<220> FEATURE:
<223> OTHER INFORMATION: Synthetic construct
<220> FEATURE:
<221> NAME/KEY: promoter
<222> LOCATION: (18)..(245)

```
<223> OTHER INFORMATION: PamyL
<220> FEATURE:
<221> NAME/KEY: promoter
<222> LOCATION: (251)..(346)
<223> OTHER INFORMATION: PamyQsc
<220> FEATURE:
<221> NAME/KEY: promoter
<222> LOCATION: (364)..(459)
<223> OTHER INFORMATION: PcryIIIA
<220> FEATURE:
<221> NAME/KEY: RBS
<222> LOCATION: (460)..(1016)
<223> OTHER INFORMATION: cryIIIA stabilizer
<220> FEATURE:
<221> NAME/KEY: sig_peptide
<222> LOCATION: (1100)..(1186)
<223> OTHER INFORMATION: SPaprL
<220> FEATURE:
<221> NAME/KEY: misc_feature
<222> LOCATION: (1187)..(2245)
<223> OTHER INFORMATION: The aprH coding sequence.

<400> SEQUENCE: 50
```

| | | | | | |
|---|---|---|---|---|---|
| gatctagatc | aggtaccgca | acgttcgcag | atgctgctga | agagattatt | aaaaagctga | 60 |
| aagcaaaagg | ctatcaattg | gtaactgtat | ctcagcttga | agaagtgaag | aagcagagag | 120 |
| gctattgaat | aaatgagtag | aaagcgccat | atcggcgctt | ttcttttgga | agaaaatata | 180 |
| gggaaaatgg | tacttgttaa | aaattcgaa | tatttataca | atatcatatg | tatcacattg | 240 |
| aaaggagggg | cctgctgtcc | agactgtccg | ctgtgtaaaa | aaaaggaata | aaggggggtt | 300 |
| gacattattt | tactgatatg | tataatataa | tttgtataag | aaaatggagg | ggccctcgaa | 360 |
| acgtaagatg | aaaccttaga | taaaagtgct | ttttttgttg | caattgaaga | attattaatg | 420 |
| ttaagcttaa | ttaaagataa | tatctttgaa | ttgagatcta | atatctttga | attgtaacgc | 480 |
| ccctcaaaag | taagaactac | aaaaaaagaa | tacgttatat | agaaatatgt | ttgaaccttc | 540 |
| ttcagattac | aaatatattc | ggacggactc | tacctcaaat | gcttatctaa | ctatagaatg | 600 |
| acatacaagc | acaaccttga | aaatttgaaa | atataactac | caatgaactt | gttcatgtga | 660 |
| attatcgctg | tatttaattt | tctcaattca | atatataata | tgccaataca | ttgttacaag | 720 |
| tagaaattaa | gacacccttg | atagcctac | tatacctaac | atgatgtagt | attaaatgaa | 780 |
| tatgtaaata | tatttatgat | aagaagcgac | ttatttataa | tcattacata | ttttctatt | 840 |
| ggaatgatta | agattccaat | agaatagtgt | ataaattatt | tatcttgaaa | ggagggatgc | 900 |
| ctaaaaacga | agaacattaa | aaacatatat | ttgcaccgtc | taatggatag | aaaggaggtg | 960 |
| atccagccgc | accttatgaa | aaatcatttt | atcagtttga | aaattatgta | ttatggaaga | 1020 |
| gctgaaaggg | gaggagaacc | atggaactag | tctggatcct | acgcgttcat | atgtatcaca | 1080 |
| ttgaaagggg | aggagaatca | tgatgaggaa | aaagagtttt | tggcttggga | tgctgacggc | 1140 |
| cttcatgctc | gtgttcacga | tggcattcag | cgattccgct | tctgctgctg | aagaagcaaa | 1200 |
| agaaaaatat | ttaattggct | taatgagca | ggaagctgtc | agtgagtttg | tagaacaagt | 1260 |
| agaggcaaat | gacgaggtcg | ccattctctc | tgaggaagag | gaagtcgaaa | ttgaattgct | 1320 |
| tcatgaattt | gaaacgattc | ctgttttatc | cgttgagtta | agcccagaag | atgtggacgc | 1380 |
| gcttgaactc | gatccagcga | tttcttatat | tgaagaggat | gcagaagtaa | cgacaatggc | 1440 |
| gcaatcggta | ccatggggaa | ttagccgtgt | gcaagcccca | gctgcccata | accgtggatt | 1500 |
| gacaggttct | ggtgtaaaag | ttgctgtcct | cgatacaggg | atatccactc | atccagatct | 1560 |
| aaatattcgt | ggtggcgcaa | gctttgtacc | agggggaaccg | tcgactcaag | atgggaatgg | 1620 |
| gcatggcacg | catgtggccg | ggacgatcgc | tgctttaaac | aattcgattg | gcgttcttgg | 1680 |

-continued

```
cgtagctcct agcgctgagc tatacgctgt taaagtccta ggggcgagcg gttcaggctc    1740
ggtcagctcg attgcccaag gattggaatg ggcaggaaac aatggcatgc acgttgctaa    1800
tttgagttta ggaagccctt cgccaagtgc cacactcgag caagctgtta atagcgcgac    1860
ttctagaggc gttcttgttg tagcggcatc tgggaattca ggtgcaggct caatcagcta    1920
tccggcgcgc tatgcgaacg caatggcagt cggagctact gatcaaaaca acaaccgcgc    1980
tagcttttca cagtatggcg caggccttga cattgtcgca cccggggtaa acgtgcagag    2040 cacatacccca ggttcaacat atgccagctt aaacggtaca tcgatggcta ctcctcatgt   2100
tgcaggtgcg gccgcccttg ttaaacaaaa gaacccatct tggtctaatg tacaaattcg    2160
aaatcatcta aagaatacgg caactagttt aggaagcacg aacttgtatg gaagcggact    2220
tgttaacgca gaagcggcaa cgcgttaata acgcgtgcta gcggccgcgt cgactagaag    2280
agcagagagg acggatttcc tgaaggaaat ccgtttttt attttgcccg tcttataaat     2340
ttcgttg                                                              2347
```

<210> SEQ ID NO 51
<211> LENGTH: 9952
<212> TYPE: DNA
<213> ORGANISM: Artificial sequence
<220> FEATURE:
<223> OTHER INFORMATION: Synthetic construct
<220> FEATURE:
<221> NAME/KEY: misc_feature
<222> LOCATION: (1)..(1646)
<223> OTHER INFORMATION: The araB sequence.
<220> FEATURE:
<221> NAME/KEY: primer_bind
<222> LOCATION: (1)..(23)
<223> OTHER INFORMATION: Primer 35881
<220> FEATURE:
<221> NAME/KEY: primer_bind
<222> LOCATION: (25)..(48)
<223> OTHER INFORMATION: Primer 36818
<220> FEATURE:
<221> NAME/KEY: misc_feature
<222> LOCATION: (1665)..(2348)
<223> OTHER INFORMATION: The araD sequence.
<220> FEATURE:
<221> NAME/KEY: misc_feature
<222> LOCATION: (2368)..(3060)
<223> OTHER INFORMATION: The araM' sequence.
<220> FEATURE:
<221> NAME/KEY: primer_bind
<222> LOCATION: (3036)..(3084)
<223> OTHER INFORMATION: Primer 35894 complement
<220> FEATURE:
<221> NAME/KEY: primer_bind
<222> LOCATION: (3061)..(3084)
<223> OTHER INFORMATION: Primer 35893
<220> FEATURE:
<221> NAME/KEY: misc_feature
<222> LOCATION: (3074)..(3212)
<223> OTHER INFORMATION: The res sequence.
<220> FEATURE:
<221> NAME/KEY: misc_feature
<222> LOCATION: (3427)..(4206)
<223> OTHER INFORMATION: The spec sequence.
<220> FEATURE:
<221> NAME/KEY: misc_feature
<222> LOCATION: (4410)..(4546)
<223> OTHER INFORMATION: The res sequence.
<220> FEATURE:
<221> NAME/KEY: primer_bind
<222> LOCATION: (4560)..(4608)
<223> OTHER INFORMATION: Primer 39951
<220> FEATURE:
<221> NAME/KEY: primer_bind
<222> LOCATION: (4583)..(4608)

```
<223> OTHER INFORMATION: Primer 39950
<220> FEATURE:
<221> NAME/KEY: promoter
<222> LOCATION: (4600)..(4827)
<223> OTHER INFORMATION: The amyL promoter
<220> FEATURE:
<221> NAME/KEY: promoter
<222> LOCATION: (4833)..(4928)
<223> OTHER INFORMATION: The amyQsc promoter
<220> FEATURE:
<221> NAME/KEY: promoter
<222> LOCATION: (4946)..(5041)
<223> OTHER INFORMATION: The cryIIIA promoter
<220> FEATURE:
<221> NAME/KEY: sig_peptide
<222> LOCATION: (5682)..(5768)
<223> OTHER INFORMATION: The AprL signal peptide.
<220> FEATURE:
<221> NAME/KEY: misc_feature
<222> LOCATION: (5769)..(6827)
<223> OTHER INFORMATION: The aprH coding sequence
<220> FEATURE:
<221> NAME/KEY: misc_feature
<222> LOCATION: (6854)..(6927)
<223> OTHER INFORMATION: The amyL terminator sequence.
<220> FEATURE:
<221> NAME/KEY: RBS
<222> LOCATION: (6854)..(6927)
<220> FEATURE:
<221> NAME/KEY: primer_bind
<222> LOCATION: (6908)..(6929)
<223> OTHER INFORMATION: Primer 36001 complement
<220> FEATURE:
<221> NAME/KEY: primer_bind
<222> LOCATION: (6908)..(6952)
<223> OTHER INFORMATION: Primer 36002
<220> FEATURE:
<221> NAME/KEY: misc_feature
<222> LOCATION: (6930)..(7361)
<223> OTHER INFORMATION: The 'araM sequence.
<220> FEATURE:
<221> NAME/KEY: misc_feature
<222> LOCATION: (7361)..(8662)
<223> OTHER INFORMATION: The araN sequence.
<220> FEATURE:
<221> NAME/KEY: misc_feature
<222> LOCATION: (8696)..(9637)
<223> OTHER INFORMATION: The araP sequence.
<220> FEATURE:
<221> NAME/KEY: misc_feature
<222> LOCATION: (9640)..(9952)
<223> OTHER INFORMATION: The araQ sequence.
<220> FEATURE:
<221> NAME/KEY: primer_bind
<222> LOCATION: (9906)..(9928)
<223> OTHER INFORMATION: Primer 36817 complement
<220> FEATURE:
<221> NAME/KEY: primer_bind
<222> LOCATION: (9931)..(9952)
<223> OTHER INFORMATION: Primer 35880 complement

<400> SEQUENCE: 51
gtgcagttct cgtcgatgtc cggacaggtg aggaaatcgc gacagctgtc aaagagtaca      60
cgcacggggt gatagaccgg gagcttccgg tctcaaagcg aaagcttccg agagactggg     120
cgctccagca tccggccgat tacattgaag tgctggagga acgattccg agccttttga      180 aacagtcaaa agcggatccg aaagaaatca tcggaatcgg aatcgatttc acggcttgca     240
cgattttgcc cgttgacgag aacgggactc ctctttgtat gagggaagag tatgcgtcag    300
aaccgcacag ctatgtgaag ctttggaagc accatgctgc acaggagcag gcgaatcgct    360
taaatcaaat cgcggaagaa agaaatgaac cttttcttca aacatacggc gggaaaattt    420
cttccgagtg gctcgttcca aaagtgatgc aaatcgcgga agaagcgcct gacatttatg    480
```

```
atgccgcagc cgagatcatg gaagcggccg actggatcgt ctatatgctg tgcggaacca    540
gaaagcgcaa caattgcaca gcgggttata aagcgatttg gaacaataag agcggctatc    600
cttccgacga tttcttcgca agcctgcatc cgaagctgaa aaatatcgtt cgggaaaaac    660
taacggagga tatttattct gtaggcgaaa aagcgggcgg actgactgaa gaaatggccg    720
ggaagacagg gcttctggca ggtacggcgg tcgctgtcgc aaatgttgat gctcatgtgt    780
cggttccggc ggtcggcatc acagagccgg gcaagatgct gatgatcatg gaacgtctac    840
cctgtcacat gctgctcggc gaggatgtca ggatggtgcc gggaatgtgc ggcgtcgttg    900
aagacgggat tctgccgggc tatgtcggct atgaagcggg ccaatcgtgc gttggcgacc    960
attttcattg gctgattcaa cactttgttc cagaagcgta tttgaaagaa gctgaagccg   1020
aagggatttc catttacgaa ctgctgtctc aaaaggccgg cagtctccaa atcggtgaaa   1080
gcggtttgct tgcattggat tggtggaacg gaaaccgttc aacactcgtt gatgccgatc   1140
tgacgggaat gctgctcggt atgaccccttg ccactaagcc tgaagagata taccgtgcat   1200
tggttgaagc gactgcctgc gggacgagga tcattattga aacgttcaga caaagcggcg   1260
tgccgatcga ggagctgtat ccgcaggag gaatcgccga aaaaaatccg tttatcatgc   1320
aggtttacgc ggatgtcacc aacatggaaa tcaaaatttc cggatctccg caggcgccgg   1380
ctttaggttc agcgatattc ggagcgctcg cggccggaag catgaacggc ggttacgacc   1440
atatcgaaga agcagtcgca catatgggca agatcaagga taaaacgtac aaaccaattc   1500
ctgaaaacgt ttccttatac gatcagcttt atgcggaata taaggagctt tacacgtact   1560
tcggaaagca aaacaatgtg atgaaacgcc ttaaaaaatt gaaaaacatc cagtcccctta   1620 gttctgaccc cggtaaagcg atggcttaga gggaggaaa aactgtgctg gaatctttga   1680
aagaacaagt attaaaagcg aatttgcagc ttgaagaata ccggcttgtc acctttacat   1740
ggggaaatgt cagcggtatt gaccgggaga ataagctggt cgtcatcaag ccgagcggtg   1800
tcaaatacag cgatttgaaa gccgaagatt tagtggttct gaatatggac ggcgagattg   1860
tggaagggga tctgaagcca tcttccgata cgccgacaca cctctatctt taccggcagt   1920
ttcaatcgat cggcgggatc gtccatacgc attccccgtg ggcgacaagc tgggctcagt   1980
cagggaagga cattccgtcg ctcggaacga ctcatgccga ctactaccac ggcgacattc   2040
cgtgtacacg ggaaatggat cccgatgaaa tcaggagtca atacgagctg aatacaggaa   2100
aagtgattgt agagacgttc cggcatcttg acccccctggc ggtgcccgcc gttctcgtga   2160
acaatcacgg gccgttttgc tggggaaaag acgccttaac tgccgtacac aatgccgtcg   2220
tcctggaaga agtcgccaag atggcgtacc gctcccctgat gctgaatccg tctcttaagc   2280
ggattaagag cgcttttgcag gataagcatt attttcgaaa gcacggggca gacgcctatt   2340
acggccaata gaggagggaa gctgccaatg aatgacttga tctcttatgt gaaaaaaact   2400
ttgggcgcat gcgaatgcgg aaccgtccac cacccgctta cagtcgaaaa atcgcgatc   2460 ggcgacaatg ctgttgagca agagctgccc gctttcgtga atcggcttc ctataaaaaa   2520 gccgctgtca tttatgatga aacgaccgga cggttagccg gcaagcggat tgcctctctt   2580
cttgaggaaa cggctgaaac ggttccggtg ctgctggaag ctaatgaagc gggcgatgtg   2640
acggcggatg agcaaacatt ggtgagtgca ttgatcggtg taccgattga tgcggatgta   2700
ctaattgcgg ccggagcggg cacgattcac gacatcgtca ggttttgcgc ctatcagcgc   2760
ggcattccgt ttatttcagt tcctacggct ccgtcggttg acggttttac ttcagccggc   2820
gcaccgctga ttttaaaagg aaagaaacag acggttcaaa cgacagcgcc gatcgcgctt   2880
```

```
tttgccgatt tggagctctt gtgtcaagcg ccgcagaaca tggtagccgc aggttttggc    2940
gatatgctcg gcaaggtgac gtcgcttgcg gattgggaga tttcccgctt gcttgccggc    3000
gagccgtatt gtccggccgc cagccggctc acgagggaag cgcttgatca atgtcttgac    3060
cagtgaattc tgatcaaatg gttcagtgag agcgaagcga acacttgatt ttttaatttt    3120
ctatctttta taggtcatta gagtatactt atttgtccta taaactattt agcagcataa    3180
tagatttatt gaataggtca tttaagttga gcgtattaga ggaggaaaat cttggagaaa    3240
tatttgaaga acccgaacgc gtataataaa gaataataat aaatctgtag acaaattgtg    3300
aaaggatgta cttaaacgct aacggtcagc tttattgaac agtaatttaa gtatatgtcc    3360
aatctagggt aagtaaattg agtatcaata taaactttat atgaacataa tcaacgaggt    3420
gaaatcatga gcaatttgat taacggaaaa ataccaaatc aagcgattca acattaaaa    3480 atcgtaaaag atttatttgg aagttcaata gttggagtat atctatttgg ttcagcagta    3540
aatggtggtt tacgcattta cagcgatgta gatgttctag tcgtcgtgaa tcatagttta    3600
cctcaattaa ctcgaaaaaa actaacagaa agactaatga ctatatcagg aaagattgga    3660
aatacggatt ctgttagacc acttgaagtt acggttataa ataggagtga agttgtccct    3720
tggcaatatc ctccaaaaag agaatttata tacggtgagt ggctcaggtg tggatttgag    3780
aatggacaaa ttcaggaacc aagctatgat cctgatttgg ctattgtttt agcacaagca    3840
agaaagaata gtatttctct atttggtcct gattcttcaa gtatacttgt ctccgtacct    3900
ttgacagata ttcgaagagc aattaaggat tctttgccag aactaattga ggggataaaa    3960
ggtgatgagc gtaatgtaat tttaacccta gctcgaatgt ggcaaacagt gactactggt    4020
gaaattacct cgaaagatgt cgctgcggaa tgggctatac ctcttttacc taaagagcat    4080
gtaactttac tggatatagc cagaaaaggc tatcggggag agtgtgatga taagtgggaa    4140
ggactatatt caaaggtgaa agcactcgtt aagtatatga aaaattctat agaaacttct    4200
ctcaattagg ctaattttat tgcaataaca ggtgcttact tttaaaacta ctgatttatt    4260
gataaatatt gaacaatttt tgggaagaat aaagcgtcct cttgtgaaat tagagaacgc    4320
tttattactt taatttagtg aaacaatttg taactattga aaatagaaag aaattgttcc    4380
ttcgatagtt tattaatatt agtggagctc agtgagagcg aagcgaacac ttgatttttt    4440
aattttctat cttttatagg tcattagagt atacttattt gtcctataaa ctatttagca    4500
gcataataga tttattgaat aggtcattta agttgagcat attaggggag gaaaatcttg    4560
gagaaatatt tgaagaaccc gagatctaga tcaggtaccg caacgttcgc agatgctgct    4620
gaagagatta ttaaaagct gaaagcaaaa ggctatcaat tggtaactgt atctcagctt    4680
gaagaagtga agaagcagag aggctattga ataaatgagt agaaagcgcc atatcggcgc    4740
ttttcttttg gaagaaaata tagggaaaat ggtacttgtt aaaaattcgg aatatttata    4800
caatatcata tgtatcacat tgaaaggagg ggcctgctgt ccagactgtc cgctgtgtaa    4860
aaaaaaggaa taagggggg ttgacattat tttactgata tgtataatat aatttgtata    4920
agaaaatgga ggggccctcg aaacgtaaga tgaaacctta gataaagtg cttttttttgt    4980 tgcaattgaa gaattattaa tgttaagctt aattaaagat aatatctttg aattgagatc    5040
taatatcttt gaattgtaac gcccctcaaa agtaagaact acaaaaaaag aatacgttat    5100
atagaaatat gtttgaacct tcttcagatt acaaatatat tcggacggac tctacctcaa    5160
atgcttatct aactatagaa tgacatacaa gcacaacctt gaaaatttga aaatataact    5220
```

```
accaatgaac ttgttcatgt gaattatcgc tgtatttaat tttctcaatt caatatataa    5280
tatgccaata cattgttaca agtagaaatt aagacaccct tgatagcctt actataccta    5340
acatgatgta gtattaaatg aatatgtaaa tatatttatg ataagaagcg acttatttat    5400
aatcattaca tattttttcta ttggaatgat taagattcca atagaatagt gtataaatta   5460
tttatcttga aaggagggat gcctaaaaac gaagaacatt aaaaacatat atttgcaccg    5520
tctaatggat agaaaggagg tgatccagcc gcaccttatg aaaaatcatt ttatcagttt    5580
gaaaattatg tattatggaa gagctgaaag gggaggagaa ccatggaact agtctggatc    5640
ctacgcgttc atatgtatca cattgaaagg ggaggagaat catgatgagg aaaaagagtt    5700
tttggcttgg gatgctgacg gccttcatgc tcgtgttcac gatggcattc agcgattccg    5760
cttctgctgc tgaagaagca aaagaaaaat atttaattgg ctttaatgag caggaagctg    5820
tcagtgagtt tgtagaacaa gtagaggcaa atgacgaggt cgccattctc tctgaggaag    5880
aggaagtcga aattgaattg cttcatgaat ttgaaacgat tcctgtttta tccgttgagt    5940
taagcccaga agatgtggac gcgcttgaac tcgatccagc gatttcttat attgaagagg    6000
atgcagaagt aacgacaatg gcgcaatcgg taccatgggg aattagccgt gtgcaagccc    6060
cagctgccca taaccgtgga ttgacaggtt ctggtgtaaa agttgctgtc ctcgatacag    6120
ggatatccac tcatccagat ctaaatattc gtggtggcgc aagctttgta ccaggggaac    6180
cgtcgactca agatgggaat gggcatggca cgcatgtggc cgggacgatc gctgctttaa    6240
acaattcgat tggcgttctt ggcgtagctc ctagcgctga gctatacgct gttaaagtcc    6300 tagggggcgag cggttcaggc tcggtcagct cgattgccca aggattggaa tgggcaggga    6360
acaatggcat gcacgttgct aatttgagtt taggaagccc ttcgccaagt gccacactcg    6420
agcaagctgt taatagcgcg acttctagag gcgttcttgt tgtagcggca tctgggaatt    6480
caggtgcagg ctcaatcagc tatccggcgc gctatgcgaa cgcaatggca gtcggagcta    6540
ctgatcaaaa caacaaccgc gctagctttt cacagtatgg cgcaggcctt gacattgtcg    6600
cacccggggt aaacgtgcag agcacatacc caggttcaac atatgccagc ttaaacggta    6660
catcgatggc tactcctcat gttgcaggtg cggccgccct tgttaaacaa aagaaccccat    6720 cttggtctaa tgtacaaatt cgaaatcatc taaagaatac ggcaactagt ttaggaagca    6780
cgaacttgta tggaagcgga cttgttaacg cagaagcggc aacgcgttaa taacgcgtgc    6840
tagcggccgc gtcgactaga agagcagaga ggacggattt cctgaaggaa atccgttttt    6900 ttatttttgcc cgtcttataa atttcgttga tgctggttct cgaccattca aggccggctt    6960
ccggcggcga gcaccatctt tcccactacc ttgaaatgaa agcgctggag aacaataagc    7020
ggcaagtgct ccacggtgct aaagtcggct gcagcgcgat tatgctgact gacatttacc    7080
gatctcttat cggtgcaagc ctgggtgatc aacacgctga gcaagcgatt cgctccgttt    7140
atgaaaagct ccctgacggt aagaaaatgg cagagtggat gaggcgtatc ggcgggcctg    7200
tatcattcaa agaactcgat gttgaagaag agctggtgag agaagcgctc gcatacgccc    7260
atcagctcag agaccggtat acgggactga aaatcatcaa tcaatacggc cttttgccgg    7320
ggcttttagg caaaggacca ggcgtgaaag gggttaaaat gtgaaaaggt tcctttcatc    7380
tatctttatg gtcacggtcg ctgtatgttt gcttttatcg gggtgcaagg cgagtcctgc    7440
ctccgatcaa gcggacggca ccgaactgac attttggaca ttcaacgcc ttcatgaaca    7500 gttttatgct gagatggtga agaatgaa caaaaagtat cccgagcgaa aaatcaaatt    7560
aaatacagtg gtgtatccgt atggacagat gcatgacaat ttatctatct cgcttttagc    7620
```

```
cgggaaaggg gttccagata ttgccgatgt tgagctgggg cgctattcga acttttttgaa    7680 gggctctgac attcctctta ccgatttaac gccgcttgtg gaggacgaac gcgacaagtt    7740
tgttgaagcg aggctgacgc tctacagcaa gaacggcaag ctttacggac ttgacacaca    7800
tgtcggaact accgtgatgt attacaacat ggaaatgatg aataaagcag gcgttgatcc    7860
ggacgacatc aaaacatggg aagattacag ggaagcgggc aaaaaggtcg tcaaagctct    7920
cggaaagccg atgacgacga ttgaaacgac cgacccgaat tcatttctgc cgctggtttc    7980
ccagcaggga tccggttact ttgatgagca ggggcggttg acattaaaca atgagacaaa    8040
cgtgaaaacg ctcgaatttt taaagacttt aattgagaaa gacaaaattg ccgtcacaac    8100
gcccggaggc aatcatcaca gtgaagagta ttacggattt atgaaccaag gcggcgcggc    8160
gtctgtctta atgccgatct ggtatatggg ccgttttttg gattatatgc ctgacttgaa    8220
agggaaaatc gcgatcagac cgctgccggc atgggaagaa gggggagacc gctcagcggg    8280
aatgggcgga acgccaccg tgattccaaa acaggcgaaa caggtcgatc tggccaagga    8340
tttcttgaaa tttgccaaag cgtcaaagga aggcaacacc aagctgtgga ccgtgctcgg    8400
gttcgatccg ctcagatggg atgtgtggga ctcggacgaa ttgaaaaaaa caaatcaata    8460
tacagaatac tttcaaaacg gacaacacat cttttccgtg cttcttgaca taaaggatga    8520
gatcaatccg ctttaccttta ctgaggatta tgcgaagact tccgatctcg tcaacgaaaa    8580
catactgtac gaagcgctca aaacgaagag caaaacaccg aaagaagcat tggacaaagc    8640
agcagctgaa gtgaaagggc aatagtcttt cattactgta aagcgaggcg ataacttgaa    8700
gactgttaaa acagatacag tgcattcgtt ccgccggtg agcagaaaaa gaaagatcag    8760
acgtttatta tattcagcaa aagccgcacc ctacattttt acagcacctt ttgtactctc    8820
cttttgcata ttttttctt atccgcttat cagcgtcgtc atcatgagtt ttcaaagcat    8880
tctccccggg gaagtccgct tcatcggac ggagaactat aaaagcattaa acaatcctac    8940 attttatacc gcactattca acaccgtaaa atacacccttt tggacattgc tgattttaat    9000
acctgttcct cttattctgg cagtcttttt agattctaaa ctcgtaaagt ttaaaaacgt    9060
gttcaaatcg gctttattca tcccggctct gacttcaacc attgtggcgg ggattatttt    9120
caggctgatt tttggagaaa tggatacatc cctggcgaat tcgatattgg ctaagctcgg    9180
aggttcgccg tacaactggc tgaacaatga acataccggc atgttttaa tggtgatgct    9240 cgcatcttgg agatggatgg ggatcaatgt cctgtacttt ttggcgggct gcagaacgt    9300 tccgaaagaa ttgtatgaag ctgccgaaat cgacggggca ggcacgttca agaagtttta    9360
ccatattacg cttccgtttt taaagcccgt cagcgtctac gtgctgacga tcagcatcat    9420
cggcggcttc cggatgtttg aagaaagcta cgtgctgtgg cagaacaact ctccgggcaa    9480
catcggcctg acgatggtcg gatacattta tcagcagggg cttgcctaca acaacatggg    9540
ctacggatcg gcgctcggca tcgtgctctt gatcatcatt ttcatctgca gcctcatttc    9600
attaaagctg tctggatctt ttaaaaagga gggctattaa tgcgtcctgc cggaggcctc    9660
aacattgcga aagtagctct gtttctgctg tttgcgatat taagctttt gtttgtgttt    9720 ccgctcttct gccttgtact cggctcgctc aagccatctt cggaattgct gcgcttcggc    9780
ctgaatttaa agctgagccc tgaaatcctg agccttgaca attacactta cttgtttaac    9840
ggaggcagca tttattttca atggtttttcg aacagcttga ttctcgtggt gatatccacc    9900
gtgctgacgc tcttgttttc ttcaatggtc ggatacgggc ttgccgtcta cg    9952
```